US010274503B2

(12) United States Patent
Baldwin et al.

(10) Patent No.: US 10,274,503 B2
(45) Date of Patent: Apr. 30, 2019

(54) METHODS OF USING VEGF-C BIOMARKERS FOR AGE-RELATED MACULAR DEGENERATION (AMD) DIAGNOSIS

(71) Applicants: Megan E. Baldwin, Brighton East (AU); Kameran Lashkari, Boston, MA (US); Jie Ma, Boston, MA (US)

(72) Inventors: Megan E. Baldwin, Brighton East (AU); Kameran Lashkari, Boston, MA (US); Jie Ma, Boston, MA (US)

(73) Assignees: VEGENICS PTY LIMITED, South Yarra, Victoria (AU); THE SCHEPENS EYE RESEARCH INSTITUTE, INC., Boston, MA (US)

( * ) Notice: Subject to any disclaimer, the term of this patent is extended or adjusted under 35 U.S.C. 154(b) by 46 days.

(21) Appl. No.: 14/888,062

(22) PCT Filed: May 5, 2014

(86) PCT No.: PCT/US2014/036865
§ 371 (c)(1),
(2) Date: Oct. 29, 2015

(87) PCT Pub. No.: WO2014/182635
PCT Pub. Date: Nov. 13, 2014

(65) Prior Publication Data
US 2016/0084853 A1    Mar. 24, 2016

Related U.S. Application Data

(60) Provisional application No. 61/821,056, filed on May 8, 2013.

(51) Int. Cl.
| | | |
|---|---|---|
| A61K 38/16 | (2006.01) |
| G01N 33/53 | (2006.01) |
| G01N 33/74 | (2006.01) |
| A61K 38/17 | (2006.01) |
| G01N 33/68 | (2006.01) |
| A61K 9/00 | (2006.01) |
| A61K 38/45 | (2006.01) |
| A61K 39/395 | (2006.01) |

(52) U.S. Cl.
CPC .......... *G01N 33/74* (2013.01); *A61K 38/179* (2013.01); *A61K 9/0048* (2013.01); *A61K 38/45* (2013.01); *A61K 39/395* (2013.01); *C12Y 207/10001* (2013.01); *G01N 33/68* (2013.01); *G01N 2333/475* (2013.01); *G01N 2800/16* (2013.01); *G01N 2800/164* (2013.01); *G01N 2800/50* (2013.01); *G01N 2800/52* (2013.01); *G01N 2800/7014* (2013.01)

(58) Field of Classification Search
None
See application file for complete search history.

(56) References Cited

U.S. PATENT DOCUMENTS

| 3,832,253 A | 8/1974 | Palma et al. |
| 3,854,480 A | 12/1974 | Zaffaroni |
| 3,929,922 A | 12/1975 | Wilke et al. |
| 4,452,775 A | 6/1984 | Kent |
| 4,667,014 A | 5/1987 | Nestor, Jr. et al. |
| 4,748,034 A | 5/1988 | de Rham |
| 5,075,109 A | 12/1991 | Tice et al. |
| 5,239,660 A | 8/1993 | Ooi |
| 5,288,711 A | 2/1994 | Mitchell et al. |
| 5,362,718 A | 11/1994 | Skotnicki et al. |
| 5,433,505 A | 7/1995 | Coyne et al. |
| 5,516,781 A | 5/1996 | Morris et al. |
| 5,840,301 A | 11/1998 | Rockwell et al. |
| 5,861,484 A | 1/1999 | Kendall et al. |
| 5,869,079 A | 2/1999 | Wong et al. |
| 5,874,542 A | 2/1999 | Rockwell et al. |
| 5,955,311 A | 9/1999 | Rockwell et al. |
| 6,107,046 A | 8/2000 | Alitalo et al. |
| 6,277,983 B1 | 8/2001 | Shaw et al. |
| 6,331,313 B1 | 12/2001 | Wong et al. |
| 6,344,339 B1 | 2/2002 | Menrad et al. |
| 6,403,088 B1 | 6/2002 | Alitalo et al. |
| 6,503,921 B2 | 1/2003 | Naicker et al. |

(Continued)

FOREIGN PATENT DOCUMENTS

| EP | 663916 A1 | 7/1995 |
| WO | WO-1990/007641 A1 | 7/1990 |

(Continued)

OTHER PUBLICATIONS

Liu et al. Cell 165: 535-550, 2016.*
Kendrick Labs, Inc., 2014) (https://kendricklabs.com/wp-content/uploads/2016/08/WP1_mRNAvsProtein_KendrickLabs.pdf)., downloaded Oct. 19, 2018.*
AREDS Research Group, A randomized, placebo-controlled, clinical trial of high-dose supplementation with vitamins C and E, beta carotene, and zinc for age-related macular degeneration and vision loss: AREDS report No. 8. Arch. Opthalmol. 119(10): 1417-36 (2001).

(Continued)

*Primary Examiner* — Christine J Saoud
(74) *Attorney, Agent, or Firm* — Marshall, Gerstein & Borun LLP

(57) ABSTRACT

The present application is directed to the use of a VEGF-C inhibitor, a VEGFR-2 inhibitor and/or a VEGFR-3 inhibitor as a prophylactic or therapeutic for the treatment of eye disorders such as a maculopathy and pathogenic ocular neovascularization. The application is also directed to the use of a VEGF-C measurement from a biological sample from a mammalian subject as a predictive marker, a selected marker, a responsive marker or a tracking marker for a disease or condition selected from the group consisting of a maculopathy and pathogenic ocular neovascularization.

33 Claims, 14 Drawing Sheets

Specification includes a Sequence Listing.

(56) References Cited

U.S. PATENT DOCUMENTS

| | | | |
|---|---|---|---|
| 6,617,333 | B2 | 9/2003 | Rabindran et al. |
| 6,660,297 | B2 | 12/2003 | Bartels et al. |
| 6,824,777 | B1 | 11/2004 | Alitalo et al. |
| 6,878,720 | B2 | 4/2005 | Altmann et al. |
| 6,887,468 | B1 | 5/2005 | Thorpe et al. |
| 6,897,294 | B2 | 5/2005 | Davis-Smyth et al. |
| 6,986,890 | B1 | 1/2006 | Shitara et al. |
| 7,045,133 | B2 | 5/2006 | Achen et al. |
| 7,052,693 | B2 | 5/2006 | Shitara et al. |
| 7,056,509 | B2 | 6/2006 | Thorpe et al. |
| 7,109,308 | B1 | 9/2006 | Rosen et al. |
| 7,208,582 | B2 | 4/2007 | Rosen et al. |
| 7,402,312 | B2 | 7/2008 | Rosen et al. |
| 7,422,741 | B2 | 9/2008 | Alitalo et al. |
| 7,423,125 | B2 | 9/2008 | Alitalo et al. |
| 7,576,189 | B2 | 8/2009 | Rosen et al. |
| 7,850,963 | B2 | 12/2010 | Rosen et al. |
| 9,328,162 | B2 * | 5/2016 | Dana |
| 2002/0164667 | A1 | 11/2002 | Alitalo et al. |
| 2003/0073737 | A1 | 4/2003 | Cooke et al. |
| 2003/0170287 | A1 | 9/2003 | Prescott |
| 2003/0176674 | A1 | 9/2003 | Rosen et al. |
| 2004/0147726 | A1 | 7/2004 | Alitalo et al. |
| 2005/0059117 | A1 | 3/2005 | Rosen et al. |
| 2005/0171039 | A1 | 8/2005 | McSwiggen et al. |
| 2005/0192429 | A1 | 9/2005 | Rosen et al. |
| 2005/0222066 | A1 | 10/2005 | Richards et al. |
| 2005/0232921 | A1 | 10/2005 | Rosen et al. |
| 2005/0233998 | A1 | 10/2005 | Jadhav et al. |
| 2005/0282228 | A1 | 12/2005 | Mccoll et al. |
| 2006/0025370 | A1 | 2/2006 | Trask et al. |
| 2006/0030000 | A1 | 2/2006 | Alitalo et al. |
| 2006/0121025 | A1 | 6/2006 | Lee et al. |
| 2006/0177901 | A1 | 8/2006 | Alitalo et al. |
| 2006/0217332 | A1 | 9/2006 | Vargeese et al. |
| 2006/0269548 | A1 | 11/2006 | Alitalo et al. |
| 2012/0100136 | A1 | 4/2012 | Patel et al. |

FOREIGN PATENT DOCUMENTS

| | | | |
|---|---|---|---|
| WO | WO-1994/009010 A1 | 4/1994 | |
| WO | WO-1995/033772 A1 | 12/1995 | |
| WO | WO-1996/041807 A1 | 12/1996 | |
| WO | WO-1997/005250 A2 | 2/1997 | |
| WO | WO-1998/002441 A2 | 1/1998 | |
| WO | WO-1998/033197 A1 | 7/1998 | |
| WO | WO-2000/021560 A1 | 4/2000 | |
| WO | WO-2000/023565 A2 | 4/2000 | |
| WO | WO-2001/002441 A1 | 1/2001 | |
| WO | WO-2001/003737 A1 | 1/2001 | |
| WO | WO-2001/014387 A1 | 3/2001 | |
| WO | WO-2002/060950 A2 | 8/2002 | |
| WO | WO-2004/009773 A2 | 1/2004 | |
| WO | WO-2005/083430 A1 | 9/2005 | |
| WO | WO-2005/087808 A2 | 9/2005 | |
| WO | WO-2005/098909 A2 | 10/2005 | |
| WO | WO-2014/124487 A1 | 8/2014 | |
| WO | WO-2015/123715 A1 | 8/2015 | |

OTHER PUBLICATIONS

Bergsten et al., PDGF-D is a specific, protease-activated ligand for the PDGF beta-receptor. *Nat. Cell Biol.* 3(5): 512-6 (2001).

Betsholtz et al., Developmental roles of platelet-derived growth factors. *Bioessays*, 23(6): 494-507 (2001).

Campochiaro, Ocular neovascularisation and excessive vascular permeability. *Expert Opin. Biol. Ther.* 4(9): 1395-402 (2004).

Chard et al., Alpha interferon in human pregnancy. *Br. J. Obstet. Gynaecol.* 93(11): 1145-9 (1986).

Ferrara, Vascular endothelial growth factor: basic science and clinical progress. *Endocr. Rev.* 25(4): 581-611 (2004).

Forooghian et al., Hypoxia-inducible factor expression in human RPE cells. *Br. J. Ophthalmol.* 91: 1406-10 (2007).

Goydos et al., Melanoma correlates with stage of progression in patients with vascular endothelial growth factor C mRNA expression. *Clin. Cancer Res.* 9(16 Pt 1): 5962-7 (2003).

Harris et al., Soluble Tie2 and Flt1 extracellular domains in serum of patients with renal cancer and response to antiangiogenic therapy. *Clin. Cancer Res.* 7(7): 1992-7 (2001).

International Search Report and Written Opinion of the International Searching Authority in connection with International Application No. PCT/US2014/036865, United States Patent Office, dated May 5, 2014.

Jones et al., RNA quantification by fluorescence-based solution assay: RiboGreen reagent characterization. *Anal. Biochem.* 265(2): 368-74 (1998).

Kumar et al., Co-culture of retinal and endothelial cells results in the modulation of genes critical to retinal neovascularization. *Vascular Cell*, 3: 27-41 (2011).

Kuo et al., Genetic risk, ethnic variations and pharmacogenetic biomarkers in age-related macular degeneration and polypoidal choroidal vasculopathy. *Expert Rev. Opthalmol.* 8(2): 127-40 (2013).

Lavey et al., VEGF-C as a survival factor for retinal pigment epithelial cells from photothermal stress. *Optical Interactions With Tissue and Cells XXII*, 7897(1): 1-7 (2011).

Leclers et al., VEGFR-3, VEGF-C and VEGF-D mRNA quantification by RT-PCR in different human cell types. *Anticancer Res.* 26(3A): 1885-91 (2006).

Li et al., PDGF-C is a new protease-activated ligand for the PDGF alpha-receptor. *Nat. Cell Biol.* 2(5): 302-9 (2000).

Lim et al., Age-related macular degeneration. *Lancet*, 379(9827): 1728-38 (2012).

Makinen et al., Inhibition of lymphangiogenesis with resulting lymphedema in transgenic mice expressing soluble VEGF receptor-3. *Nat. Med.* 7(2): 199-205 (2001).

Matsuno et al., Lack of alpha 2-antiplasmin promotes re-endothelialization via over-release of VEGF after vascular injury in mice. *Blood*, 120(10): 3621-8 (2003).

Morin, From oncogene to drug: development of small molecule tyrosine kinase inhibitors as anti-tumor and anti-angiogenic agents. *Oncogene*, 19(56): 6574-83 (2000).

Nagineni et al., Resveratrol suppresses expression of VEGF by human retinal pigment epithelial cells: Potential nutraceutical for age-related macular degeneration. *Aging Dis.* 5(2): 88-100 (2014).

Nakamura et al., KRN633: A selective inhibitor of vascular endothelial growth factor receptor-2 tyrosine kinase that suppresses tumor angiogenesis and growth. *Mol. Cancer Ther.* 3(12): 1639-49 (2004).

Nakao et al., Lymphatics and Lymphangiogenesis in the eye. *J. Ophthalmol.* 2012: 1-11 (2012).

Nussenblatt et al., Perspectives: Age related macular degeneration and the immune response-Implications for therapy. *Am. J. Ophthalmol.* 144(4): 618-26 (2007).

Opthea Pty Ltd, VEGF-C shown to have major role in age-related macular degeneration (AMD) <http://www.reuters.com/article/2013/05/08/ldUSnGNX1QLlf7+1d8+GNW20130508>, retrieved on Sep. 15, 2014.

Ross et al., Genetic markers and biomarkers for age-related macular degeneration. *Expert Rev. Opthalmol.* 2(3): 443-57 (2007).

Saint-Geniez et al., An essential role for RPE-derived soluble VEGF in the maintenance of the choriocapillaris. *Proc. Natl. Acad. Sci. USA* 106(44): 18751-6 (2009).

Sambrook et al., Molecular Cloning: A Laboratory Manual. Cold Spring Harbor Press, 2nd ed. (1989).

Seddon et al., Dietary carotenoids, vitamins A, C, and E, and advanced age-related macular degeneration. Eye Disease Case-Control Study Group. *JAMA*, 272(18): 1413-20 (1994).

Sharma et al., New biomarker for neovascular age-related macular degeneration: eotaxin-2. *DNA Cell Biol.* 31(11): 1618-27 (2012).

Tijssen et al., The influence of physostigmine on visual-vestibular interaction in hereditary ataxias. *J. Neurol. Neurosurg. Psychiatry*, 48(10): 977-81 (1985).

Tucillo et al., Antitumor activity of ZD6474, a vascular endothelial growth factor-2 and epidermal growth factor receptor small molecule tyrosine kinase inhibitor, in combination with SC-236, a cyclooxygenase-2 inhibitor. *Clin. Cancer Res.* 11(3): 1268-76 (2005).

(56) References Cited

OTHER PUBLICATIONS

UniProt Accession No. P35968, Vascular endothelial growth factor receptor 2, dated Jun. 1, 1994.
Uutele et al., Chromosomal location, exon structure, and vascular expression patterns of the human PDGFC and PDGFD genes. *Circulation*, 103(18): 2242-7 (2001).
Verheul et al., Vascular endothelial growth factor and its inhibitors. *Drugs Today (Barc)*, 39 Suppl C: 81-93 (2003).
Zhao et al., VEGF-A regulates the expression of VEGF-C in human retinal pigment epithelial cells. *Br. J. Ophthalmol.* 90(8): 1052-9 (2006).

\* cited by examiner

METHODS OF USING VEGF-C BIOMARKERS FOR AGE-RELATED MACULAR DEGENERATION (AMD) DIAGNOSIS

TECHNICAL FIELD

This invention relates to methods of using biomarkers as diagnostic and prognostic tools for age-related macular degeneration (AMD), and methods for treating, preventing or delaying the development or progression of AMD.

BACKGROUND

Age-related macular degeneration (AMD) is a sudden worsening and distortion of central vision that progresses rapidly, typically with a course of only weeks or months. AMD is characterized by abnormalities in the macular area. The central area (or fovea) of the macula contains the highest density of cone photoreceptors in the retina and mediates high-acuity vision. The disease typically has a preclinical, asymptomatic phase, in which extracellular waste material accumulates in the space between the basement membrane (Bruch's membrane) and the epithelial layer, forming yellow-white spots known as drusen. Advanced forms of AMD includes both dry and wet (or "neovascular") AMD. The dry form of AMD is far more common, but the wet form occurs simultaneously with the dry form in about 15% of cases. Dry AMD is characterized by progressive apoptosis of cells in the epithelial layer, in the overlying photoreceptor cells and in the underlying cells in the choroidal capillary layer. Wet AMD is characterized by choroidal neovascularization with vascular leakage into subretinal spaces.

AMD impairs central vision that is required for reading, driving, face recognition and fine visual tasks. Neurosensory detachment, retinal hemorrhages and retinal scarring gradually result in decreased visual function of photoreceptors in the central vision, eventually resulting in legal blindness, with preservation of peripheral vision. AMD is the most common cause of blindness among the elderly. Subjects with a family history of AMD and those who smoke have a higher risk than non-smokers and those with no family history. Nevertheless, subjects who have favorable risk profiles also develop the disease. Current therapeutic efforts and clinical trials are primarily aimed at halting the growth of the neovascular membrane in wet AMD, e.g., using angiogenesis (VEGF-A) inhibitors, laser photocoagulation and/or photodynamic therapy. Antioxidants can retard the progression of the disease.

Despite advances in treatment, AMD is still the most common cause of visual impairment in the developed world. Although genetic biomarkers are reasonably effective predictors of AMD risk and advanced AMD risk, there remains a significant need for new biomarkers that will improve the level of early diagnosis and enable treatments to be targeted to meet individual patient needs.

SUMMARY

The work described herein demonstrates that vascular endothelial growth factor C (VEGF-C) is a biomarker associated with AMD. The level of VEGF-C gene or protein expression can be used as a biomarker for assessing the risk of developing and/or progression of AMD and/or to determine the likelihood that specific subjects will benefit from certain treatments or therapies for AMD.

In one aspect, described herein are new diagnostic or screening methods for a subject comprising measuring the level of VEGF-C expression in a biological sample from a subject to obtain a VEGF-C measurement, which VEGF-C measurement can be used to predict a subject's risk of developing AMD and/or progressing to more advanced AMD. In such methods, VEGF-C can be broadly considered to be a "predictive biomarker". These methods can be used, for example, to predict risk of development or progression of age-related maculopathy.

In another aspect, described herein are new selection or screening methods for a subject comprising measuring the level of VEGF-C expression in a biological sample from a subject to obtain a VEGF-C measurement, which VEGF-C measurement can be used to select subjects for a clinical trial, and/or to select subjects likely to benefit from certain treatments, treatment regimes or therapies for AMD. In such methods, VEGF-C can be broadly considered to be a "selective biomarker", i.e. it is being used to identify subjects likely to benefit from certain treatments, treatment regimes or therapies (i.e. targeted therapy) or in a particular clinical trial for an AMD therapy. These methods can be used, for example, to determine the likelihood that certain subjects will benefit from the use of certain treatments, treatment regimes or therapies designed to prevent development or progression of AMD and/or designed to treat AMD. In one embodiment, subjects are identified who will benefit from treatment with an anti-angiogenic agent. In another embodiment, subjects are identified who will benefit from treatment with a VEGFR-2 inhibitor molecule and/or a VEGFR-3 inhibitor molecule (e.g. an inhibitor of VEGF-A, VEGF-C, VEGF-D, VEGFR-2 or VEGFR-3).

In another aspect, described herein are new monitoring or selection methods for a subject comprising measuring the level of VEGF-C expression in a biological sample from a subject to obtain a VEGF-C measurement, which VEGF-C measurement can be used as a monitor of disease progression or as a monitor of the efficacy of response to certain treatments, treatment regimes or therapies in subjects being treated for AMD. In such methods, VEGF-C can be broadly considered to be a "responsive biomarker" or a "tracking biomarker" in which, for example, it is being used to monitor or track the response to a certain treatment, treatment regime or therapy.

The invention also provides methods for treating, preventing, and/or delaying the development or progression of AMD.

In some embodiments, the biological sample comprises a tissue biopsy and the VEGF-C is measured in the tissue. In other embodiments, the biological sample includes blood or lymphatic tissue and the VEGF-C is measured in the vessel tissue.

In other embodiments, the biological sample includes fluid from or around the area of the AMD (e.g. fluid from or around the eye) and the VEGF-C is measured in the fluid. In still further embodiments, the biological sample comprises blood, and the VEGF-C is measured in the blood, or in plasma or serum from the blood.

In a preferred embodiment, VEGF-C acts as a systemic biomarker. In another preferred embodiment, the biological sample comprises blood, and the VEGF-C is measured in the blood, or in plasma or serum from the blood. In a particularly preferred embodiment, the biological sample comprises blood, and the VEGF-C is measured in plasma from the blood.

The VEGF-C measurement may be used as a "predictive" biomarker for the prediction of development and/or progression of AMD, as a "selective" biomarker for the selection of subjects for clinical trials or the selection of subjects likely to benefit from certain treatments for AMD, or as a "responsive" or "tracking" biomarker for monitoring of AMD disease progression in a subject and/or monitoring the efficacy of a particular treatment, treatment regime or therapy in a subject being treated for AMD. VEGF-C measurements in otherwise healthy subjects, regardless of whether they have ever smoked, may also be predictive of development and progression of AMD.

In addition, the likelihood that a specific subject will benefit to a greater or a lesser extent from the use of certain therapeutic agents for reducing the risk of development or progression of AMD can be determined by evaluating levels of VEGF-C in the subject, and comparing the levels to a reference or control for the marker.

In another aspect, described herein are new methods for characterizing a mammalian subject's risk of development or progression of AMD comprising measuring the level of VEGF-C expression in a biological sample from a mammalian subject to obtain a VEGF-C measurement and comparing the subject's VEGF-C measurement with a reference or control level, the subject's risk of development or progression of AMD being characterized based upon the VEGF-C measurement in comparison to the reference or control.

In some embodiments, the level of the subject's VEGF-C is higher than the reference or control (e.g. increased relative to a control or other reference (including a previous level obtained from the same subject)), and indicates that the subject:

(i) has an increased risk of development or progression of AMD;

(ii) has an increased likelihood of benefiting from certain treatments for AMD or benefiting from a clinical trial; or (iii) is not responding to a particular treatment or therapy for AMD and/or that the AMD is progressing.

In some embodiments, the level of the subject's VEGF-C is lower than the reference or control (e.g. reduced relative to a control or other reference (including a previous level obtained from the same subject)), and indicates that the subject:

(i) has an decreased risk of development or progression of AMD;

(ii) has an decreased likelihood of benefiting from certain treatments for AMD or benefiting from a clinical trial; or (iii) is responding to a particular treatment or therapy for AMD and/or that the AMD is not progressing further (i.e. is stable) or is in remission.

As used herein, progression of AMD refers to an increase in severity of the disease, e.g., an objective worsening in one or more parameters or symptoms associated with the disease, e.g., a progression from Category 1 or 2 to Category 3 or 4, or a progression from Category 1, 2, or 3 to Category 4. In some embodiments, the subject is re-evaluated, e.g., the level of the VEGF-C as a biomarker is obtained again after or during administration of a treatment (e.g., after administration of one or more doses of an inhibitor of the VEGFR-2 and/or VEGFR-3 pathway, and in particular the VEGFR-3 pathway), and the level is compared to a reference or control, e.g., the level previously obtained, to evaluate the efficacy of the treatment. In some embodiments, after administration of the treatment, the level of VEGF-C is reduced as compared to a previously-obtained level, and it indicates that the subject's risk or development or progression of AMD is reduced.

According to yet another aspect of the invention, methods are provided that use a subject's VEGF-C level together with one or more risk factors or other biomarkers for AMD, e.g., as described herein, to characterize a subject's risk profile of development and/or progression of AMD. The methods include obtaining a level of VEGF-C as biomarker in the subject which level is compared to a reference or control to establish a first risk value. At least one risk factor or other biomarker for AMD is also evaluated. The presence or level of the risk factor or other biomarker in the subject is compared to a second reference to establish a second risk value. The subject's risk profile for development or progression of AMD is characterized based upon the combination of the first risk value and the second risk value, wherein the combination of the first risk value and second risk value establishes a combined risk value, which is typically different from the first and second risk values. In some embodiments, the combined risk value is greater than either of the first and second risk values, e.g., the first and second risk values are additive. In some embodiments, the combined risk value is calculated with a multiplicative model. In some variations, logistic regression is used to calculate a combine risk value.

In another aspect of the invention, methods are provided for evaluating the likelihood that a subject will benefit from treatment with a VEGFR-2 inhibitor molecule and/or a VEGFR-3 inhibitor molecule, and in particular the VEGFR-3 pathway, to reduce the risk of development or progression of AMD. The methods include obtaining a level of VEGF-C (e.g. active angiogenesis VEGF-C level) in a subject. This level then is compared to a reference or control, wherein the level of the VEGF-C in the subject in comparison to the reference or control is indicative of the likelihood that the subject will benefit from treatment with the agent. The subject then can be characterized in terms of the net benefit likely to be obtained by treatment with the agent.

In a further aspect, the invention provides methods for determining whether a treatment or prevention for reducing risk of development of AMD or progression to advanced AMD is having an effect in a subject. The methods include obtaining a first level of VEGF-C in a subject; administering a selected treatment or prevention for AMD to the subject; obtaining a second level of VEGF-C in the subject; and comparing the first VEGF-C level to the second level of VEGF-C. A difference, or lack of difference, in the second level as compared to the first level indicates whether the treatment or prevention is effective or not effective. For example, if the second level is lower than the first level, then the treatment or prevention is likely to be effective. If there is no difference, or if the second level is higher than the first level, then the treatment or prevention is likely not to be effective, or has not yet become effective. The methods can include re-testing the subject a plurality of times, e.g., to determine whether the treatment is effective over time. In addition, once a treatment has been stopped, the subject can be tested one or more additional times to determine if their risk of developing AMD has changed or the subject has relapsed into AMD or AMD has started to progress after being in a stable condition.

In some embodiments, the subject is apparently healthy, e.g., has no or few overt clinical signs of AMD (e.g., is in the first AERDS category); has minimal or early AMD (e.g., is in the second AERDS category); has intermediate AMD (e.g., is in the third AERDS category); or has advanced AMD (e.g., is in the fourth AERDS). In some embodiments, the subject is a non-smoker, e.g., has never smoked, or is a smoker, e.g., a current or past smoker. A non-smoker is a subject who, at the time of the evaluation, has never smoked, or has smoked less than a minimal number, e.g., 100 cigarettes in a lifetime, or less than a minimal duration, e.g., less than six months. Smokers include subjects who currently smoke, as well as subjects who have smoked at some time in the past but presently no longer smoke, or smoked more than a minimal number, e.g., 100 cigarettes in a lifetime, or more than a minimal duration, e.g., more than six months. In some embodiments, the subject has no risk factors as described herein. In some embodiments, the subject has one or more risk factors as described herein.

In some embodiments, characterizing a subject's risk of development or progression of AMD includes characterizing the subject's risk of developing advanced AMD. In some embodiments, characterizing the subject's risk of future development or progression of AMD includes characterizing the subject's risk of developing neovascular AMD.

The reference can be a single value, multiple values, a single range or multiple ranges. In some embodiments, the reference is a median value. In some embodiments, the reference is a plurality of marker level ranges, e.g., ranges associated with low, medium, and high risk categories, and the comparing step comprises determining in which marker level range the subject's level falls.

In some embodiments, levels of multiple AMD biomarkers are obtained concurrently.

One of skill in the art will appreciate that the reference value selected will typically depend on the particular marker selected and even upon the characteristics of the patient population in which the subject lies, described in greater detail below.

As mentioned above, the methods described herein can be adapted to determine which subjects are most likely to benefit from treatment with an agent for reducing the risk in the development or progression of AMD. The methods can also be used to select candidate subjects and/or populations for clinical trials and for treatment with candidate drugs, by identifying, for example, subjects most likely to benefit from a new treatment or from a known treatment with a high risk profile of adverse side effects. Thus, the methods described herein can provide information for evaluating the likely net benefit of certain treatments for candidate subjects.

Any available technique can be used for measuring VEGF-C expression, including direct and indirect techniques. For example, in one variation, the measuring comprises measuring VEGF-C protein in the biological sample. Exemplary techniques for measuring amounts or concentrations of VEGF-C protein in a sample are immunological techniques that involve use of a polyclonal or monoclonal antibody that specifically binds VEGF-C, or use of a VEGF-C-binding fragment of such an antibody. For example, the measuring comprises contacting the biological sample with a VEGF-C antibody (or with a polypeptide comprising an extracellular domain (ECD) fragment of VEGFR-3 that binds VEGF-C) or antigen-binding fragment thereof. Quantification of the amount of bound antibody (e.g., using a label or second, labeled antibody) provides a measurement of VEGF-C protein expressed in the sample. Immunoassays such as radioimmunoassay, immunoradiometric assay (labeled antibody), or an enzyme-linked immunosorbent assay (ELISA) are contemplated.

In another variation, the measuring comprises measuring VEGF-C mRNA in the biological sample. Any available assay for measuring specific oligonucleotides is suitable. One technique for measuring VEGF-C mRNA comprises in situ hybridization to measure VEGF-C mRNA in the biological sample. Other techniques involve steps of isolating mRNA from the biological sample and measuring VEGF-C mRNA in the isolated mRNA, for example, by Northern hybridization procedures. In still another variation, quantitative reverse transcriptase polymerase chain reaction (PCR), real-time PCR, or other PCR techniques are employed to quantitatively amplify VEGF-C mRNA (relative to control samples) to provide a quantitative measurement of VEGF-C mRNA in the biological sample.

The screening, diagnosing or selecting methods described herein may optionally comprise the step of prescribing for or administering to the subject identified as having elevated VEGF-C expression in the biological sample a composition comprising a VEGFR-2 inhibitor molecule and/or a VEGFR-3 inhibitor molecule (e.g. a VEGF-C antibody or a soluble VEGFR-3 protein trap).

In another aspect, described herein is a method of treatment comprising obtaining a biological sample from a mammalian subject, determining that the biological sample has elevated expression of VEGF-C, and prescribing for or administering to the subject a composition comprising a VEGFR-2 inhibitor molecule and/or a VEGFR-3 inhibitor molecule (e.g. a VEGF-C antibody or a soluble VEGFR-3 protein trap). In some variations, the subject for whom the inhibitor composition is prescribed receives the composition following the prescribing.

In some variations, the determining step comprises ordering a laboratory test that measures VEGF-C in the biological sample and learning the measurement from a report from the laboratory. In other variations, the determining step comprises measuring VEGF-C mRNA or VEGF-C protein in the biological sample.

Aspects of the invention that are described herein as methods (especially methods that involve treatment) can alternatively be described as (medical) uses of reagents or therapeutics. For example, in one variation, the invention is a use of a composition that comprises a VEGFR-2 inhibitor molecule and/or a VEGFR-3 inhibitor molecule for the treatment of AMD in a subject identified with AMD and identified with elevated VEGF-C expression (wherein the subject is identified as having elevated VEGF-C expression in the AMD by a method described herein).

Agents contemplated which inhibit the VEGFR-2 pathway (VEGFR-2 inhibitor molecules) for use in the methods (or uses) described herein include, but are not limited to, (a) a VEGF-A antibody that inhibits ligand-mediated stimulation of VEGFR-2; (b) a VEGF-C antibody that inhibits ligand-mediated stimulation of VEGFR-2; (c) a VEGF-D antibody that inhibits ligand-mediated stimulation of VEGFR-2; (d) a soluble polypeptide that comprises an extracellular domain fragment of VEGFR-2 (i.e. a soluble VEGFR-2 trap) that binds VEGF-A and/or VEGF-C and/or VEGF-D and inhibits VEGF-A and/or VEGF-C and/or VEGF-D, as the case may be, from stimulating VEGFR-2; (e) an antisense or interfering nucleic acid (e.g., antisense oligonucleotide; micro-RNA, short interfering RNA) that inhibits VEGF-A, VEGF-C and/or VEGF-D expression; (e) an antisense or interfering nucleic acid (e.g., antisense oligonucleotide; micro-RNA, short interfering RNA) that inhibits VEGFR-2 expression; (f) an antibody that binds VEGFR-2 and inhibits VEGF-A and/or VEGF-C and/or VEGF-D from binding to and stimulating VEGFR-2; (g) a small molecule that inhibits VEGFR-2 expression or signaling; and (h) a molecule that inhibits proteolytic cleavage-activation of VEGF-C or VEGF-D.

Agents contemplated which inhibit the VEGFR-3 pathway (VEGFR-3 inhibitor molecules) for use in the methods (or uses) described herein include, but are not limited to, (a) a VEGF-C antibody that inhibits ligand-mediated stimulation of VEGFR-3; (b) a VEGF-D antibody that inhibits ligand-mediated stimulation of VEGFR-3; (c) a soluble polypeptide that comprises an extracellular domain fragment of VEGFR-3 (i.e. a soluble VEGFR-3 trap) that binds VEGF-C and/or VEGF-D and inhibits VEGF-C and/or VEGF-D, as the case may be, from stimulating VEGFR-3; (d) an antisense or interfering nucleic acid (e.g., antisense oligonucleotide; micro-RNA, short interfering RNA) that inhibits VEGF-C and/or VEGF-D expression; (e) an antisense or interfering nucleic acid (e.g., antisense oligonucleotide; micro-RNA, short interfering RNA) that inhibits VEGFR-3 expression; (f) an antibody that binds VEGFR-3 and inhibits VEGF-C and/or VEGF-D from binding to and stimulating VEGFR-3; (g) a small molecule that inhibits VEGFR-3 expression or signaling; and (h) a molecule that inhibits proteolytic cleavage-activation of VEGF-C or VEGF-D.

In the treatment methods (or uses) described herein, the methods optionally comprise administering to the subject in combination a VEGFR-2 inhibitor molecule and/or a VEGFR-3 inhibitor molecule and a standard or care therapeutic. With respect to any combination treatment or therapy regimes described herein, the VEGFR-2 inhibitor molecule and/or a VEGFR-3 inhibitor molecule can be administered simultaneously with the other active agents, which may be in admixture with the VEGFR-2 inhibitor molecule and/or a VEGFR-3 inhibitor molecule, or may be in a separate composition. Each composition preferably includes a pharmaceutically acceptable diluent, adjuvant, or carrier. When the agents are separately administered, they may be administered in any order.

The invention also includes kits including a package including one or more assays for an AMD biomarker as described herein and instructions for use in a method described herein, and optionally related materials such as marker level or range information for correlating the level of the marker as determined by the assay with a risk of development or progression of AMD. Such information can be in any useful form, e.g., charts, e.g., numeric or colour charts. In some embodiments, the instructions include information for determining the subject's risk of development or progression of AMD, by correlating the level of the marker determined by the assay and one or more risk factors with a risk of development or progression of AMD. In some embodiments, the kit includes assays for two, three, four or more AMD biomarkers. For example, the kit can include a microarray or a microfluidic device that can be used to determine the levels of two, three, four, or more AMD biomarkers, e.g., substantially simultaneously.

The invention also involves methods for treating subjects with agents that inhibit the VEGFR-2 and/or VEGFR-3 pathways, and in particular the VEGFR-3 pathway, to treat, prevent and/or delay the development or progression of AMD. In some embodiments, an agent which inhibits VEGF-C is administered to a subject who is known to have (i.e., has been determined to have, e.g., by a method described herein) an above-normal level of VEGF-C. The VEGFR-2 inhibitor molecule and/or VEGFR-3 inhibitor molecule and/or VEGF-C inhibitor molecule is administered in an amount effective to treat, prevent, and/or delay the development or progression of AMD. In some embodiments, the VEGFR-2 inhibitor molecule and/or VEGFR-3 inhibitor molecule and/or VEGF-C inhibitor molecule is administered in an amount effective to reduce the subject's levels of VEGF-C to below a preselected value, e.g., a reference value that is associated with a lower risk category.

The invention also involves methods for treating eye disorders such as a maculopathy and pathogenic ocular neovascularization in a subject in need thereof, comprising administering to the subject a polypeptide comprising at least a first, a second and a third Ig-like domain of a wildtype VEGFR-3 amino acid sequence. In some embodiments, the eye disorder is age-related macular degeneration (AMD). In some embodiments, the polypeptide has an amino terminal residue selected from the group consisting of positions 1 to 47 of SEQ ID NO: 4, and a carboxy-terminal residue selected from the group consisting of positions 226 to 775 of SEQ ID NO: 4, wherein VEGFR-3 fragment binds at least one of VEGF-C and VEGF-D. In some embodiments, the polypeptide comprises the first through third Ig-like domains of VEGFR-3, and the polypeptide lacks Ig-like domains IV-VII of the VEGFR-3 amino acid sequence. In some variations, the polypeptide consists of, or consists essentially of, the first three Ig-like domains, fused to a heterologous peptide. In some embodiments, the portion of the polypeptide corresponding to VEGFR-3 is selected from the group consisting of defined by positions 1-226, positions 1-229, and positions 1-329, positions 47-224, positions 47-225, positions 47-226, positions 47-227, positions 47-228, positions 47-229, positions 47-230, positions 47-231, positions 47-232, positions 47-236, positions 47-240, positions 47-245, positions 47-314, positions 47-210, and positions 47-247 of SEQ ID NO: 4.

In an additional aspect, the invention provides packages including a VEGFR-2 inhibitor molecule and/or VEGFR-3 inhibitor molecule and/or VEGF-C inhibitor molecule, e.g., in a pharmaceutical composition, and instructions for administering the VEGFR-2 inhibitor molecule and/or VEGFR-3 inhibitor molecule and/or VEGF-C inhibitor molecule to a subject in order to treat, prevent, and/or delay the development or progression of AMD. In some embodiments, the VEGFR-2 inhibitor molecule and/or VEGFR-3 inhibitor molecule and/or VEGF-C inhibitor molecule is in a therapeutic composition also including a pharmacologically acceptable carrier. In some embodiments, the VEGFR-2 inhibitor molecule and/or VEGFR-3 inhibitor molecule and/or VEGF-C inhibitor molecule is in a form suitable for local delivery to the macular area.

In some variations, the invention is a system for identifying susceptibility to a maculopathy in a human subject. For example, in one variation, the system includes tools for performing at least one step, preferably two or more steps, and in some aspects all steps of a method of the invention, where the tools are operably linked to each other. Exemplary tools include laboratory equipment or reagents for performing assays and computer systems for processing data, comparing data, and/or transforming one type of data (e.g., VEGF-C measurements) into another (e.g., a risk score). Operable linkage describes a linkage through which components can function with each other to perform their purpose, and may include, for example, linkage through a computer network and/or the internet.

In still a further aspect, the invention is any of the subject matter defined by original claims appended hereto, and incorporated herein the summary of invention section by reference.

The foregoing paragraphs are not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document. The invention includes, as an additional aspect, all embodiments of the invention narrower in scope in any way than the variations defined by specific paragraphs above. For example, where certain aspects of the invention that are described as a genus, it should be understood that every member of a genus is, individually, an aspect of the invention. Where protein therapy is described, embodiments involving polynucleotide therapy (using polynucleotides that encode the protein) are specifically contemplated, and the reverse also is true.

Although the applicant(s) invented the full scope of the invention described herein, the applicants do not intend to claim subject matter described in the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

DETAILED DESCRIPTION

Definitions

Figure 1:
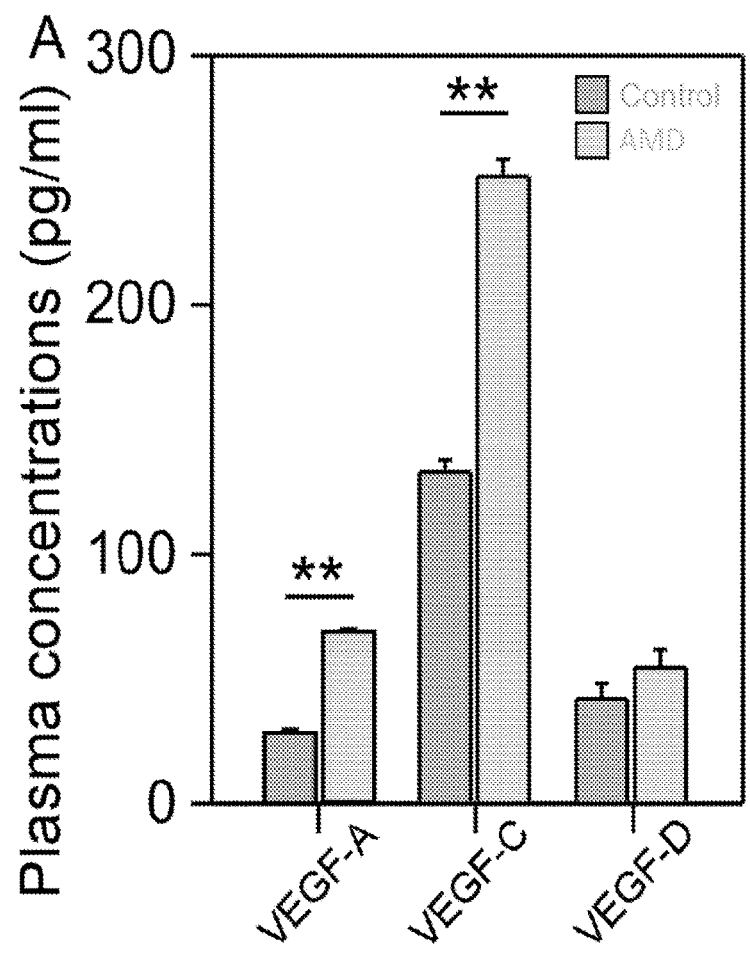
FIG. 1: Plasma concentrations of VEGF-A (n=142), VEGF-C (n=125) and VEGF-D (n=70) in control and AMD subjects.

As used herein, "age-related macular degeneration" or "AMD" includes both early, intermediate, and advanced AMD. Patients with early AMD are usually asymptomatic, and present clinically with yellowish drusen seen underneath the retinal pigment epithelium, with areas of mottled retinal pigment epithelium hyperpigmentation and hypopigmentation.

Patients usually develop rapid visual loss when neovascular AMD occurs. Typically, patients describe sudden worsening of central vision with distortion of straight lines (metamorphopsia) or a dark patch in their central vision (scotoma), or both. In geographic atrophy, there is slower progressive loss of vision over many years. Clinically, there is a sharply demarcated area of depigmentation showing retinal pigment epithelium atrophy. Neovascular AMD is characterised by subretinal or intraretinal fluid and haemorrhage; occasionally, the choroidal neovascularisation complex can be seen clinically. "Advanced AMD" includes both dry AMD and wet AMD (wet AMD is also referred to as neovascular AMD). Subjects with advanced AMD are those who can be categorized in Category 4 according to the AREDS classification.

Various AMD classification schemes have been developed. The Age-Related Eye Disease Study (AREDS) classified age-related macular degeneration into four categories as follows (AREDS Report No 8, Arch Ophthalmol, 2001, 119, 1417-36):

Category 1: None or a few small drusen (<63 μm in diameter).

Category 2: Any or all of the following: multiple small drusen, few intermediate drusen (63-124 μm in diameter), or retinal pigment epithelium abnormalities.

Category 3: Any or all of the following: extensive intermediate drusen, and at least one large drusen (≥125 μm in diameter, roughly equivalent to the size of the retinal vein at the rim of the optic disc), and geographic atrophy not involving the fovea.

Category 4: Geographic atrophy involving the fovea or any of the features of neovascular age-related macular degeneration, and visual loss presumed to be due to age-related macular degeneration. Although not part of this classification, advanced AMD might also include the involutional, atrophic stage of neovascular AMD that is not amenable to further treatment.

In the AREDS, the 5-year risk of developing advanced AMD in at least one eye in control participants was 1.3% in eyes in Category 2, 18.3% in those in Category 3, and 43.9% in those in Category 4.

Polypoidal choroidal vasculopathy is difficult to distinguish clinically from choroidal neovascularisation. Occasionally, orange, bulging dilatations might be visible under the retina. However, polypoidal choroidal vasculopathy more commonly presents with recurrent serous and haemorrhagic retinal pigment epithelium detachments. Retinal angiomatous proliferation is characterised clinically by signs of haemorrhage, oedema, and exudates within the retinal layers in addition to other typical signs of choroidal neovascularisation. In some cases, the anastomosis between the retinal and subretinal new vessels might be visible.

As used herein, a "subject" is a mammal, e.g., human, canine, feline, ovine, primate, equine, porcine, caprine, camelid, avian, bovine, and murine organisms. Typically, the subject is a human.

As used herein, "apparently healthy" means that a subject does not have clinical signs of AMD, e.g., is in AERDS Category 1, and is essentially free of current need for treatment. In other words, such subjects, if examined by a medical professional, would be characterized as healthy and generally free of symptoms of acute disease.

As used herein, a "risk factor" means a risk factor that is known to be associated with an increased risk of development or progression of AMD.

Within any given population, there is an absolute risk of developing a disease or trait, defined as the chance of a person developing the specific disease or trait over a specified time-period. For example, a woman's lifetime absolute risk of breast cancer is one in nine. That is to say, one woman in every nine will develop breast cancer at some point in their lives. Risk is typically measured by looking at very large numbers of people, rather than at a particular individual. Risk is often presented in terms of Absolute Risk (AR) and Relative Risk (RR). Relative Risk is used to compare risks associating with two variants or the risks of two different groups of people. For example, it can be used to compare a group of people with a an elevated level of a biomarker with another group having a "normal" level of the same biomarker. For a disease, a relative risk of 2 means that one group has twice the chance of developing a disease as the other group. The risk presented is usually the relative risk for a person, or a specific genotype of a person, compared to a matched population, such as a population with matched gender and ethnicity, with the understanding that ethnicity is usually as self-reported by a subject.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. Other features and advantages of the invention will be apparent from the following detailed description, and from the claims.

The results provided herein regarding the elevated levels of VEGF-C in subjects with AMD suggest that VEGF-C is a major driver of AMD. The results provided herein suggest that elevated VEGF-C levels can, independently of or dependently on other risk factors and/or biomarkers, be predictive of developing AMD, of AMD progression and of suitability of certain subjects for targeted therapy or clinical trials. The results provided herein suggest that monitoring VEGF-C levels can also be predictive of efficacy of a treatment, treatment regime or therapy. The information about VEGF-C levels as a biomarker does not duplicate, and is likely to be independent of the information provided by other known or presumed risk factors. Even when numerous other known risk factors are controlled for, VEGF-C measurement as a biomarker improves prediction. Furthermore, using an AMD biomarker as an assay for AMD risk can provide a simpler method of evaluating a subject's risk that does not require information about a subject's personal medical history.

The results presented herein suggest that elevated VEGF-C levels are associated with development and/or progression of AMD. Anti-VEGF-C agents or agents which inhibit the biological pathway of VEGF-C, i.e. inhibitors of the VEGFR-2 and/or VEGFR-3 pathways, may have a role in slowing the progression to advanced AMD, with VEGF-C levels providing a biomarker to provide a method of identifying people for whom these agents would be more or less effective.

The results presented herein suggest that anti-VEGF-C agents or agents which inhibit the biological pathway of VEGF-C, i.e. inhibitors of the VEGFR-2 and/or VEGFR-3 pathways, may have a role in preventing and/or treating AMD, with VEGF-C levels providing a biomarker to provide a method of identifying people for whom these agents would be more or less effective.

The findings described herein demonstrate that angiogenesis is associated with the pathogenesis of AMD. It is believed that VEGF-A, a key molecule in driving angiogenesis, is associated with the pathogenesis of AMD. As a result, there are several anti-VEGF-A products approved for treatment of AMD. These include Lucentis™ (an antibody fragment targeting VEGF-A) and Eylea™ (a soluble VEGFR-1/VEGFR-2 trap). Both Lucentis™ and Eylea™ target and bind to VEGF-A (but not to VEGF-C). Avastin™, the full length antibody version of Lucentis™ is also used in off-label treatment of AMD. The findings described herein demonstrate that angiogenesis associated with AMD pathogenesis may not just involve VEGF-A. Elevated levels of VEGF-C, a molecule also associated with driving angiogenesis, also appears to be associated with AMD development and progression.

The measuring of VEGF-C can occur at any one or more of the following time points: prior to an AMD diagnosis being made (e.g. in apparently healthy subjects), after a diagnosis of AMD has been made (e.g. in a screening or selection for potential targeted therapy), prior to initiation of a standard of care treatment, treatment regime or therapy for AMD, during treatment for AMD with a standard of care therapy or a targeted treatment, treatment regime or therapy, or after a course of treatment, treatment regime of therapy has been completed (e.g. to monitor for relapse). In some embodiments, the measuring of VEGF-C occurs after a subject with AMD does not respond to anti-angiogenic therapies, including standard of care anti-angiogenic therapies. For example, the measuring of VEGF-C occurs after a subject with AMD does not respond to, stops responding to or becomes less responsive to treatment with a standard of care anti-angiogenic agent such as, for example, Lucentis™, Avastin™ or Eylea™. These embodiments are not mutually exclusive. A subject undergoing AMD therapy can be monitored for VEGF-C expression to identify a time point at which VEGF-C becomes elevated. If the subject is already being treated with an anti-angiogenic standard of care therapy targeting VEGF-A and/or the VEGFR-1 and/or VEGFR-2 pathways (e.g. Lucentis™, Avastin™ or Eylea™), the subject may benefit from treatment with a VEGFR-3 inhibitor molecule that inhibits the action of VEGF-C such as, for example, a VEGF-C antibody, a VEGFR-3 antibody or a soluble VEGFR-3 trap. Alternatively, if the subject is not being treated with an anti-angiogenic standard of care therapy targeting VEGF-A and/or the VEGFR-1 and/or VEGFR-2 pathways, the subject may benefit from treatment with a standard of care anti-angiogenic agents or an agent that more specifically inhibits the action of VEGF-C such as, for example, a VEGF-C antibody, a VEGFR-3 antibody or a soluble VEGFR-3 trap. In the methods of prevention and treatment of AMD described herein, a combination of a standard of care anti-angiogenics for AMD (e.g. Lucentis™, Avastin™ or Eylea™) and a VEGFR-3 inhibitor molecule (e.g. a VEGF-C antibody, a VEGFR-3 antibody or a soluble VEGFR-3 trap) is envisaged. Such a combination anti-angiogenic therapy may provide significant benefits to the patient.

VEGF-C (SEQ ID NOs: 1 and 2) is originally expressed as a larger precursor protein, prepro-VEGF-C, having extensive amino- and carboxy-terminal peptide sequences flanking a VHD, with the C-terminal peptide containing tandemly repeated cysteine residues in a motif typical of Balbiani ring 3 protein. The prepro-VEGF-C polypeptide is processed in multiple stages to produce a mature and most active VEGF-C polypeptide (ΔNΔC VEGF-C) of about 21-23 kD (as assessed by SDS-PAGE under reducing conditions). Such processing includes cleavage of a signal peptide (approximately residues 1-31 of SEQ ID NO: 2); cleavage of a carboxyl-terminal peptide (approximately residues 228-419 of SEQ ID NO: 2) to produce a partially-processed form of about 29 kD; and cleavage (apparently extracellularly) of an amino-terminal peptide (approximately residues 32-102 of SEQ ID NO: 2) to produce a fully-processed mature form of about 21-23 kD (approximately residues 103-227 of SEQ ID NO: 2). Experimental evidence demonstrates that partially-processed forms of VEGF-C (e.g., the 29 kD form) are able to bind the Flt4 (VEGFR-3) receptor, whereas high affinity binding to VEGFR-2 occurs only with the fully processed forms of VEGF-C. Moreover, it has been demonstrated that amino acids 103-227 of SEQ ID NO: 2 are not all critical for maintaining VEGF-C functions. For example, a polypeptide consisting of amino acids 112-215 (and lacking residues 103-111 and 216-227) of SEQ ID NO: 2 retains the ability to bind and stimulate VEGF-C receptors. The cysteine residue at position 156 has been shown to be important for VEGFR-2 binding ability. It appears that VEGF-C polypeptides naturally associate as non-disulfide linked dimers.

A level of VEGF-C as a biomarker in a subject can be obtained by any art recognized methods. Typically, the level is obtained by measuring the level of VEGF-C in a sample including a body fluid, for example, blood, lymph, saliva, urine and the like. In a preferred embodiment, a level of VEGF-C is measured in a blood sample. In a preferred embodiment, a level of VEGF-C is measured in plasma.

In some embodiments, the methods described herein are practiced through the detection of a VEGF-C protein. In general, methods for detecting a VEGF-C protein can comprise contacting a biological sample with a compound that binds to and forms a complex with the polypeptide for a period sufficient to form the complex, and detecting the complex, so that if a complex is detected, a polypeptide of the invention is detected. The level of VEGF-C can be determined by immunoassays, e.g., enzyme-linked immunoassays (EIA) or enzyme-linked immunosorbent assays (ELISA); particle agglutination or flocculation tests (e.g., rapid latex agglutination); laser and rate nephelometry; turbidometry; or other known techniques for determining the presence and/or quantity of the marker. VEGF-C protein detection can be accomplished using antibodies specific for the protein in any of a number of formats commonly used by those of skill in the art for such detection. In some embodiments, the compound is a polypeptide comprising an ECD fragment of VEGFR-3 that binds VEGF-C.

For example, the production and characterization of monoclonal antibodies specific for VEGF-C is described in U.S. Pat. Nos. 7,109,308; 7,208,582; 7,402,312; 7,423,125; 7,576,189 and 7,850,963, the disclosures of which are incorporated herein by reference in their entireties. Such antibodies may be employed in ELISA-based techniques and Western blotting techniques to detect the presence of VEGF-C in a biological sample from a subject being tested. Methods for setting up ELISA assays and preparing Western blots of a sample are well known to those of skill in the art. The biological sample can be any tissue or fluid as described herein. In some variations, the tissue of fluid is from the eye, including the back of the eye; in some variations, the tissue or fluid is systemic, such as blood or serum/plasma.

In one embodiment, the antibodies or fragments can be utilized in enzyme immunoassays, wherein the subject antibody or fragment, or second antibodies, are conjugated to an enzyme. When a biological sample comprising a VEGF-C protein is combined with the subject antibodies, binding occurs between the antibodies and the VEGF-C protein. In one embodiment, a biological sample containing cells expressing a mammalian VEGF-C protein, or biological fluid containing secreted VEGF-C is combined with the subject antibodies, and binding occurs between the antibodies and the VEGF-C protein present in the biological sample comprising an epitope recognized by the antibody. This bound protein can be separated from unbound reagents and the presence of the antibody-enzyme conjugate specifically bound to the VEGF-C protein can be determined, for example, by contacting the sample with a substrate of the enzyme which produces a color or other detectable change when acted on by the enzyme. In another embodiment, the subject antibodies can be unlabeled, and a second, labeled antibody can be added which recognizes the subject antibody.

Examples of suitable protein assay kits include those based on Luminex technology (i.e. which use the Luminex analysers) and microbead capture such as the BioPlex™ kits available from BioRad.

The methods can include obtaining a level of VEGF-C in a subject by sending one or more samples of the subject biological sample (e.g. body fluid) to a laboratory, e.g., a commercial laboratory, for measurement of levels. In some embodiments, the methods include measuring the level of the biomarker in a body fluid from a subject, and providing information regarding the level of the biomarker, e.g., to the subject or a caregiver, e.g., a clinical entity such as a physician, nurse, hospital, clinical practice, or third-party payor, e.g., an insurance company.

Assaying VEGF-C by immunohistochemistry (IHC) requires at least one anti-VEGF-C antibody. Using standard approaches the anti-VEGF-C antibody can be used to detect the presence of VEGF-C protein in tissue samples obtained from the subject, including paraffin-embedded and frozen tumor sections. Typically, the tissue sections are initially treated in such a way as to retrieve the antigenic structure of proteins that were fixed in the initial process of collecting and preserving the tumor material. Slides are then blocked to prevent non-specific binding by the anti-VEGF-C detection antibody. The presence of VEGF-C protein is then detected by binding of the VEGF-C antibody to the VEGF-C protein. The detection antibody is linked to an enzyme, either directly or indirectly, e.g., through a secondary antibody that specifically recognizes the detection antibody. Typically, the tissue sections are washed and blocked with non-specific protein such as bovine serum albumin (BSA) between steps. The slide is developed using an appropriate enzyme substrate to produce a visible signal, and the samples are then counterstained with hematoxylin.

Similarly, the present invention also relates to a method of detecting and/or quantitating expression of a mammalian VEGF-C protein or a portion of the VEGF-C protein by a cell, in which a composition comprising a cell or fraction thereof (e.g., a soluble fraction) is contacted with an antibody or functional fragment thereof which binds to a mammalian VEGF-C protein or a portion of the VEGF-C protein under conditions appropriate for binding of the antibody or fragment thereto, and binding is monitored. Detection of the antibody, indicative of the formation of a complex between antibody and or a portion of the protein, indicates the presence of the protein.

The method can be used to detect expression of VEGF-C in a biological sample of a mammalian subject (e.g., in a sample, such as a body fluid, such as blood, saliva or other suitable sample). The level of expression of VEGF-C in a biological sample of that subject can also be determined, for instance, by flow cytometry, and the level of expression (e.g., staining intensity) can be correlated with disease susceptibility, progression or risk.

In certain other embodiments, VEGF-C polynucleotides such as mRNA encoding a mammalian VEGF-C protein may be measured. In general, methods for detecting VEGF-C mRNA can comprise contacting a biological sample with a compound that binds to and forms a complex with VEGF-C mRNA for a period sufficient to form the complex, and detecting the complex in a quantitative or semi-quantitative way. Such methods can also comprise amplification techniques involving contacting a biological sample with nucleic acid primers that anneal to VEGF-C mRNA or its complement, and amplifying annealed polynucleotides, so that if a polynucleotide is amplified, a VEGF-C polynucleotide is detected.

In the amplification procedures, polynucleotide sequences encoding a VEGF-C protein may be used in hybridization or PCR assays of fluids or tissues from biopsies to detect VEGF-C protein expression. Such methods may be qualitative or quantitative in nature and may include Southern or northern analysis, dot blot or other membrane-based technologies; PCR technologies; dip stick, pin, chip and ELISA technologies. All of these techniques are well known in the art and are the basis of many commercially available diagnostic kits.

One such procedure known in the art is quantitative real-time PCR. Real-time quantitative PCR can be conveniently accomplished using the commercially available ABI PRISM® 7700 Sequence Detection System, available from PE-Applied Biosystems, Foster City, Calif. and used according to manufacturer's instructions. PCR reagents can be obtained from PE-Applied Biosystems, Foster City, Calif. Gene target quantities obtained by real time RT-PCR may be normalized using either the expression level of GAPDH, a gene whose expression is constant, or by quantifying total RNA using RiboGreenT™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent from Molecular Probes. Methods of RNA quantification by RiboGreen™ are taught in Jones et al. (1998). Controls are analyzed in parallel to verify the absence of DNA in the RNA preparation (−RT control) as well as the absence of primer dimers in control samples lacking template RNA. In addition, RT-PCR products may be analyzed by gel electrophoresis.

A reverse transcriptase PCR (RT-PCR) amplification procedure may be performed in order to quantify the amount of mRNA amplified. Methods of reverse transcribing RNA into cDNA are well known and described in Sambrook et al. (1989). Alternative methods for reverse transcription utilize thermostable DNA polymerases. These methods are described in WO 90/07641, filed Dec. 21, 1990.

Conditions for incubating a nucleic acid probe or antibody with a test sample vary. Incubation conditions depend on the format employed in the assay, the detection methods employed, and the type and nature of the nucleic acid probe or antibody used in the assay. One skilled in the art will recognize that any one of the commonly available hybridization, amplification or immunological assay formats can readily be adapted to employ the nucleic acid probes or antibodies of the present invention. Examples of such assays can be found in Chard (1986); Bullock et al., (1982, 1983 and 1985); and Tijssen (1985). The tests of the present invention include cells, protein extracts of cells, or biological fluids such as, blood, serum, and plasma. The test sample used in the above-described method will vary based on the assay format, nature of the detection method and the tissues, cells or extracts used as the sample to be assayed. Methods for preparing protein extracts or membrane extracts of cells are well known in the art and can be readily adapted in order to obtain a sample which is compatible with the system utilized.

In addition, such assays may be useful in evaluating the efficacy of a particular therapeutic treatment regime in animal studies, in clinical trials, or in monitoring the treatment of an individual patient.

The screening methods described herein may optionally comprise the step of prescribing for or administering to the subject identified as having elevated VEGF-C expression in the biological sample a composition comprising a molecule that inhibits the VEGFR-2 and/or VEGFR-3 pathway, preferably the VEGFR-3 pathway. By "prescribing" is meant providing an order or authorization for the therapy, which may be dispensed to the subject for self-administration and/or administered by a medical professional that is difference from the prescribing professional. In some variations, the subject receives (is administered or self-administered) the therapy following the prescribing.

To assess the relative level of VEGF-C (mRNA or protein) expression, the level of VEGF-C expression in a biological sample can be subjected to one or more of various comparisons. In general, it can be compared to: (a) VEGF-C mRNA or protein expression levels in a collection of comparable biological samples from subjects with AMD; (b) VEGF-C mRNA or protein expression levels in a collection of biological samples from healthy subjects; or (c) VEGF-C mRNA or protein expression levels in an arbitrary standard.

In some variations, to provide a basis for the identification of patients at risk of developing AMD or at risk of their AMD progressing or to identify patients likely to benefit from a targeted therapy for AMD, VEGF-C measurements from multiple individuals are obtained, both healthy individuals and individuals with AMD, to establish a data set of VEGF-C mRNA or protein expression. With an established data set a variety of standard statistical analyses can be performed to identify when a measurement of VEGF-C is elevated, e.g., in a statistically significant manner relative to a healthy control. To assess the relative level of VEGF-C expression, the level of VEGF-C expression in a biological sample from a subject with AMD can be subjected to one or more of various comparisons. In general, it can be compared to: (a) VEGF-C mRNA or protein expression level(s) in comparable biological samples from healthy subjects; or (b) VEGF-C mRNA or protein expression level in an arbitrary standard. In some embodiments, a VEGF-C measurement of at least 1.0, 1.5, 2.0, 2.5 or at least 3.0 standard deviation(s) greater than a median VEGF-C measurement in corresponding healthy tissue is scored as elevated VEGF-C expression. In other embodiments, a VEGF-C measurement that is statistically significantly greater than VEGF-C measurements in corresponding healthy tissue, with a p-value less than 0.1, or less than 0.05, or less than 0.01, or less than 0.005, or less than 0.001 is scored as elevated VEGF-C expression. As a data set enlarges, the comparison can be refined by stratifying the data for additional variables, such as the age, sex, ethnicity, body mass, smoking habits or other factors that differentiate subjects.

In some embodiments, the screening methods described herein comprise comparing VEGF-C expression in the biological sample of an individual subject with a previous VEGF-C expression in the same subject, wherein elevated VEGF-C expression in the subsequent measurement identifies the subject as a subject for whom targeted AMD therapy will have efficacy.

In some embodiments, the methods described herein also include comparing the level of VEGF-C for the subject with a reference. The reference can take a variety of forms. It can be a single predetermined "cut-off" (threshold) value or concentration of VEGF-C, such as a median or mean, that has been determined from observations to represent an elevated measure of VEGF-C that (when equalled or exceeded) is predictive of the risk of development or progression of AMD in a subject or is predictive of the suitability of a subject for a clinical trial or is predictive of the suitability of a subject to be treated for AMD by use of particular treatments or therapies. It can be established based upon comparative groups, such as where the risk in one defined group is higher than, e.g., double, the risk in another defined group. It can be a range, for example, where the tested population is divided equally (or unequally) into groups, such as a low-risk group, a medium-risk group, and a high-risk group, or into quintiles (fifths), quartiles (quarters), or tertiles (thirds), the lowest group being subjects with the lowest risk and the highest being subjects with the highest risk.

The reference can depend upon the particular population selected. For example, an apparently healthy, non-smoker population (no detectable disease and no prior history of AMD) can have a different "normal" range of markers of VEGF-C than a smoking population, or a population the members of which have some stage of AMD. Accordingly, the reference selected may take into account the category in which a subject falls. Appropriate ranges and categories can be selected with no more than routine experimentation by those of ordinary skill in the art. In some embodiments, the reference is a predetermined value.

Determination of a suitable cut-off is made using, e.g., statistical analysis of VEGF-C protein or mRNA concentration data collected from multiple healthy and/or AMD patients (including subjects in whom VEGF-C has been measured and for whom targeted therapy based on the VEGF-C biomarker measurement has been employed and monitored for efficacy). If a "cut-off" value is employed, the cut-off concentration preferably is statistically determined to have optimal discriminating value for subjects who benefit from the targeted therapy (e.g., to have maximum sensitivity and specificity). It will be appreciated that statistical analysis of a dataset will permit clinicians to make informed decisions based on concentrations other than the optimal discriminating concentration (e.g., above or below the optimal discriminating concentration). For example, using receiver-operating-characteristic curves, or using other statistical summaries of VEGF-C concentration and treatment outcome data collected according to the invention, the practitioner is capable of selecting a cut-off VEGF-C concentration having a desired level of sensitivity or specificity for predicting efficacy of targeted therapy. Considerations regarding the probability of success of targeted therapy based on VEGF-C measurement, versus the probability of success of alternative therapies based on any available clinical data, can guide the selection of an appropriate cut-off concentration of VEGF-C for making a treatment decision.

The identifying, monitoring or selecting step of the screening or diagnostic methods described herein optionally comprises comparing the measurement of VEGF-C to a reference or control measurement of VEGF-C, and scoring the VEGF-C measurement from the sample as elevated, lowered (e.g. during targeted therapy) or normal based on statistical analysis or a ratio relative to the reference or control measurement. In some embodiments, the reference or control measurement comprises at least one of the following; (a) a database containing multiple VEGF-C measurements from healthy subjects and/or AMD subjects in biological samples of the same type (e.g. blood, tissue etc.); or (b) a reference value calculated from multiple VEGF-C measurements from healthy subjects and/or subjects with AMD, optionally further including statistical distribution information for the multiple measurements, such as standard deviation.

In some embodiments, a VEGF-C measurement of at least 1.0 standard deviation greater than a median VEGF-C measurement in corresponding healthy subjects is scored as elevated VEGF-C expression. In other embodiments, a VEGF-C measurement that is statistically significantly greater than VEGF-C measurements in corresponding healthy subjects, with a p-value less than 0.1, or less than 0.05, or less than 0.01, or less than 0.005, or less than 0.001 is scored as elevated VEGF-C expression.

Preferred methods for measuring VEGF-C employ an agent that binds VEGF-C with great specificity and binding affinity, to permit measurements of VEGF-C that are typically in the picogram per mL range. Although exemplified with antibodies, other suitable binding reagents exist and can be used to practice the invention.

For example, in some embodiments, VEGFR-2 and/or VEGFR-3 is used to measure the amount of VEGF-C in a sample. In such embodiments, the methods described herein comprises contacting the biological sample with VEGFR-2 and/or VEGFR-3 (or fragments thereof that bind to VEGF-C) and measuring the amount of bound VEGFR-2 and/or VEGFR-3. VEGFR-2 and VEGFR-3 are receptor tyrosine kinases that bind VEGF-C and the ligand-binding portions of the extracellular domain have been well characterized (U.S. Pat. No. 7,422,741 and International Patent Publication No. WO 2005/087808, the disclosures of which are incorporated herein by reference in their entireties). Although both receptors bind VEGF-C with high affinity, they also bind VEGF-D, a factor to consider in assay design.

Thus, if VEGFR-2/VEGFR-3 is used as a capture moiety, then the sample can be pre-treated to remove VEGF-D or probed with a detection antibody that is specific for the VEGF-C.

Elevated levels of VEGF-C in a sample indicate an increased risk of developing AMD or of AMD progression or an increased likelihood that the subject will benefit from a targeted therapy for AMD comprising use of a VEGFR-2 inhibitor molecule and/or a VEGFR-3 inhibitor molecule, for example, a VEGF-A antibody (e.g. Avastin™; Lucentis™), a VEGF-C antibody, a soluble VEGFR-2 trap (e.g. Eylea™), a soluble VEGFR-3 trap (e.g. VGX-300) or a VEGFR-3 antibody.

Also provided are novel kits or assays that are specific for, and have appropriate sensitivity with respect to, biomarker references selected on the basis of the present invention. In some embodiments, therefore, the kits or assays would differ from those presently commercially available, by including, for example, different cut-offs, and/or different sensitivities at particular cut-offs as well as instructions or other printed material for characterizing risk of developing AMD or progressing to advanced AMD, based upon the outcome of the assay.

In one embodiment, the use of VEGF-C measurement as a predictive, selective or responsive/tracking biomarker is independent of other predictors or biomarkers for AMD. Prediction, selection, response or tracking based on VEGF-C measurement may be additive with one or more other biomarkers (genetic or biological) or risk factors known to be associated with AMD, and does not simply duplicate the information derivable from evaluating those other biomarkers or risk factors.

Rick factors and other biomarkers for AMD will be known to the skilled person in the art and include for example those described in Kuo et al. (2013, Expert Rev. Ophthalmol., 8(2), 127), Sharma et al. (2012, DNA & Cell Biology, 31(11), 1618), Lim et al. (2012, The Lancet, 379, 1728), Ross et al. (2007, Expert Rev. Ophthalmol., 2(3), 443) and WO 2005/083430 (Massachusetts Eye & Ear Infirmary).

Risk factors for AMD include, for example, smoking, obesity, poor body mass index, fat intake, antioxidant vitamin and mineral intake, low dietary intake of vitamins A, C and E, and zinc, low dietary intake of lutein and omega-3 fatty acids, age, sex, family history of AMD, and physical exercise levels.

Other biomarkers for AMD include genetic biomarkers, inflammatory biomarkers, nutrient biomarkers and other biomarkers. Examples of reported genetic biomarkers for AMD include CFH (complement factor H; chr 1), ABCA4 (ATP-binding cassette transporter; chr 1), COL8A1 (collagen type 8 alpha 1 subunit; chr 3), CF1 (complement factor 1; chr 4), VEGF-A (vascular endothelial growth factor A; chr 6), FRK/COL10A1 (fyn-related kinase/alpha chain of type X collagen; chr 6), CFB (complement factor B [properdin]; chr 6), C2 (complement component 2; chr 6), ARMS2/HTRA1 (HtrA-serinepeptidase1; chr 10), LIPC (hepatic lipase; chr 15), CETP (cholesterylester transfer protein; chr 16), APOE (apolipoprotein E; chr 19), EECC6 (excision repair cross-complementing rodent repair deficiency, complementation group 6), C3 (complement component 3; chr 19), TIMP3 (tissue inhibitor of metalloproteinase 3; chr 22), and TNFRSF10A (tumour necrosis factor receptor superfamily 10a; chr 8).

Various immunological molecules and inflammatory mediators have been identified at the site of AMD lesions. Examples of reported inflammatory biomarkers for AMD include markers of systemic inflammation such as, for example, CRP (C-reactive protein), cytokines, TNF-R2 (tissue necrosis factor alpha receptor-II and cellular adhesion molecules (CAMs). Cytokines include the human interleukins. In particular, IL-6 has been reported as a biomarker for AMD. Other reported inflammatory biomarkers of AMD include fibrinogen and VEGF-A.

Various nutrients have been reported in the literature as having demonstrated risk reduction for AMD after supplementation. Several nutrients have shown promise and been reported as potential biomarkers. These include, for example, omega-3 fatty acids, various vitamins including vitamins A, D and E (α-tocopherol) and xanthophylls (e.g. lutein and zeaxanthin).

Other reported biomarkers for AMD include homocysteine levels, von Willebrand factors, and plasma leptin levels.

In another embodiment, the use of VEGF-C measurement as a predictive, selective or responsive/tracking biomarker is dependent on combining the VEGF-C measurement (or a "risk" or "benefit" value associated with the VEGF-C measurement) as a factor in combination with one or more other risk factors for AMD and/or measured values of another biomarker for AMD. Prediction, selection or responsiveness/tracking based may be based on a multifactorial evaluation in which the VEGF-C measurement (or value associated with the measured level) is combined with at least one other biomarker or risk factor level or value. For example, VEGF-C levels may be used in combination with other factors such as, for example, smoking, obesity, body mass index, fat intake, antioxidant vitamin and mineral intake, age, sex, family history of AMD, and physical exercise levels, inter alia. In another example, VEGF-C levels may be used in combination with another biomarker such as, for example, VEGF-A levels. Standard multivariate statistical analysis tools are used to optimize the predictive value of VEGF-C in combination with one or more of these additional biomarkers and/or risk factors.

The study described herein evaluated systemic biomarkers, in a large and well-characterized population of subjects with and without maculopathy from two geographical areas in the United States. Standardized collection of risk factor information including direct measurements of blood pressure and body mass index, as well as classification of maculopathy by means of standardized ophthalmological examinations and fundus photography, was employed.

Also provided herein are methods for evaluating the likelihood that a subject will benefit from treatment with a VEGFR-2 inhibitor molecule and/or a VEGFR-3 inhibitor molecule for reducing risk of development or progression of AMD. The method includes determining the level of VEGF-C in the subject; if the level of VEGF-C is high, then the subject is likely to benefit from the administration of a VEGFR-2 inhibitor molecule and/or a VEGFR-3 inhibitor molecule.

The methods described herein can also be used to evaluate the efficacy of a treatment for reducing the risk of development or progression of AMD. For example, the method can include determining the level of VEGF-C before, concurrently with, and/or after the administration of the treatment. In some embodiments, the subject receives multiple treatments, e.g., a treatment is administered in multiple doses, e.g., one or more doses per day for one or more days, weeks, months, or years, and the level of VEGF-C is determined, e.g., before any treatment, and after one or more treatments. In some embodiments, the treatment is the administration of a VEGF-A antibody, a VEGF-C antibody, a VEGFR-3 antibody, a soluble VEGFR-2 trap or a soluble VEGFR-3 trap or a combination of two or more, preferably no more than two, of these. In some embodiments, the methods described herein are performed as part of a clinical trial of a treatment to reduce the risk of the development or progression of AMD. These methods have important implications for subject treatment and also for clinical development of new therapeutics. Physicians typically select therapeutic regimens for subject treatment based upon the expected net benefit to the subject. The net benefit is derived from the risk to benefit ratio. The present methods permit selection of subjects who are more likely to benefit by intervention, thereby aiding the physician in selecting a therapeutic regimen. This might include using drugs with a higher risk profile where the likelihood of expected benefit has increased. Likewise, clinical investigators may desire to select for clinical trials a population with a high or low likelihood of obtaining a net benefit with a particular protocol. The methods described herein can be used by clinical investigators to select such a population. Thus, in some embodiments, the methods provide entry criteria and methods for selecting subjects for clinical trials, e.g., trials of AMD therapeutics, by selecting subjects having a given level of VEGF-C biomarker, having a level that is above or below a reference.

Anti-angiogenic agents which can be used in methods of treatment or treatment steps described herein include, e.g., anecortave acetate (Alcon), which reduces production of matrix metalloproteinase, a key agent in the growth of neovascular membranes; or an agent that inhibits vascular endothelial growth factor A (VEGF-A). A number of inhibitors of VEGF-A signalling are known in the art and can include, e.g., ZD6474 (Tuccillo et al., Clin Cancer Res. 2005 Feb. 1; 11(3): 1268-76); COX-2, Tie2 receptor, angiopoietin, and neuropilin inhibitors; pigment epithelium-derived factor (PEDF), endostatin, and angiostatin (21-25); VEGF-A inhibitory aptamers, e.g., Macugen™ (pegaptanib, Pfizer); antibodies or fragments thereof, e.g., VEGF-A antibodies, e.g., bevacizumab (Avastin™, Genentech), or fragments thereof, e.g., ranibizumab (Lucentis™, Genetech); soluble fms-like tyrosine kinase 1 (sFlt1) polypeptides or polynucleotides (Harris et al., Clin Cancer Res. 2001 July; 7(7):1992-7; U.S. Pat. No. 5,861,484); PTK787/ZK222 584 (Maier et al., Graefes Arch Clin Exp Ophthalmol. 2005 Jan. 14; KRN633 (Maier et al., Mol Cancer Ther. 2004 December; 3(12):1639-49); VEGF-Trap™ (Eylea™, Regeneron); intravitreal steroids, e.g., triamcinolone; and Alpha2-antiplasmin (Matsuno et al, Blood 2003; 120:3621-3628). For reviews of VEGF-A and its inhibitors, see, e.g., Campochiaro, Ocular neovascularisation and excessive vascular permeability, Expert Opin Biol Ther. 2004 September; 4(9): 1395-402; Ferrara, Vascular Endothelial Growth Factor: Basic Science and Clinical Progress, Endocr. Rev., Aug. 1, 2004; 25(4): 581-611; and Verheul and Pinedo, Vascular endothelial growth factor and its inhibitors, Drugs Today (Bare). 2003; 39 Suppl C:81-93.

The term "VEGFR-2 inhibitor molecule" as used herein refers to any molecule that acts with specificity to reduce VEGF-C/VEGFR-2, VEGF-D/VEGFR-2 or VEGF-A/VEGFR-2 interactions, e.g., by blocking VEGF-C or VEGF-D binding to VEGFR-2, by blocking VEGF-A binding to VEGFR-2 or by reducing expression of VEGFR-2. In one embodiment, the VEGFR-2 inhibitor inhibits VEGF-C and VEGF-D binding to VEGFR-2. In another embodiment, the VEGFR-2 inhibitor inhibits binding of VEGF-A to VEGFR-2. The VEGFR-2 inhibitor can be a polypeptide comprising a soluble VEGFR-2 ECD fragment (amino acids 20-764 of human VEGFR-2, whose sequence is set forth in UniProtKB/Swiss-Prot accession no. P35968) that binds VEGF-A or VEGF-C or VEGF-D; VEGFR-2 antisense polynucleotides or short-interfering RNA (siRNA); anti-VEGFR-2 antibodies; a VEGFR-2 inhibitor polypeptide comprising an antigen-binding fragment of an anti-VEGFR-2 antibody that inhibits binding between VEGFR-2 and VEGF or VEGF-C or VEGF-D; an aptamer that inhibits binding between VEGFR-2 and VEGF-A; an aptamer that inhibits binding between VEGFR-2 and VEGF-C; an aptamer that inhibits binding between VEGFR-2 and VEGF-D; or a fusion protein comprising the soluble VEGFR-2 polypeptide fragment fused to an immunoglobulin constant region fragment (Fc). In some embodiments, a VEGFR-2 polypeptide fragment is fused to alkaline phosphatase (AP).

In other embodiments, the molecule that inhibits the VEGFR-2 pathways is, bevacizumab (Avastin™, Genentech), or fragments thereof, e.g., ranibizumab (Lucentis™ Genetech) or Soluble VEGFR1/2 trap (VEGF-Trap™ (Eylea™, Regeneron)).

The term "VEGFR-3 inhibitor molecule" as used herein refers to any molecule that reduces the interaction of VEGF-C and/or VEGF-D with VEGFR-3 and includes, but is not limited to, an antibody that binds VEGF-C and inhibits VEGF-C stimulation of VEGFR-3; or a fragment of said antibody that retains the inhibitory activity; an antibody that binds VEGFR-3 and inhibits VEGF-C stimulation of VEGFR-3; or a fragment of said antibody that retains the inhibitory activity; a polypeptide that comprises a VEGFR-3 ECD fragment that binds VEGF-C and inhibits VEGF-C stimulation of VEGFR-3 (WO 2005/087808, the disclosure of which is incorporated by reference in its entirety); an antisense or interfering nucleic acid (e.g., antisense oligonucleotide; micro-RNA, short interfering RNA) that inhibits VEGF-C expression; an antisense or interfering nucleic acid that inhibits VEGFR-3 expression; and a polypeptide that comprises a VEGFR-2 ECD fragment that binds VEGF-C and inhibits VEGF-C stimulation of VEGFR-3.

The term "VEGF-C inhibitor molecule" as used herein refers to any molecule that reduces the interaction of VEGF-C with VEGFR-2 and/or VEGFR-3 and includes, but is not limited to, an antibody that binds VEGF-C and inhibits VEGF-C stimulation of VEGFR-3; or a fragment of said antibody that retains the inhibitory activity; an antibody that binds VEGFR-3 and inhibits VEGF-C stimulation of VEGFR-3; or a fragment of said antibody that retains the inhibitory activity; an antibody that binds VEGFR-2 and inhibits VEGF-C stimulation of VEGFR-2; or a fragment of said antibody that retains the inhibitory activity; a polypeptide that comprises a VEGFR-2 or VEGFR-3 ECD fragment that binds VEGF-C and inhibits VEGF-C stimulation of VEGFR-2 or VEGFR-3 (WO 2005/087808, the disclosure of which is incorporated by reference in its entirety); an antisense or interfering nucleic acid (e.g., antisense oligonucleotide; micro-RNA, short interfering RNA) that inhibits VEGF-C expression; an antisense or interfering nucleic acid that inhibits VEGFR-3 expression; and a polypeptide that comprises a VEGFR-2 ECD fragment that binds VEGF-C and inhibits VEGF-C stimulation of VEGFR-3.

In a similar fashion, the term "VEGF-A inhibitor molecule" as used herein refers to any molecule that reduces the interaction of VEGF-A with VEGFR-1 or VEGFR-2 (especially VEGFR-2), and includes, but is not limited to, an antibody that binds VEGF-A and inhibits VEGF-A stimulation of its receptors; an antibody that binds the receptor(s) and inhibits ligand-mediated stimulation of the receptor(s); antibody fragments; soluble extracellular domain fragments of the receptor(s) that bind VEGF-A, including domain swap fusions of receptors; and the like.

In some embodiments, a VEGFR-3 ECD receptor fragment comprises at least the first three Ig-like domains of the receptor. Soluble receptors capable of binding VEGF-C and VEGF-D, thereby inhibiting VEGF-C or VEGF-D activity or signaling via VEGFR-3, are also disclosed in WO2000/023565, WO2000/021560, WO2002/060950 and WO2005/087808, the disclosures of which are incorporated herein by reference in their entireties. Those soluble receptors, optionally modified with the ΔN2 sequon change described below and optionally other modifications described herein, are contemplated as aspects of the invention.

Table 1 defines approximate boundaries of the Ig-like domains for human VEGFR-3. These boundaries are significant as the boundaries chosen can be used to form ligand binding molecules, and so can influence the binding properties of the resulting constructs. It will be appreciated that a construct containing two (or more adjacent Ig-like domains preferably will include most or all of the amino acids that naturally occur between the include domains.

TABLE 1

Immunoglobulin-like domains for human VEGFR-3

|    | VEGFR-3<br>SEQ ID NO: 3 positions | VEGFR-3<br>SEQ ID NO: 4 positions |
|----|-----------------------------------|-----------------------------------|
| D1 | 158-364                           | 47-115                            |
| D2 | 479-649                           | 154-210                           |
| D3 | 761-961                           | 248-314                           |
| D4 | 1070-1228                         | 351-403                           |
| D5 | 1340-1633                         | 441-538                           |
| D6 | 1739-1990                         | 574-657                           |
| D7 | 2102-2275                         | 695-752                           |

The complete ECD extends to about position 775 of SEQ ID NO: 4.

Soluble receptor constructs for use as a VEGFR-3 ECD fragment comprise at least one Ig-like domain of VEGFR-3 as described in Table 1, to as many as seven. The ligand binding molecule optionally will include sequence before the most N-terminally positioned Ig-like domain, optionally will include sequence beyond the most C-terminally Ig-like domain, and optionally will include sequence between the Ig-like domains as well. Variants, e.g., with one or more amino acid substitutions, additions, or deletions of an amino acid residue, are also contemplated. In some embodiments, the ligand binding molecule comprises a fragment of human VEGFR-3 comprising at least the first three Ig-like domains of human VEGFR-3.

In some embodiments, the VEGFR-3 ECD fragment comprises Ig-like domains I-III of VEGFR-3 (referred to herein as "VGX-300") as described in Makinen et al., Nat. Med., 7:199-205 and International Publication Nos. WO2000/023565, WO2000/021560, WO2002/060950 and WO2005/087808, the disclosures of which are incorporated herein by reference in their entireties. In exemplary embodiments, the VEGFR-3 ECD fragment comprises a portion of a human VEGFR-3 ECD, wherein the portion binds to one or both of human VEGF-C and human VEGF-D, and comprises at least the first, second and third Ig-like domains of the VEGFR-3 ECD and preferably polypeptide lacks VEGFR-3 Ig-like domains 4-7 and preferably any transmembrane domain and preferably any intracellular domain.

In some embodiments, VEGFR-3 ECD fragments are contemplated in which the soluble receptor polypeptide comprises an amino acid sequence at least 90, 91, 92, 93, 94, or 95% identical to a VEGFR-3 fragment, wherein the VEGFR-3 fragment comprises an amino acid sequence consisting of a portion of SEQ ID NO: 4, wherein the carboxy-terminal residue of the fragment is selected from the group consisting of positions 211 to 247 of SEQ ID NO: 4, and wherein the fragment and the polypeptide bind VEGF-C or VEGF-D. In some variations, the fragment has an amino terminal amino acid selected from the group consisting of positions of 1 to 47 of SEQ ID NO: 4. In some variations, the VEGFR-3 fragment used to make the soluble receptor has an amino terminal residue selected from the group consisting of positions 1 to 47 of SEQ ID NO: 4, and a carboxy-terminal residue selected from the group consisting of positions 226 to 775 of SEQ ID NO: 4, wherein VEGFR-3 fragment binds at least one of VEGF-C and VEGF-D. Specific peptides include a fragment of VEGFR-3 defined by positions 1-226, positions 1-229, and positions 1-329, positions 47-224, positions 47-225, positions 47-226, positions 47-227, positions 47-228, positions 47-229, positions 47-230, positions 47-231, positions 47-232, positions 47-236, positions 47-240, positions 47-245, positions 47-314, positions 47-210, and positions 47-247 of SEQ ID NO: 4.

In some embodiments, the amino acid sequence of the ECD fragment of VEGFR-3 is modified from wildtype VEGFR-3 to eliminate the second putative N-linked glycosylation sequon of wildtype VEGFR-3, and wherein the polypeptide lacks VEGFR-3 Ig-like domains 4-7 and preferably any transmembrane domain and preferably any intracellular domain.

In some embodiments, the VEGFR-3 ECD fragment comprises a modified VEGFR-3 ECD fragment (referred to as VGX-301ΔN2) as described in International Patent Application Nos.: PCT/AU2014/000161 and PCT/AU2014/000114, the disclosures of which are incorporated herein by reference with respect to their teachings of the VGX-300N2 polypeptide, variations thereof and combination therapies comprising the VGX-300N2 polypeptide. For example, in some embodiments, the VEGFR-3 ECD fragment is a polypeptide that comprises a portion of a human VEGFR-3 ECD, wherein the portion binds to human VEGF-C and comprises at least the first, second and third Ig-like domains of the VEGFR-3 ECD. In some embodiments, wherein the amino acid sequence of the ECD fragment of VEGFR-3 is modified from wildtype VEGFR-3 to eliminate the second putative N-linked glycosylation sequon of wildtype VEGFR-3, and wherein the polypeptide lacks VEGFR-3 Ig-like domains 4-7 and preferably any transmembrane domain and preferably any intracellular domain.

In some embodiments, the VEGFR-3 ECD fragment comprises a polypeptide similar or identical in amino acid sequence to a human VEGFR-3 polypeptide (SEQ ID NO: 4) or fragment thereof, with the proviso that positions of the VEGFR-3 ECD fragment corresponding to positions 104-106 of the human VEGFR-3 polypeptide set forth in SEQ ID NO: 4 are not identical to N-X-S or N-X-T, wherein the VEGFR-3 ECD fragment binds human VEGF-C. The fragment minimally comprises enough of the VEGFR-3 sequence to bind the ligand, and may comprise the complete receptor. Extracellular domain fragments are preferred. Preferred polypeptides have an amino acid sequence at least 80% identical to a ligand binding fragment thereof. Fragments that are more similar, e.g., 85%, 90%, 91%, 92%, 93%, 94%, 95%, 96%, 97%, 98%, 99%, 99.5%, or 100% are highly preferred. Fragments that are 35%, 40%, 45%, 50%, 55%, 60%, 65%, 70%, and 75% are also contemplated. A genus of similar polypeptides can alternatively be defined by the ability of encoding polynucleotides to hybridize to the complement of a nucleotide sequence that corresponds to the cDNA sequence encoding the VEGFR-3 receptor.

In some embodiments, the VEGFR-3 ECD fragment comprises a polypeptide comprising a fragment of human VEGFR-3 (SEQ ID NO: 4) selected from the group consisting of positions 1-226 or 25-226 of SEQ ID NO: 4, positions 1-229 or 25-229 of SEQ ID NO: 4 and positions 1-329 or 25-229 of SEQ ID NO: 4, with the proviso that positions 104-106 of SEQ ID NO: 4 are not identical to N-X-S or N-X-T. In some embodiments, the VEGFR-3 ECD fragment is a polypeptide comprising a fragment of human VEGFR-3 (SEQ ID NO: 4) selected from the group consisting of positions 47-224 of SEQ ID NO: 4, positions 47-225 of SEQ ID NO: 4, positions 47-226 of SEQ ID NO: 4, positions 47-227 of SEQ ID NO: 4, positions 47-228 of SEQ ID NO: 4, positions 47-229 of SEQ ID NO: 4, positions 47-230 of SEQ ID NO: 4, positions 47-231 of SEQ ID NO: 4, positions 47-232 of SEQ ID NO: 4, positions 47-236 of SEQ ID NO: 4, positions 47-240 of SEQ ID NO: 4, and positions 47-245 of SEQ ID NO: 4, with the proviso that positions 104-106 of the encoded ligand binding fragment of VEGFR-3 are not identical to N-X-S or N-X-T. In some embodiments, the VEGFR-3 ECD fragment is a polypeptide comprising a fragment of human VEGFR-3 (SEQ ID NO: 4), selected from the group consisting of positions 47-314 of SEQ ID NO: 4, positions 47-210 of SEQ ID NO: 4, and positions 47-247 of SEQ ID NO: 4, with the proviso that positions 104-106 of SEQ ID NO: 4 are not identical to N-X-S or N-X-T.

In some embodiments, the VEGFR-3 ECD fragment is operably linked to an immunoglobulin or a portion of an immunoglobulin as the fusion partner. In this embodiment, the VEGFR-3 ECD fragment is operably linked to all or a portion of an immunoglobulin, particularly a human immunoglobulin, even more particularly the Fc portion of a human immunoglobulin. Such fusion proteins can be prepared by transfecting cells with DNA encoding VEGFR-3 subunit:Fc fusion protein and expressing the dimers in the same cells. In a particular embodiment, the ligand binding polypeptides are the same on each monomer subunit (i.e the dimer is a homodimer). Methods for making immunoglobulin fusion proteins are well known in the art, such as the ones described in Hollenbaugh and Aruffo ("Construction of Immunoglobulin Fusion Proteins", in Current Protocols in Immunology, Suppl. 4, pages 10.19.1-10.19.11, 1992) or WO 01/03737, for example, both incorporated herein by reference.

In some embodiments, the VEGFR-3 ECD fragment comprises an amino acid sequence that is similar or identical to the amino acid sequence set forth in SEQ ID NO: 5. In some embodiments, the VEGFR-3 ECD fragment comprises an amino acid sequence comprising amino acids 22-290 or 23-290 of SEQ ID NO: 5. In some embodiments, the ligand binding molecule comprises amino acids 22-537 or 23-537 of SEQ ID NO: 5 or amino acids 1-537 of SEQ ID NO: 5.

In some embodiments, the molecule comprises short interfering RNA (siRNA) that inhibits VEGF-C expression. RNA interference of the VEGF family of proteins and receptors is described in U.S. Patent application Publication Nos.: 2006/0217332, 2006/0025370, 2005/0233998, 2005/0222066 and 2005/0171039, the disclosure of which are incorporated herein by reference in their entireties. Interfering RNA directed to VEGF or VEGFR family members is described in U.S. Patent Publication No. 2006/0217332, incorporated herein by reference.

In some embodiments, the molecule comprises a zinc finger protein that inhibits VEGF-C expression.

Exemplary VEGFR-3 antibodies and their production are described in U.S. Pat. Nos. 6,107,046 and 6,824,777; U.S. Patent Publication Nos. 2006/0269548 and 2006/0177901; and International Patent Application No. PCT/FI95/00337 (WO 95/33772), all incorporated herein by reference in their entireties.

Exemplary VEGF-C antibodies are described, for example, in International Patent Application Nos. PCT/FI1996/000427 (WO/1997/005250) and PCT/US1998/001973 (WO/1998/033917); and U.S. Patent Publication Nos. 2004/0147726, 2005/0232921, 2005/0192429, 2005/0059117, 2005/0282228, 2003/0176674, and 2006/0121025, 2006/0030000, and U.S. Pat. No. 6,403,088 all incorporated herein by reference.

Exemplary VEGFR antibodies and other inhibitor compounds are described, for example, in U.S. Pat. Nos. 7,056,509; 7,052,693; 6,986,890; 6,897,294; 6,887,468; 6,878,720; 6,344,339; 5,955,311; 5,874,542; and 5,840,301, all incorporated herein by reference.

Any chemical substance that can be safely administered as a therapeutic and that can be used to modulate biochemical pathway targets identified herein, such as VEGF-A mediated stimulation of VEGF receptors, may be used to practice the invention. Small molecules that inhibit the interaction between VEGF-C and/or VEGFR-3 with VEGFR-3 are specifically contemplated. VEGF-C/VEGF-D inhibitors are disclosed in U.S. Pat. No. 7,045,133, incorporated herein by reference.

That patent describes, for example, monomeric monocyclic peptide inhibitors based on loop 1, 2 or 3 of VEGF-D. A preferred peptide interferes with at least the activity of VEGF-D and VEGF-C mediated by VEGF receptor-2 and VEGF receptor-3 (VEGFR-3). A particularly preferred peptide interferes with the activity of VEGF-D, VEGF-C and VEGF mediated by VEGFR-2 and the activity of VEGF-D and VEGF-C mediated by VEGFR-3. The patent also describes a dimeric bicyclic peptide inhibitor which comprises two monomeric monocyclic peptides, each individually based on loop 1, 2 or 3 of VEGF-D, linked together. Such dimeric bicyclic peptides may comprise two monomeric monocyclic peptides which are the same or different. (See, for example, Table 1-3 of the '133 patent.)

The VEGF receptors are receptor tyrosine kinases and intracellular signaling is initiated through receptor phosphorylation. Accordingly, one preferred class of molecules for practice of the invention is tyrosine kinase inhibitors, including those described in and Morn, Oncogene, 19(56):6574-83, 2000, incorporated herein by reference. VEGFR-3 inhibitors are disclosed in U.S. Patent Publication No. 2002-0164667, incorporated herein by reference.

In another embodiment, the methods described herein optionally further comprise administering a tyrosine kinase inhibitor that inhibits VEGFR-2 and/or VEGFR-3 activity.

Exemplary tyrosine kinase inhibitors for use in the methods described herein include, but are not limited to, AEE788 (TKI, VEGFR-2, EGFR: Novartis); ZD6474 (TKI, VEGFR-1, -2, -3, EGFR: Zactima: AstraZeneca); AZD2171 (TKI, VEGFR-1, -2: AstraZeneca); SU 11248 (TKI, VEGFR-1, -2, PDGFR: Sunitinib: Pfizer); AG13925 (TKI, VEGFR-1, -2:

Pfizer); AG013736 (TKI, VEGFR-1, -2: Pfizer); CEP-7055 (TKI, VEGFR-1, -2, -3: Cephalon); CP-547,632 (TKI, VEGFR-1, -2: Pfizer); GW7S6024 (TKL VEGFR-1, -2, -3: GlaxoSmithKline); GW786034 (TKI, VEGFR-1, -2, -3: GlaxoSmithKline); sorafenib (TKI, Bay 43-9006, VEGFR-1, -2, PDGFR: Bayer/Onyx); SU4312 (TKI, VEGFR-2, PDGFR: Pfizer); AMG706 (TKI, VEGFR-1, -2, -3: Amgen); XL647 (TKI, EGFR, HER2, VEGFR, ErbB4: Exelixis); XL999 (TK1, FGFR, VEGFR, PDGFR, Fll-3: Exelixis); PKC412 (TKI, KIT, PDGFR, PKC, FLT3, VEGFR-2: Novartis); AEE788 (TKI, EGFR, VEGFR2, VEGFR-1: Novartis): OSI-030 (TKI, c-kil, VEGFR: OSI Pharmaceuticals); OS1-817 (TKI c-kit, VEGFR: OSI Pharmaceuticals); DMPQ (TKI, ERGF, PDGFR, ErbB2. p56. pkA, pkC); MLN518 (TKI, Flt3, PDGFR, c-KIT (T53518: Millennium Pharmaceuticals); lestaurinib (TKI, FLT3, CEP-701, Cephalon); ZD 1839 (TKI, EGFR: gefitinib, Iressa: AstraZeneca); OSI-774 (TKI, EGFR: Erlotininb: Tarceva: OSI Pharmaceuticals); lapatinib (TKI, ErbB-2, EGFR, and GD-2016: Tykerb: GlaxoSmithKline).

In some embodiments, the methods described herein further comprise administering a tyrosine kinase inhibitor that inhibits angiogenesis to the subject. Exemplary anti-angiogenic tyrosine kinases and their targets are provided below in Table 2.

TABLE 2

Antiangiogenic tyrosine kinase receptor inhibitors and their targets

| Agent | VEGFR-1 | VEGFR-2 | VEGFR-3 | PDGFR | EGFR | Other targets |
|---|---|---|---|---|---|---|
| Vandetanib | | • | | | • | RET |
| Sunitinib | | • | | • | | KIT, FLT3, RET |
| Axitinib | | • | • | | | |
| Sorafenib | | • | • | • | | KIT, RAF, FLT3 |
| Vatalanib | | • | • | • | | KIT |
| Cediranib | | • | • | • | | KIT |
| Motesanib | | • | • | • | | KIT, RET |
| Pazopanib | | • | • | • | | KIT |
| BIBF 1120 | | • | | • | | FGFR |

Abbreviations: FGFR, fibroblast-like growth factor receptor; FLT3, FMS-like tyrosine kinase 3; KIT, stem cell factor receptor; RET, glial cell line-derived neurotrophic factor receptor: VEGFR, vascular endothelial growth factor receptor.

In some embodiments, the methods described herein further comprise administering an inhibitor of the PI3/AKT/mTOR pathway. In some embodiments, the inhibitor is a PI3 kinase inhibitor selected from the group consisting of wortmannin (Calbiochem), 3-methyladenine (3-MA, Sigma), LY294002 (Calbiochem) and chloroquine.

In some embodiments, the inhibitor is a mTOR (mammalian target of rapamycin) inhibitor. Exemplary mTOR inhibitors include, but are not limited to, the following:

| Brand Name or Product # | Generic Name | Patent (U.S. Unless Specified) or Reference |
|---|---|---|
| Rapamune ® | rapamycin (sirolimus) | 3,929,992; 5,288,711; 5,516,781 |
| RAD001 (Certican ®) | everolimus; 40-O-(2-hydroxyethyl)-rapamycin | EP663916; U.S. Pat. Appl. 20030170287 |
| CCI-779 | Rapamycin 42-ester with 3-hydroxy-2-(hydroxymethyl)-2-methylpropionic acid | 6,617,333; 5,362,718; 6,277,983 |
| | Tumstatin and related polypeptides | U.S. Pat. Appl. 20030144481 |

-continued

| Brand Name or Product # | Generic Name | Patent (U.S. Unless Specified) or Reference |
|---|---|---|
| ABT578 | | U.S. Pat. Appl. 20030073737 |
| "rapalogs," e.g., AP23573, AP22594 | | U.S. Pat. Appl. 20030073737; WO01/02441; WO01/14387 |
| AP23841 | | ARIAD Pharmaceuticals |
| TAFA93 | | Isotechnika |

In addition to rapamycin and those derivatives of rapamycin listed in the above table those discussed in U.S. Pat. Appl. No. 20030170287 may also be used. See also WO 94/09010, and WO 96/41807. Rapamycin derivatives may also include without limitation "rapalogs," e.g., as disclosed in WO 98/02441 and WO01/14387; deuterated rapamycin analogs, e.g., as disclosed in U.S. Pat. No. 6,503,921. Derivatives of other mTOR inhibitors are also contemplated.

Other compounds that may be administered in combination with the VEGFR-2 inhibitors or VEGFR-3 inhibitors described herein include, but are not limited to, the compounds provided below in Table 1.

TABLE 1

| Product | Target or Mechanism of Action | Comments |
|---|---|---|
| VEGF-A Inhibitors | | |
| KH902 | VEGF-A inhibitor | VEGF-Receptor-Fc Recombinant fusion protein with ligand binding domain taken from VEGFR-1 and VEGFR-2 that binds all VEGF-A isoforms and PlGF but not VEGF-C or -D |
| VEGF-A DARPin (AGN-150998) | VEGF-A inhibitor | Derived from ankyrin protein with selective binding to VEGF-A and not other members of the VEGF family. |
| ESBA1008 | Single chain antibody fragment to VEGF-A | |

TABLE 1-continued

| Product | Target or Mechanism of Action | Comments |
|---|---|---|
| *Anti-Pericyte (PDGF-B Inhibitors)* | | |
| E10030 | Anti-PDGF aptamer | Targets pericyte mediated resistance to anti-VEGF-A therapy. |
| *Multi-Targeted Kinase Inhibitors* | | |
| Vatalanib (PTK787/PTK/ZK) | Tyrosine kinase inhibitor | |
| AL-39324 | Tyrosine kinase inhibitor | Injectable. |
| Pazopanib | Tyrosine kinase inhibitor | TKI of VEGFR-1, VEGFR-2, VEGFR-3, PDGFR-a/b and cKit. Topical eye drop application. |
| TG100801 | Tyrosine kinase inhibitor | Prodrug inhibits VEGF, PDGF, FGF receptors and Src family of kinases. Topical administration. |
| Squalamine | Small molecule aminosterol binds calmodulin | Binds calmodulin and prevents modulation of VEGF, PDGF and bFGF. |
| *mTOR Pathway Inhibitors* | | |
| Sirolimus (DE-109) | mTOR inhibitor | Broad acting anti-proliferative and immune suppressive agent. |
| Sirolimus | mTOR inhibitor | |
| PF-655 (REDD14P) | Synthetic siRNA to RTP801 (mTOR regulator) | Stress induced mTOR inhibitor that stabilises TSC1-TSC2 inhibitory complex and enhances oxidative stress-dependent cell death. |
| Palomid529 | Small molecule TORC1/TORC2 inhibitor (mTOR pathway) | |
| *Vascular Disrupting Agents* | | |
| Zybrestat | VDA (vascular disrupting agent) and cadherin 5 inhibitor | |
| Fosbretabulin (combretastatin A4 phosphate) | Vascular disrupting agent (VDA) | |
| *Anti-Inflammatory Agents* | | |
| *Corticosteroids* | | |
| Posurdex/SK-0503 | Corticosteroid and VEGF-A inhibitor | |
| Iluvien (fluocinolone acetonide) | Corticosteroid (intravitreal insert) | |
| IBI-20089 | Slow release triamcinolone | |
| *Complement Inhibitors* | | |
| LFG316 | Anti-C5 (complement pathway) | Selectively targets inflammation associated with AMD |
| ARC1905 | Anti-C5 aptamer | |
| AL-78898A (POT-4) | Anti-C3 cyclic peptide | Targets C3 in the complement pathway. |
| *'Other' Anti-Inflammatory Agents* | | |
| Humira (adalimumab) | Anti-TNF mAb | |
| *Miscellaneous Targeted Agents* | | |
| iSONEP | Anti-S1P mAb | mAb targets the lipid sphingosine-1-phosphate |
| Ocriplasmin | Truncated form of Human serine protease plasmin | In development for vitreomacular adhesion in wet AMD patients |
| Volociximab | Chimeric Ab to a5b1 integrin | Blocks binding of a5b1 integrin to fibronectin involved in vascular stabilisation |
| hI-con1 | Anti-Tissue Factor | Chimeric, IgG-like homodimeric protein composed of a mutant factor VIIa domain fused to an effector region (IgG Fc). Mutant fV11 binds to tissue factor which is expressed on the luminal surface of pathologic cells including AMD lesions, triggering immune destruction of hI-con1 targeted cells via effector functions |
| ORA102 | Target unknown. | |
| *Gene Therapy* | | |
| rAAV.sFlt-1 | Adenovrial gene delivery of soluble form of VEGFR-1. | Sub-retinally delivered gene therapy. 'Traps' VEGFR-1 ligands only (VEGF-A, VEGF-B, PlGF). |
| adPEDF | Adenoviral gene delivery of Pigment epithelium derived factor (PEDF) | PEDF is anti-angiogenic (inhibits VEGF induced proliferation, EC migration and permeability). |
| RetinoStat | Lentiviral delivery of angiostatin & endostatin | Angiostatin (fragment of plasmin) and endostatin (C-term fragement of Type XVIII collagen) are endogenous inhibitors of angiogenesis. |
| AAV2-sFLT01 | Adenoviral gene delivery of soluble form of VEGFR-1 | Intravitreally delivered gene therapy. 'Traps' VEGFR-1 ligands only (VEGF-A, VEGF-B, PlGF) |
| *Antisense & siRNA* | | |
| GS-101 | Antisense targeting IRS-1 | Topical application of antisense to Insulin-Receptor-Substrate-1 |
| Bevasiranib | siRNA targeting VEGF | |
| AGN211745 | siRNA targeting VEGFR-1 | |

Other compounds that may be administered in combination with the VEGFR-2 inhibitors or VEGFR-3 inhibitors described herein include PDGF inhibitors. A PDGF Inhibitor Product inhibitor product may be administered in combination with one or more of the agents described herein for inhibiting binding between the VEGF family of proteins and VEGF receptors. In some embodiments, the inhibitor products are co-administered in a single composition. In other embodiments, the inhibitor products administered as separate compositions.

Exemplary PDGF inhibitors are also described in Table 1 above. Exemplary PDGF inhibitors include antibodies that bind to a PDGF protein (e.g., PDGF-A, -B, -C, and/or -D and/or homodimers or heterodimers thereof); antibodies that bind to a PDGF receptor (e.g., PDGF-α and/or PDGF-β and/or heterodimers or homodimers thereof); and PDGF ligand traps comprised of a soluble, ligand-binding extracellular domain fragment of either or both receptors, optionally fused to a heterologous protein such as an immunoglobulin constant domain.

The term "PDGF" refers to a platelet-derived growth factor that regulates cell growth or division. As used herein, the term "PDGF" includes the various subtypes of PDGF including PDGF-B, PDGF-A, PDGF-C, PDGF-D, variant forms thereof and dimerized forms thereof, including PDGF-AA, PDGF-AB, PDGF-BB, PDGF-CC, and PDGF-DD. Platelet derived growth factors includes homo- or heterodimers of A-chain (PDGF-A) and B-chain (PDGF-B) that exert their action via binding to and dimerization of two related receptor tyrosine kinase platelet-derived growth factor cell surface receptors (i.e., PDGFRs), PDGFR-α and PDGFR-β. In addition, PDGF-C and PDGF-D, two additional protease-activated ligands for the PDGFR complexes, have been identified (Li et al., (2000) *Nat. Cell. Biol.* 2: 302-9; Bergsten et al., (2001) *Nat. Cell. Biol.* 3: 512-6; and Uutele et al., (2001) *Circulation* 103: 2242-47). Due to the different ligand binding specificities of the PDGFRs, it is known that PDGFR-α/α binds PDGF-AA, PDGF-BB, PDGF-AB, and PDGF-CC; PDGFR-β/β binds PDGF-BB and PDGF-DD; whereas PDGFR-α/β binds PDGF-AB, PDGF-BB, PDGF-CC, and PDGF-DD (Betsholtz et al., (2001) *BioEssays* 23: 494-507). As used herein, the term "PDGF" also refers to those members of the class of growth factors that induce DNA synthesis and mitogenesis through the binding and activation of a PDGFR on a responsive cell type. PDGFs can effect, for example: directed cell migration (chemotaxis) and cell activation; phospholipase activation; increased phosphatidylinositol turnover and prostaglandin metabolism; stimulation of both collagen and collagenase synthesis by responsive cells; alteration of cellular metabolic activities, including matrix synthesis, cytokine production, and lipoprotein uptake; induction, indirectly, of a proliferative response in cells lacking PDGF receptors; and potent vasoconstrictor activity. The term "PDGF" can be used to refer to a "PDGF" polypeptide, a "PDGF" encoding gene or nucleic acid, or a dimerized form thereof.

The term "PDGF inhibitor product" refers to an agent that reduces, or inhibits, either partially or fully, the activity or production of a PDGF. A PDGF inhibitor product can directly or indirectly reduce or inhibit the activity or production of a specific PDGF such as PDGF-B. Furthermore, "PDGF inhibitor products" include agents that act on a PDGF ligand or its cognate receptor so as to reduce or inhibit a PDGF-associated receptor signal. Examples of "PDGF inhibitor products" include antisense molecules, ribozymes or RNAi that target a PDGF nucleic acid; PDGF aptamers, PDGF antibodies to PDGF itself or its receptor, or soluble PDGF receptor decoys that prevent binding of a PDGF to its cognate receptor; antisense molecules, ribozymes or RNAi that target a cognate PDGF receptor (PDGFR) nucleic acid; PDGFR aptamers or PDGFR antibodies that bind to a cognate PDGFR receptor; and PDGFR tyrosine kinase inhibitors.

In one embodiment, the PDGF inhibitor product is selected from: a compound of Formula A, B, C, D or E as described and defined is US 2012/0100136 (the entire contents of which are herein incorporated by reference), p1B3 antibody, CDP860, IMC-3G3, 162.62 antibody, 163.31 antibody, 169.14 antibody, 169.31 antibody, αR1 antibody, 2A1E2 antibody, M4TS.11 antibody, M4TS.22 antibody, Hyb 120.1.2.1.2 antibody, Hyb 121.6.1.1.1 antibody, Hyb 127.5.7.3.1 antibody, Hyb 127.8.2.2.2 antibody, Hyb 1.6.1 antibody, Hyb 1.11.1 antibody, Hyb 1.17.1 antibody, Hyb 1.18.1 antibody, Hyb 1.19.1 antibody, Hyb 1.23.1 antibody, Hyb 1.24 antibody, Hyb 1.25 antibody, Hyb 1.29 antibody, Hyb 1.33 antibody, Hyb 1.38 antibody, Hyb 1.39 antibody, Hyb 1.40 antibody, Hyb 1.45 antibody, Hyb 1.46 antibody, Hyb 1.48 antibody, Hyb 1.49 antibody, Hyb 1.51 antibody, Hyb 6.4.1 antibody, F3 antibody, Humanized F3 antibody, C1 antibody, Humanized C1 antibody, 6.4 antibody, anti-mPDGF-C goat IgG antibody, C3.1 antibody, PDGFR-B1 monoclonal antibody, PDGFR-B2 monoclonal antibody, 6D11 monoclonal antibody, Sis 1 monoclonal antibody, PR7212 monoclonal antibody, PR292 monoclonal antibody, HYB 9610 monoclonal antibody, HYB 9611 monoclonal antibody, HYB 9612 monoclonal antibody, or HYB 9613 monoclonal antibody, or a pharmaceutically acceptable salt thereof of any of any of the aforementioned.

In a preferred embodiment, one or more inhibitors of VEGF-A/VEGF-C//VEGF-D/VEGFR-2/VEGFR-3 described herein are administered in combination with a PDGFR-beta antibody (such as that being developed by Regeneron Inc. for ocular indications) or an anti-PDGF aptamer (such as E10030 being developed by Ophthotech Inc. for ocular indications).

In some embodiments, the VEGFR-2 inhibitor molecule and/or VEGFR-3 inhibitor molecule and/or VEGF-C inhibitor molecule is administered in conjunction with another modality for treating, preventing or delaying the development of AMD. A number of such treatments are known in the art, e.g., photodynamic therapy or laser photocoagulation to treat wet AMD, diet and exercise regiments, and or vitamin supplements, e.g., as described in AREDS Research Group, Arch Ophthalmol 2001:119, 1417-1436; Seddon et al, JAMA, 1994; 272: 1413-1420, and U.S. Pat. No. 6,660,297. In some embodiments, the methods include administering to the subject an anti-angiogenesis agent as described above.

Another aspect of the invention is a system that is capable of carrying out a part or all of a method of the invention, or carrying out a variation of a method of the invention as described herein in greater detail. Exemplary systems include, as one or more components, computing systems, environments, and/or configurations that may be suitable for use with the methods and include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like. In some variations, a system of the invention includes one or more machines used for analysis of biological material (e.g., genetic material), as described herein. In some variations, this analysis of the biological material involves a chemical analysis and/or a nucleic acid amplification.

Figure 11:
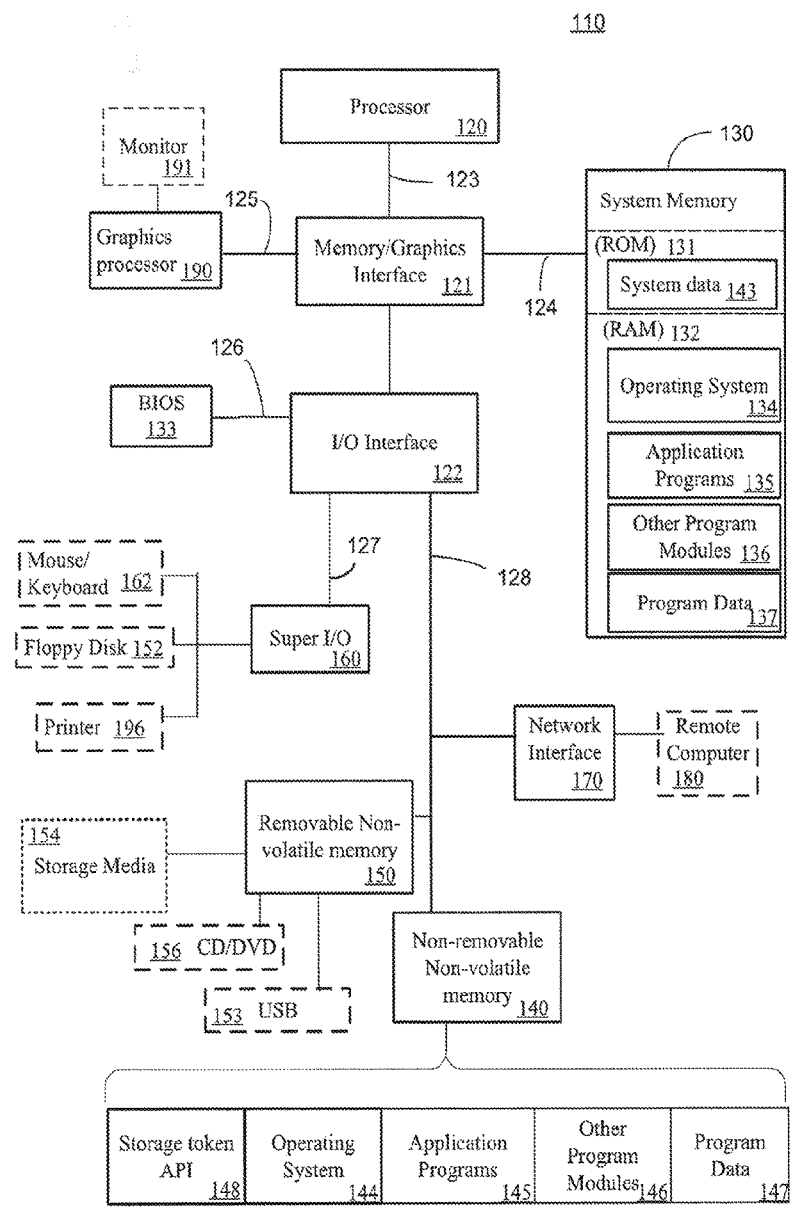
FIG. 11 is an exemplary system comprising exemplary computer components.

With reference to FIG. 11, an exemplary system of the invention, which may be used to implement one or more steps of methods of the invention, includes a computing device in the form of a computer 110. Components shown in dashed outline are not technically part of the computer 110, but are used to illustrate the exemplary embodiment of FIG. 11. Components of computer 110 may include, but are not limited to, a processor 120, a system memory 130, a memory/graphics interface 121, also known as a Northbridge chip, and an I/O interface 122, also known as a Southbridge chip. The system memory 130 and a graphics processor 190 may be coupled to the memory/graphics interface 121. A monitor 191 or other graphic output device may be coupled to the graphics processor 190.

A series of system busses may couple various system components including a high speed system bus 123 between the processor 120, the memory/graphics interface 121 and the I/O interface 122, a front-side bus 124 between the memory/graphics interface 121 and the system memory 130, and an advanced graphics processing (AGP) bus 125 between the memory/graphics interface 121 and the graphics processor 190. The system bus 123 may be any of several types of bus structures including, by way of example, and not limitation, such architectures include Industry Standard Architecture (ISA) bus, Micro Channel Architecture (MCA) bus and Enhanced ISA (EISA) bus. As system architectures evolve, other bus architectures and chip sets may be used but often generally follow this pattern. For example, companies such as Intel and AMD support the Intel Hub Architecture (IHA) and the Hypertransport™ architecture, respectively.

The computer 110 typically includes a variety of computer-readable media. Computer-readable media can be any available media that can be accessed by computer 110 and includes both volatile and nonvolatile media, removable and non-removable media. By way of example, and not limitation, computer readable media may comprise computer storage media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other physical medium which can be used to store the desired information and which can accessed by computer 110.

Figure 7:
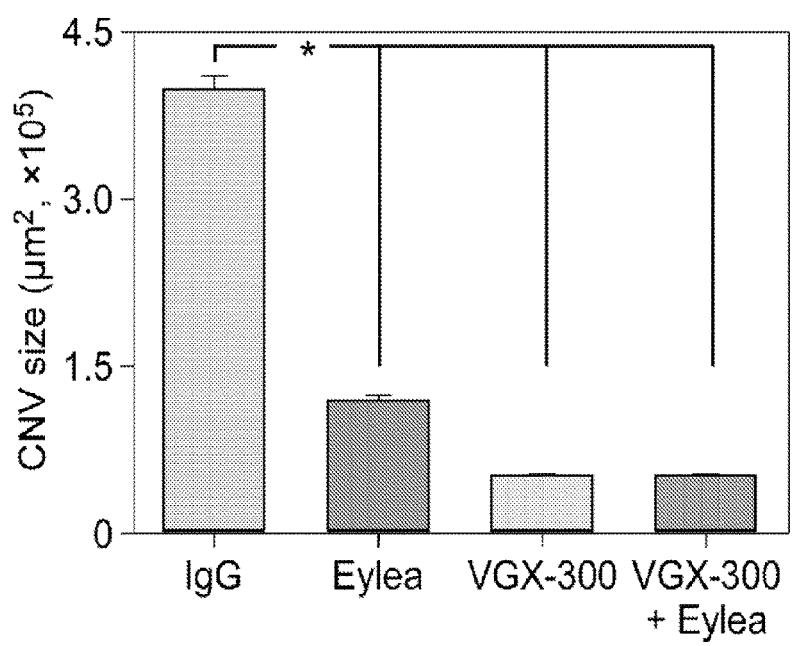
FIG. 7: Effects of treatment on CNV size. Mean size of laser-induced CNV membranes at day 14 post-laser injury

The system memory 130 includes computer storage media in the form of volatile and/or nonvolatile memory such as read only memory (ROM) 131 and random access memory (RAM) 132. The system ROM 131 may contain permanent system data 143, such as identifying and manufacturing information. In some embodiments, a basic input/output system (BIOS) may also be stored in system ROM 131. RAM 132 typically contains data and/or program modules that are immediately accessible to and/or presently being operated on by processor 120. By way of example, and not limitation, FIG. 7 illustrates operating system 134, application programs 135, other program modules 136, and program data 137.

The I/O interface 122 may couple the system bus 123 with a number of other busses 126, 127 and 128 that couple a variety of internal and external devices to the computer 110. A serial peripheral interface (SPI) bus 126 may connect to a basic input/output system (BIOS) memory 133 containing the basic routines that help to transfer information between elements within computer 110, such as during start-up.

A super input/output chip 160 may be used to connect to a number of 'legacy' peripherals, such as floppy disk 152, keyboard/mouse 162, and printer 196, as examples. The super I/O chip 160 may be connected to the I/O interface 122 with a bus 127, such as a low pin count (LPC) bus, in some embodiments. Various embodiments of the super I/O chip 160 are widely available in the commercial marketplace.

In one embodiment, bus 128 may be a Peripheral Component Interconnect (PCI) bus, or a variation thereof, may be used to connect higher speed peripherals to the I/O interface 122. A PCI bus may also be known as a Mezzanine bus. Variations of the PCI bus include the Peripheral Component Interconnect-Express (PCI-E) and the Peripheral Component Interconnect-Extended (PCI-X) busses, the former having a serial interface and the latter being a backward compatible parallel interface. In other embodiments, bus 128 may be an advanced technology attachment (ATA) bus, in the form of a serial ATA bus (SATA) or parallel ATA (PATA).

The computer 110 may also include other removable/non-removable, volatile/nonvolatile computer storage media. By way of example only, FIG. 7 illustrates a hard disk drive 140 that reads from or writes to non-removable, nonvolatile magnetic media. The hard disk drive 140 may be a conventional hard disk drive.

Removable media, such as a universal serial bus (USB) memory 153, firewire (IEEE 1394), or CD/DVD drive 156 may be connected to the PCI bus 128 directly or through an interface 150. A storage media 154 may coupled through interface 150. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. In some variations, the storage media is any non-transitory media, excluding, e.g., a signal.

The drives and their associated computer storage media discussed above and illustrated in FIG. 11, provide storage of computer readable instructions, data structures, program modules and other data for the computer 110. In FIG. 7, for example, hard disk drive 140 is illustrated as storing operating system 144, application programs 145, other program modules 146, and program data 147. Note that these components can either be the same as or different from operating system 134, application programs 135, other program modules 136, and program data 137. Operating system 144, application programs 145, other program modules 146, and program data 147 are given different numbers here to illustrate that, at a minimum, they are different copies. A user may enter commands and information into the computer 20 through input devices such as a mouse/keyboard 162 or other input device combination. Other input devices (not shown) may include a microphone, joystick, game pad, satellite dish, scanner, or the like. These and other input devices are often connected to the processor 120 through one of the I/O interface busses, such as the SPI 126, the LPC 127, or the PCI 128, but other busses may be used. In some embodiments, other devices may be coupled to parallel ports, infrared interfaces, game ports, and the like (not depicted), via the super I/O chip 160.

The computer 110 may operate in a networked environment using logical connections to one or more remote computers, such as a remote computer 180 via a network interface controller (NIC) 170. The remote computer 180 may be a personal computer, a server, a router, a network PC, a peer device or other common network node, and typically includes many or all of the elements described above relative to the computer 110. The logical connection between the NIC 170 and the remote computer 180 depicted in FIG. 11 may include a local area network (LAN), a wide area network (WAN), or both, but may also include other networks. Such networking environments are commonplace in offices, enterprise-wide computer networks, intranets, and the Internet. The remote computer 180 may also represent a web server supporting interactive sessions with the computer 110, or in the specific case of location-based applications may be a location server or an application server.

In some embodiments, the network interface may use a modem (not depicted) when a broadband connection is not available or is not used. It will be appreciated that the network connection shown is exemplary and other means of establishing a communications link between the computers may be used.

In some variations, the invention is a system for identifying susceptibility to a maculopathy, such as macular degeneration, or pathogenic ocular neovascularization, in a human subject. For example, in one variation, the system includes tools for performing at least one step, preferably two or more steps, and in some aspects all steps of a method of the invention, where the tools are operably linked to each other. Operable linkage describes a linkage through which components can function with each other to perform their purpose.

In some variations, a system of the invention is a system for assessing risk of a human subject for developing a disease or condition selected from a maculopathy and pathogenic ocular neovascularization, the system comprising:
  (a) at least one processor;
  (b) at least one computer-readable medium;
  (c) a database operatively coupled to a computer-readable medium of the system and containing population information correlating measurements of the disease or condition and VEGF-C measurements in a population of humans;
  (d) a measurement tool that receives an input about the human subject and generates information from the input about the measurement of VEGF-C in a biological sample from the human subject; and
  (e) an analysis tool or routine that:
    (i) is operatively coupled to the database and the measurement tool,
    (ii) is stored on a computer-readable medium of the system,
    (iii) is adapted to be executed on a processor of the system, to compare the information about the human subject with the population information in the database and generate a conclusion with respect to risk of the subject for developing the disease or condition.

Exemplary processors (processing units) include all variety of microprocessors and other processing units used in computing devices. Exemplary computer-readable media are described above. When two or more components of the system involve a processor or a computer-readable medium, the system generally can be created where a single processor and/or computer readable medium is dedicated to a single component of the system; or where two or more functions share a single processor and/or share a single computer readable medium, such that the system contains as few as one processor and/or one computer readable medium. In some variations, it is advantageous to use multiple processors or media, for example, where it is convenient to have components of the system at different locations. For instance, some components of a system may be located at a testing laboratory dedicated to laboratory or data analysis, whereas other components, including components (optional) for supplying input information or obtaining an output communication, may be located at a medical treatment or counseling facility (e.g., doctor's office, health clinic, HMO, pharmacist, geneticist, hospital) and/or at the home or business of the human subject (patient) for whom the testing service is performed.

Figure 12:
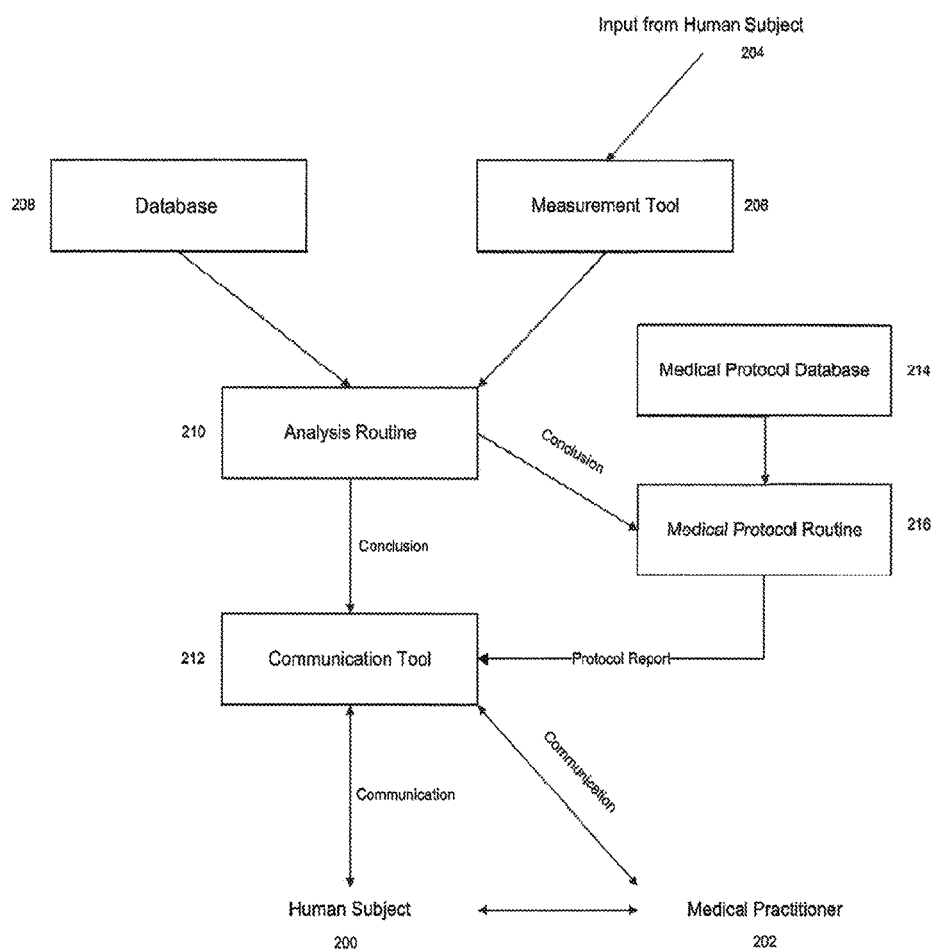
FIG. 12 is a flow chart depicting system components and operation.

Referring to FIG. 12 an exemplary system includes a database 208 that is operatively coupled to a computer-readable medium of the system and that contains population information correlating the measurement of VEGF-C and risk for developing the disease or condition in a population of humans.

In a simple variation, the database contains 208 data relating to the level of VEGF-C observed in a biological sample of a population of humans with the maculopathy and/or pathogenic ocular neovascularization and information about the level of VEGF-C observed in healthy subjects. Such data provides an indication as to the potential of developing maculopathy and/or pathogenic ocular neovascularization for a human subject that is identified as expressing an elevated level of VEGF-C. As the database becomes more populated with patient data, it become a more powerful statistical tool for comparing an input with respect to a subject and making a prediction as to metastatic potential. Such information includes, but is not limited to, information about parameters such as age, sex, ethnicity, race, medical history, weight, diabetes status, blood pressure, family history, smoking history, and alcohol use in humans and impact of the at least one parameter on the disease or condition. These more robust databases can be used by an analysis routine 210 to calculate a combined score with respect to potential for developing maculopathy and/or pathogenic ocular neovascularization for a human subject. In some variations, risk factors are combined using a multiplicative model. In some variations, logistic regression or other statistical tools are used to combine risk factors.

In addition to the database 208, the system further includes a measurement tool 206 programmed to receive an input 204 from or about the human subject and generate an output that contains information about the VEGF-C measurement. (The input 204 is not part of the system per se but is illustrated in the schematic FIG. 12.) Thus, the input 204 will contain a specimen or contain data from which a level of VEGF-C in a biological sample can be directly read, or analytically determined.

In another variation, the input 204 from the human subject contains data that is unannotated or insufficiently annotated with respect to VEGF-C, requiring analysis by the measurement tool 206. For example, the input can be raw data measurements from experiments designed to evaluate the level of VEGF-C in a biological sample. In such variations, the measurement tool 206 comprises a tool, preferably stored on a computer-readable medium of the system and adapted to be executed on a processor of the system, to receive a data input about a subject and determine information about the level of VEGF-C in the biological sample from the data. For example, the measurement tool 206 contains instructions, preferably executable on a processor of the system, for analyzing the unannotated input data and determining the level of VEGF-C of interest in the human subject.

In yet another variation, the input 204 from the human subject comprises a biological sample, such as a fluid (e.g., ocular fluid, blood, serum or plasma) or ocular tissue, blood vessel or lymphatic vessel tissue sample, that can be analyzed to determine the level of VEGF-C in the sample. In this variation, an exemplary measurement tool 206 includes laboratory equipment for processing and analyzing the sample to determine the level of VEGF-C in the biological sample of the human subject.

In some variations the measurement tool 206 includes: immunoassay reagents for measuring VEGF-C in the biological sample; and an analysis tool stored on a computer-readable medium of the system and adapted to be executed on a processor of the system, to determine the level of VEGF-C in the sample based on the immunoassay data.

In some variations, the measurement tool 206 further includes additional equipment and/or chemical reagents for processing the biological sample to purify VEGF-C from cells in a sample for further analysis using immunoassays, size separation tools, or other analytical equipment.

The exemplary system further includes an analysis tool or routine 210 that: is operatively coupled to the database 208 and operatively coupled to the measurement tool 206, is stored on a computer-readable medium of the system, is adapted to be executed on a processor of the system to compare the information about the human subject with the population information in the database 208 and generate a conclusion with respect to potential for developing maculopathy and/or pathogenic ocular neovascularization in the human subject. In simple terms, the analysis tool 210 looks at the level of VEGF-C identified by the measurement tool 206 for the human subject, and compares this information to the database 208, to determine potential for developing maculopathy and/or pathogenic ocular neovascularization in the subject. The susceptibility can be based on the single parameter (the level of VEGF-C), or can involve a calculation based on other genetic and non-genetic data, as described above, that is collected and included as part of the input 204 from the human subject, and that also is stored in the database 208 with respect to a population of other humans. Generally speaking, each parameter of interest is weighted to provide a conclusion with respect to the disease or condition. Such a conclusion is expressed in the conclusion in any statistically useful form, for example, as a relative risk, an odds ratio, a lifetime risk, or a probability that the subject will develop maculopathy and/or pathogenic ocular neovascularization.

Figure 13:
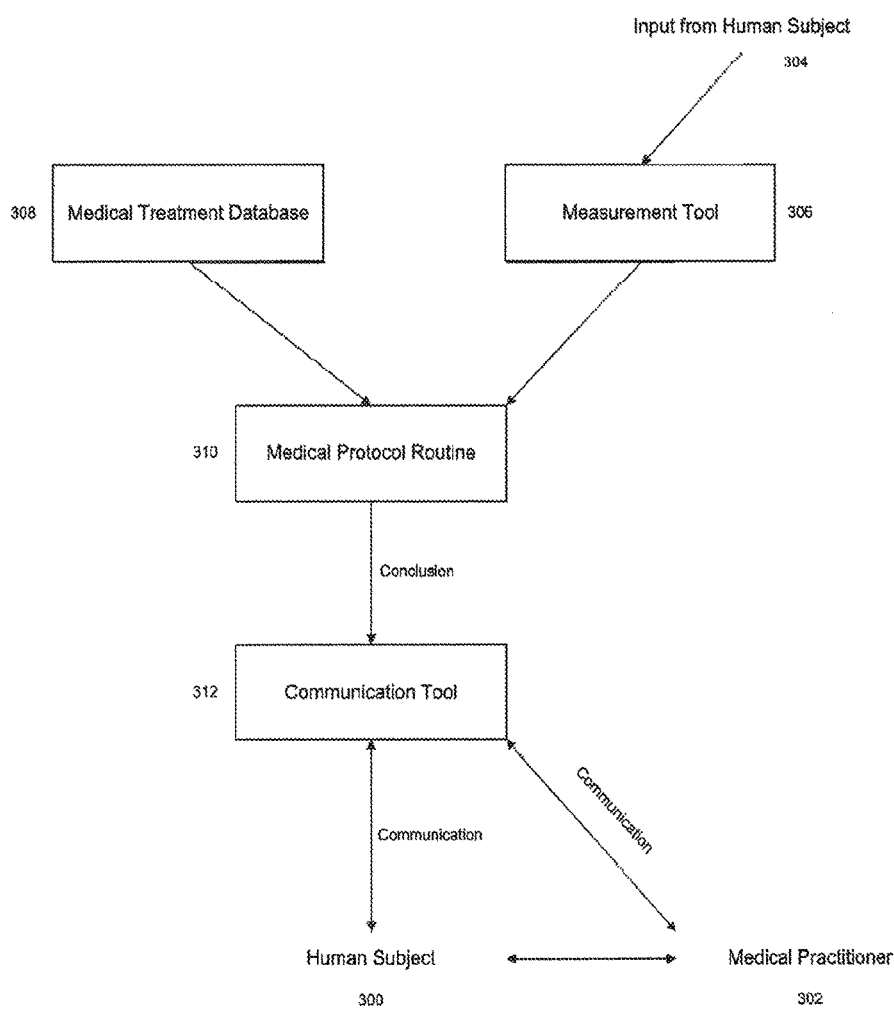
FIG. 13 is another flow chart depicting system components and operation.

In some variations, the system as just described further includes a communication tool 212. For example, the communication tool is operatively connected to the analysis routine 210 and comprises a routine stored on a computer-readable medium of the system and adapted to be executed on a processor of the system, to: generate a communication containing the conclusion; and to transmit the communication to the human subject 200 or the medical practitioner 202, and/or enable the subject or medical practitioner to access the communication. (The subject and medical practitioner are depicted in the schematic FIG. 13, but are not part of the system per se, though they may be considered users of the system. The communication tool 212 provides an interface for communicating to the subject, or to a medical practitioner for the subject (e.g., doctor, nurse, genetic counselor), the conclusion generated by the analysis tool 210 with respect to potential for developing maculopathy and/or pathogenic ocular neovascularization in the subject. Usually, if the communication is obtained by or delivered to the medical practitioner 202, the medical practitioner will share the communication with the human subject 200 and/or counsel the human subject about the medical significance of the communication. In some variations, the communication is provided in a tangible form, such as a printed report or report stored on a computer readable medium such as a flash drive or optical disk. In some variations, the communication is provided electronically with an output that is visible on a video display or audio output (e.g., speaker). In some variations, the communication is transmitted to the subject or the medical practitioner, e.g., electronically or through the mail. In some variations, the system is designed to permit the subject or medical practitioner to access the communication, e.g., by telephone or computer. For instance, the system may include software residing on a memory and executed by a processor of a computer used by the human subject or the medical practitioner, with which the subject or practitioner can access the communication, preferably securely, over the internet or other network connection. In some variations of the system, this computer will be located remotely from other components of the system, e.g., at a location of the human subject's or medical practitioner's choosing.

In some variations, the system as described (including embodiments with or without the communication tool) further includes components that add a treatment or prophylaxis utility to the system. For instance, value is added to a determination of a subject developing maculopathy and/or pathogenic ocular neovascularization when a medical practitioner can prescribe or administer a standard of care that can prevent or delay onset of the disease or condition, and/or reduce the symptoms of the maculopathy and/or pathogenic ocular neovascularization. Exemplary medicinal protocols include administration of pharmaceutical agents for prophylaxis and/or treatment with a composition formulated for ophthalmic administration and comprising a VEGF-C inhibitor, a VEGFR-2 inhibitor, or a VEGFR-3 inhibitor, or combinations thereof.

For example, in some variations, the system further includes a medical protocol database 214 operatively connected to a computer-readable medium of the system and containing information correlating the level of VEGF-C in the biological sample and medical protocols for human subjects with the maculopathy and/or pathogenic ocular neovascularization. Such medical protocols include any variety of medicines, lifestyle changes, diagnostic tests, increased frequencies of diagnostic tests, and the like that are designed to achieve effective therapy with minimum side effects. The information correlating the level of VEGF-C with protocols could include, for example, information about the success with which maculopathy and/or pathogenic ocular neovascularization is avoided or delayed, if a subject has a level of VEGF-C and follows a protocol.

By way of example, in some variations, a system that analyzes inputs of VEGF-C or assessing the potential for developing maculopathy and/or pathogenic ocular neovascularization could generate a variety of treatment protocols, for a subject determined to have increased risk, including a therapeutic regimen that includes a composition formulated for ophthalmic administration and comprising a VEGF-C inhibitor, a VEGFR-2 inhibitor or a VEGFR-3 inhibitor;

The system of this embodiment further includes a medical protocol tool or routine 216, operatively connected to the medical protocol database 214 and to the analysis tool or routine 210. The medical protocol tool or routine 216 preferably is stored on a computer-readable medium of the system, and adapted to be executed on a processor of the system, to: (i) compare (or correlate) the conclusion that is obtained from the analysis routine 210 (with respect to potential for the subject to develop maculopathy and/or pathogenic ocular neovascularization) and the medical protocol database 214, and (ii) generate a protocol report with respect to the probability that one or more medical protocols in the medical protocol database will achieve one or more of the goals of eliminating the disease or slowing onset of the disease.

Some variations of the system just described include the communication tool 212. In some examples, the communication tool generates a communication that includes the protocol report in addition to, or instead of, the conclusion with respect to potential for developing the disease.

Information about the level of VEGF-C not only can provide useful information about identifying or quantifying potential for developing maculopathy and/or pathogenic ocular neovascularization; it can also provide useful information about possible causative factors for a human subject identified with the disease, and useful information about therapies for the subject. In some variations, systems of the invention are useful for these purposes.

For instance, in some variations the invention is a system for assessing or selecting a treatment protocol for a subject diagnosed with a maculopathy and/or pathogenic ocular neovascularization. An exemplary system, schematically depicted in FIG. 17, comprises:

(a) at least one processor;

(b) at least one computer-readable medium;

(c) a medical treatment database 308 operatively connected to a computer-readable medium of the system and containing information correlating the level of VEGF-C and potential for the subject to develop maculopathy and/or pathogenic ocular neovascularization;

(d) a measurement tool 306 to receive an input (304, depicted in FIG. 13 but not part of the system per se) about the human subject and generate information from the input 304 about the level of VEGF-C indicative of maculopathy and/or pathogenic ocular neovascularization in a human subject diagnosed with the disease; and (e) a medical protocol routine or tool 310 operatively coupled to the medical treatment database 308 and the measurement tool 306, stored on a computer-readable medium of the system, and adapted to be executed on a processor of the system, to compare the information with respect to the level of VEGF-C in a biological sample of the subject and the medical treatment database, and generate a conclusion with respect to at least one of:

(i) the probability that one or more medical treatments will be efficacious for treatment of the disease for the subject; and (ii) which of two or more medical treatments will be more efficacious for the patient. In some variation, the subject is a subject diagnosed with the disease or condition, and the medical intervention is to treat the disease or condition. In some variations, the subject has no symptoms or evidence of the disease or condition and the medical treatments are prophylactic.

Preferably, such a system further includes a communication tool 312 operatively connected to the medical protocol tool or routine 310 for communicating the conclusion to the subject 300, or to a medical practitioner for the subject 302 (both depicted in the schematic of FIG. 7, but not part of the system per se). An exemplary communication tool comprises a routine stored on a computer-readable medium of the system and adapted to be executed on a processor of the system, to generate a communication containing the conclusion; and transmit the communication to the subject or the medical practitioner, or enable the subject or medical practitioner to access the communication.

The invention further provides compositions and kits including a VEGFR-2 inhibitor molecule and/or VEGFR-3 inhibitor molecule and/or VEGF-C inhibitor molecule and instructions (e.g., on a label or package insert such as instructions to the subject or to the clinician) for administering the VEGFR-2 inhibitor molecule and/or VEGFR-3 inhibitor molecule and/or VEGF-C inhibitor molecule to a subject to treat, prevent, and/or delay the development or progression of AMD. The anti-inflammatory agent can be in a pharmaceutical composition also including a pharmacologically acceptable carrier.

As used herein, "pharmaceutically acceptable carrier" includes saline, solvents, dispersion media, coatings, antibacterial and antifungal agents, isotonic and absorption delaying agents, and the like, compatible with pharmaceutical administration. A pharmaceutical composition is typically formulated to be compatible with its intended route of administration, e.g., ocular, oral, mucosal, topical, transdermal, or parenteral. Supplementary active compounds can also be incorporated into the compositions.

In some embodiments, a composition comprising a ligand binding molecule described herein is formulated for delivery to the eye of a subject (e.g., subconjunctivally, retrobulbarly, periocularly, subretinally, suprachoroidally, or intraocularly). Suitable ophthalmic carriers are known to those skilled in the art and all such conventional carriers may be employed in the present invention. Exemplary compounds incorporated to facilitate and expedite transdermal delivery of topical compositions into ocular or adnexal tissues include, but are not limited to, alcohol (ethanol, propanol, and nonanol), fatty alcohol (lauryl alcohol), fatty acid (valeric acid, caproic acid and capric acid), fatty acid ester (isopropyl myristate and isopropyl n-hexanoate), alkyl ester (ethyl acetate and butyl acetate), polyol (propylene glycol, propanedione and hexanetriol), sulfoxide (dimethylsulfoxide and decylmethylsulfoxide), amide (urea, dimethylacetamide and pyrrolidone derivatives), surfactant (sodium lauryl sulfate, cetyltrimethylannmonium bromide, polaxamers, spans, tweens, bile salts and lecithin), terpene (d-limonene, alphaterpeneol, 1,8-cineole and menthone), and alkanone (N-heptane and N-nonane). Moreover, topically-administered compositions comprise surface adhesion molecule modulating agents including, but not limited to, a cadherin antagonist, a selectin antagonist, and an integrin antagonist. Thus, a particular carrier may take the form of a sterile, ophthalmic ointment, cream, gel, solution, or dispersion. Also including as suitable ophthalmic carriers are slow release polymers, e.g., "Ocusert" polymers, "Hydron" polymers, etc.

Exemplary ophthalmic viscosity enhancers that can be used in the present formulation include: carboxymethyl cellulose sodium; methylcellulose; hydroxypropyl cellulose; hydroxypropylmethyl cellulose; hydroxyethyl cellulose; polyethylene glycol 300; polyethylene glycol 400; polyvinyl alcohol; and providone.

Some natural products, such as veegum, alginates, xanthan gum, gelatin, acacia and tragacanth, may also be used to increase the viscosity of ophthalmic solutions.

A tonicity is important because hypotonic eye drops cause an edema of the cornea, and hypertonic eye drops cause deformation of the cornea. The ideal tonicity is approximately 300 mOsM. The tonicity can be achieved by methods described in Remington: The Science and Practice of Pharmacy, known to those versed in the art.

Stabilizers may also be used such as, for example, chelating agents, e.g., EDTA. Antioxidants may also be used, e.g., sodium bisulfite, sodium thiosulfite, 8-hydroxy quinoline or ascorbic acid. Sterility typically will be maintained by conventional ophthalmic preservatives, e.g., chiorbutanol, benzalkonium chloride, cetylpyridium chloride, phenyl mercuric salts, thimerosal, etc., for aqueous formulations, and used in amounts which are nontoxic and which generally vary from about 0.001 to about 0.1% by weight of the aqueous solution. Conventional preservatives for ointments include methyl and propyl parabens. Typical ointment bases include white petrolatum and mineral oil or liquid petrolatum. However, preserved aqueous carriers are preferred. Solutions may be manually delivered to the eye in suitable dosage form, e.g., eye drops, or delivered by suitable microdrop or spray apparatus typically affording a metered dose of medicament. Examples of suitable ophthalmic carriers include sterile, substantially isotonic, aqueous solutions containing minor amounts, i.e., less than about 5% by weight hydroxypropylmethylcellulose, polyvinyl alcohol, carboxymethylcellulose, hydroxyethylcelullose, glycerine and EDTA. The solutions are preferably maintained at substantially neutral pH and isotonic with appropriate amounts of conventional buffers, e.g., phosphate, borate, acetate, tris.

In some embodiments, penetration enhancers are added to the ophthalmologic carrier.

Routes of administration suitable for the methods of the invention include both systemic and local administration. As used herein, the term "systemic administration" means a mode of administration resulting in delivery of a pharmaceutical composition to essentially the whole body of the patient. Exemplary modes of systemic administration include, without limitation, intravenous injection and oral administration. The term "local administration," as used herein, means a mode of administration resulting in significantly more pharmaceutical composition being delivered to and about the eyes than to regions distal from the eyes.

In some embodiments, a pharmaceutical composition comprising a VEGFR-2 inhibitor or VEGFR-3 inhibitor or a VEGF-C inhibitor described herein is administered topically, or by local injection (e.g., by intravitreal injection), or is released from an intraocular or periocular implant such as a bioerodible or reservoir-based implant. The composition is preferably administered in an amount effective to inhibit VEGF-C in the eye of the subject from binding to or stimulating VEGFR-2 and/or VEGFR-3 expressed in cells of the eye or vessels of the eye.

As used herein, the term "implant" refers to any material that does not significantly migrate from the insertion site following implantation. An implant can be biodegradable, non-biodegradable, or composed of both biodegradable and non-biodegradable materials; a non-biodegradable implant can include, if desired, a refillable reservoir. Implants useful in the methods of the invention include, for example, patches, particles, sheets, plaques, microcapsules and the like, and can be of any shape and size compatible with the selected site of insertion, which can be, without limitation, the posterior chamber, anterior chamber, suprachoroid or subconjunctiva. It is understood that an implant useful in the invention generally releases the implanted pharmaceutical composition at an effective dosage to the eye of the patient over an extended period of time. A variety of ocular implants and extended release formulations suitable for ocular release are well known in the art, as described, for example, in U.S. Pat. Nos. 5,869,079 and 5,443,505, the disclosures of which are incorporated herein by reference in their entireties.

In other embodiments, a VEGFR-2 inhibitor or VEGFR-3 inhibitor or VEGF-C inhibitor described herein is applied to the eye via liposomes. In still another embodiment, the ligand binding molecule is contained within a continuous or selective-release device, for example, membranes such as, but not limited to, those employed in the Ocusert™ System (Alza Corp., Palo Alto, Calif.). As an additional embodiment, the VEGFR-2 inhibitor or VEGFR-3 inhibitor or VEGF-C inhibitor is contained within, carried by, or attached to contact lenses which are placed on the eye. In yet another embodiment, the a VEGFR-2 inhibitor or VEGFR-3 inhibitor or VEGF-C inhibitor described herein molecule is contained within a swab or sponge which can be applied to the ocular surface. Another embodiment of the present invention involves a VEGFR-2 inhibitor or VEGFR-3 inhibitor or VEGF-C inhibitor described herein within a liquid spray which can be applied to the ocular surface.

In some embodiments, the VEGFR-2 inhibitor molecule and/or VEGFR-3 inhibitor molecule and/or VEGF-C inhibitor molecule is in a form suitable for local delivery to the macular area, e.g., an implantable form. An effective amount is a dosage of the VEGFR-2 inhibitor molecule and/or VEGFR-3 and/or VEGF-C inhibitor molecule sufficient to provide a medically desirable result. The effective amount will vary with the particular condition being treated, the age and physical condition of the subject being treated, the severity of the condition, the duration of the treatment, the nature of the concurrent therapy (if any), the specific route of administration and the like factors within the knowledge and expertise of the health practitioner. For example, an effective amount can depend upon the degree to which a subject has abnormally elevated levels of markers, e.g. VEGF-C levels, of AMD. In some embodiments, the VEGFR-2 inhibitor molecule and/or VEGFR-3 inhibitor molecule and/or VEGF-C inhibitor molecule is used to prevent the development or progression of AMD, that is, they are used prophylactically in subjects at risk of developing AMD, or in subjects that already have AMD but whose AMD is likely to progress, e.g., to a more severe form of the disease. Thus, an "effective amount" is that amount which can lower the risk of, slow, or prevent altogether the development or progression of AMD.

In some embodiments, the VEGFR-2 inhibitor molecule and/or VEGFR-3 inhibitor molecule and/or VEGF-C inhibitor molecule is administered in an effective amount, e.g., in an amount effective to reduce levels of one or more markers of angiogenesis and in particular VEGF-A or VEGF-C, preferably VEGF-C, to reduce the levels of the marker(s) to place the subject in a lower risk category, e.g., as described herein. The VEGFR-2 inhibitor molecule and/or VEGFR-3 inhibitor molecule and/or VEGF-C inhibitor molecule can be administered in one or more doses to achieve a desired therapeutic effect. Generally, doses of active compounds can be from about 0.01 mg/kg per day to 1000 mg/kg per day. It is expected that doses ranging from 50-500 mg/kg will be suitable, typically administered orally, and in one to three (or more) administrations per day. Lower doses may result from other forms of administration, such as intravenous administration. In the event that a response in a subject is insufficient at the initial doses applied, higher doses (or effectively higher doses by a different, more localized delivery route) may be employed to the extent that subject tolerance permits. Multiple doses per day are contemplated to achieve appropriate systemic levels of compounds. The dosage and schedule will depend on the VEGFR-2 inhibitor molecule and/or VEGFR-3 inhibitor molecule and/or VEGF-C inhibitor molecule selected; a skilled practitioner would be able to select a regimen appropriate for the particular agent and subject. A number of anti-inflammatory agents are known in the art, and can be used in the methods described herein. A variety of administration routes are available. The particular mode selected will depend upon the particular drug selected, the severity of the condition being treated and the dosage required for therapeutic efficacy. The methods described herein, generally speaking, can be practiced using any mode of administration that is medically acceptable, meaning any mode that produces effective levels of the active compounds without causing clinically unacceptable adverse effects. Such modes of administration include oral, rectal, topical, nasal, transdermal, or parenteral routes. The term "parenteral" includes subcutaneous, intravenous, intramuscular, or infusion. Local administration to the macular area can also be used. In some embodiments, the invention includes the use of implantable formulations, e.g., VEGFR-2 inhibitor molecules and/or VEGFR-3 inhibitor molecules and/or VEGF-C inhibitor molecules that are contained in a slow-release formula that can be implanted at or near the site of inflammation. Oral administration will typically be used for prophylactic and long term treatment because of the convenience to the subject as well as the dosing schedule. A number of oral compositions are known in the art and can be used in the methods described herein. The delivery systems can include time-release, delayed release or sustained release delivery systems. Such systems can avoid repeated administrations of the VEGFR-2 inhibitor molecule and/or VEGFR-3 inhibitor molecule and/or VEGF-C inhibitor molecule, increasing convenience to the subject and the physician.

Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems can also include non-polymer systems that are: lipids including sterols such as cholesterol, cholesterol esters and fatty acids or neutral fats such as mono-, di- and tri-glycerides; hydrogel release systems; sylastic systems; peptide based systems; wax coatings; compressed tablets using conventional binders and excipients; partially fused implants; and the like. Specific examples include, but are not limited to, erosional systems in which the anti-inflammatory agent is contained in a form within a matrix such as those described in U.S. Pat. Nos. 4,452,775, 4,667,014, 4,748,034 and 5,239,660, and diffusional systems in which an active component permeates at a controlled rate from a polymer such as described in U.S. Pat. Nos. 3,832,253, and 3,854,480. Pump-based hardware delivery systems can be used, some of which are adapted for implantation. In addition, U.S. Pat. No. 6,331,313 describes a biocompatible ocular drug delivery implant device that can be used to deliver VEGFR-2 inhibitor molecules and/or VEGFR-3 inhibitor molecules directly to the macular region. Use of a long-term sustained release implant may be particularly suitable for treatment of chronic conditions. Long-term release means that the implant is constructed and arranged to delivery therapeutic levels of the active ingredient for at least 30 days, e.g., 60 days. Long-term sustained release implants are known to those in the art and include some of the release systems described herein. Thus, the invention includes the use of a VEGFR-2 inhibitor molecule and/or VEGFR-3 inhibitor molecule to treat, delay or prevent the development or progression of AMD.

The invention further includes the use of a VEGFR-2 inhibitor molecule and/or VEGFR-3 inhibitor molecule and/or VEGF-C inhibitor molecule to modulate VEGF-C levels, thereby treating, delaying or preventing the development or progression of AMD.

Finally, the invention includes the use of a VEGFR-2 inhibitor molecule and/or VEGFR-3 inhibitor molecule and/or VEGF-C inhibitor molecule in the preparation of a medicament for use in the treatment of AMD.

All publications and patents mentioned herein are hereby incorporated by reference in their entirety as if each individual publication or patent was specifically and individually indicated to be incorporated by reference. In case of conflict, the present application, including any definitions herein, will control.

The invention is further described in the following examples, which do not limit the scope of the invention described in the claims.

EXAMPLES

Choroidal neovascularization (CNV) is the major cause of severe visual loss in subjects with AMD. At least 40% of subjects with wet AMD exhibit some degree of resistance to anti-VEGF-A monotherapy. We sought to investigate if circulating and tissue levels of VEGF-C are elevated in AMD subjects and determine if VEGF-C/-D blockade can inhibit choroidal neovascularization and leakage in a mouse model of wet AMD

Example 1

Plasma VEGF-A, VEGF-C and VEGF-D levels were measured in plasma samples from subjects with AMD and in control subjects without AMD and quantitated using a multiplex assay (Biorad).

The results are summarized in FIG. 1. VEGF-C levels are significantly elevated in the plasma of AMD subjects compared to healthy volunteers (controls).

Example 2

VEGF-C, VEGFR-2 and VEGFR-3 were localized in retinal tissues of C57BL/6 mice 14 days following laser injury and clinical specimens from wet AMD subjects by immunofluorescence using commercially available antibodies (Abcam). Results indicated that VEGF-C and its cognate receptors (i.e., VEGFR-2 and VEGFR-3) are expressed and co-localized in CNV membranes in the samples tested.

Example 3

To determine whether VEGF-C and VEGF-D participate in choroidal neovascularization, a mouse model of laser-induced CNV was employed in which photocoagulation was induced at 8-9 positions on each mouse retina (50 μm, 700 mW, 100 ms).

Figure 2A:
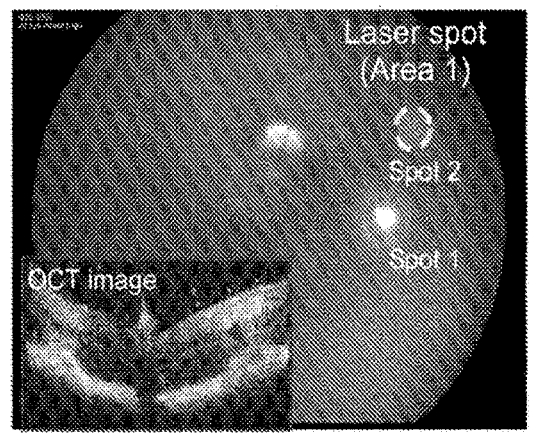
FIG. 2A shows an OCT image of laser-induced bulb in choroidal layer and shows the laser spot.
Figure 2B:
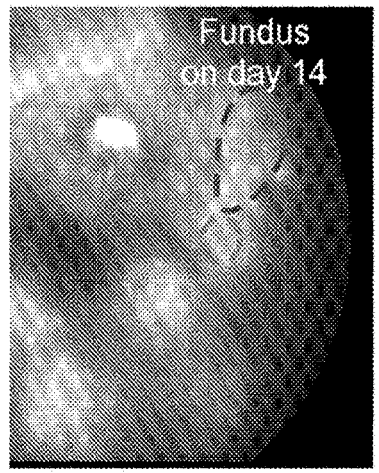
FIG. 2B shows the fundus on day 14.
Figure 2C:
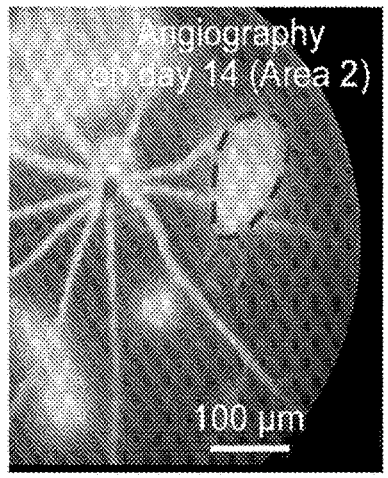
FIG. 2C shows the angiography on day 14.

Mice (5/group) were administered non-specific IgG (20 mg/kg IP every 2 days), Eylea™ (aflibercept, 20 mg/kg IP every 2 days), or VGX-300 (VEGFR-3 Trap for VEGF-C & VEGF-D; single-intravitreal injection of 40 μg on day 1). CNV areas and extent of leakage were determined by fluorescein angiography (FA) followed by intracardiac perfusion of FITC-dextran in gelatin (10%) on day 14 after photocoagulation (FIG. 2).

Example 4

Figure 3:
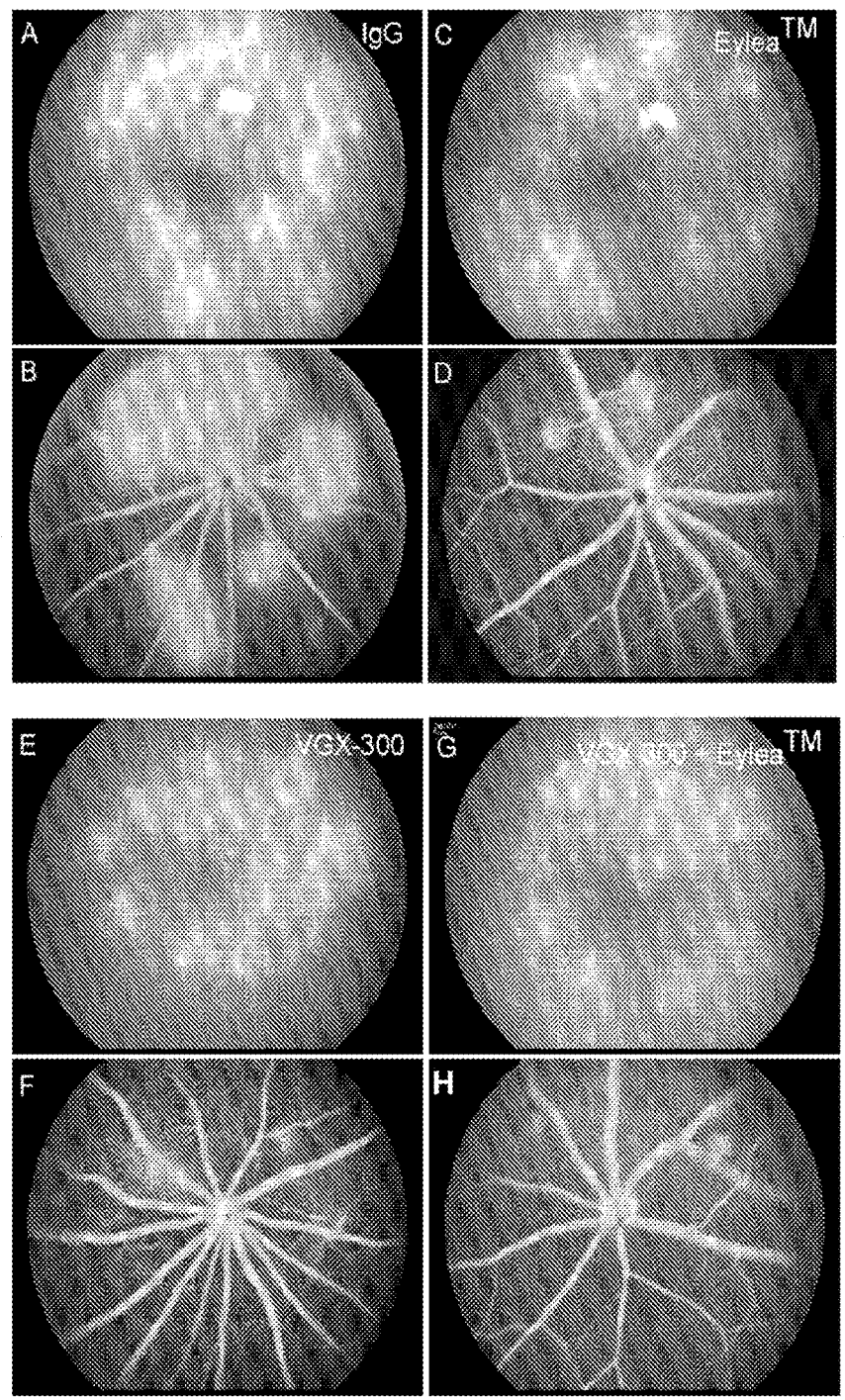
FIG. 3: Effects of VEGF-A and VEGF-C Inhibition on Laser-induced CNV. Fundus images and angiography of laser-induced CNV membranes 14 days after photocoagulation and administration of IgG (A&B), Eylea™ (C&D), VGX-300 (E&F) and VGX-300+Eylea™ (G&H) are shown.
Figure 4:
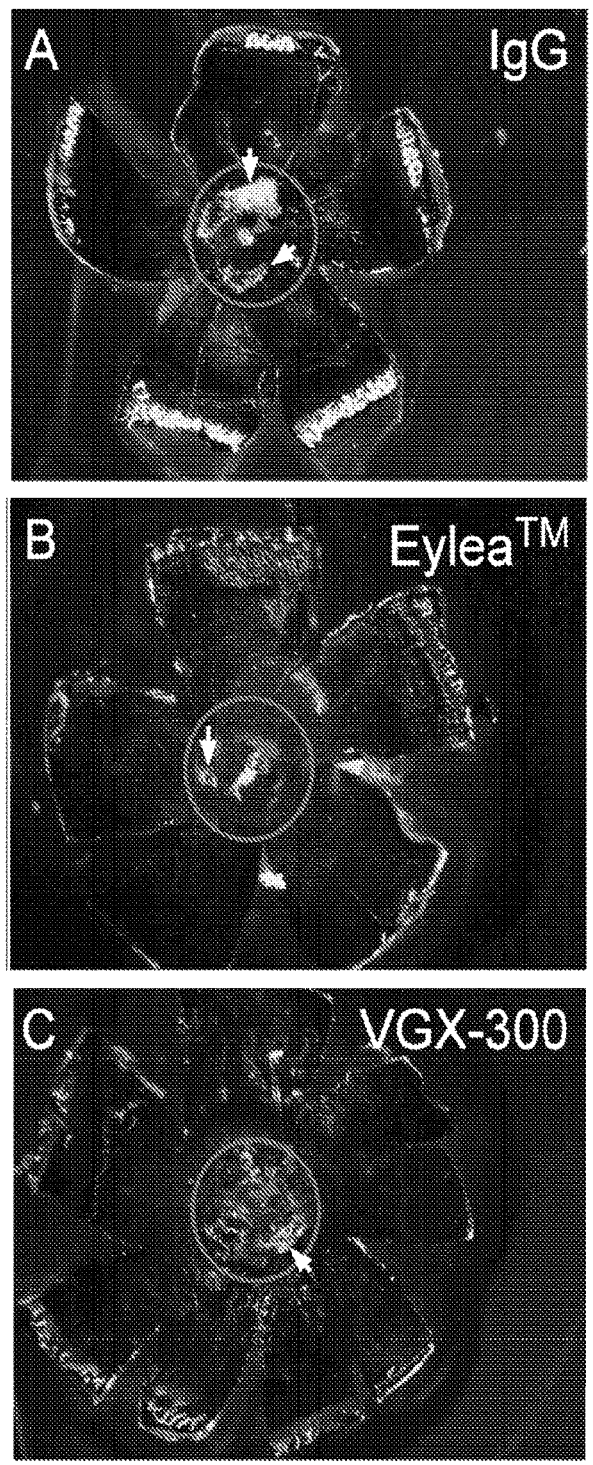
FIG. 4: CNV lesion sizes in choroidal flatmounts. Anatomical areas of CNV lesions 14 days after photocoagulation in IgG-treated (A), of Eylea™-treated (B) and VGX-300 treated (C) eyes. A grey circle shows the photocoagulation area; a grey arrow head identifies the optic nerve head; a white arrow highlights CNV leakage.
Figure 5:
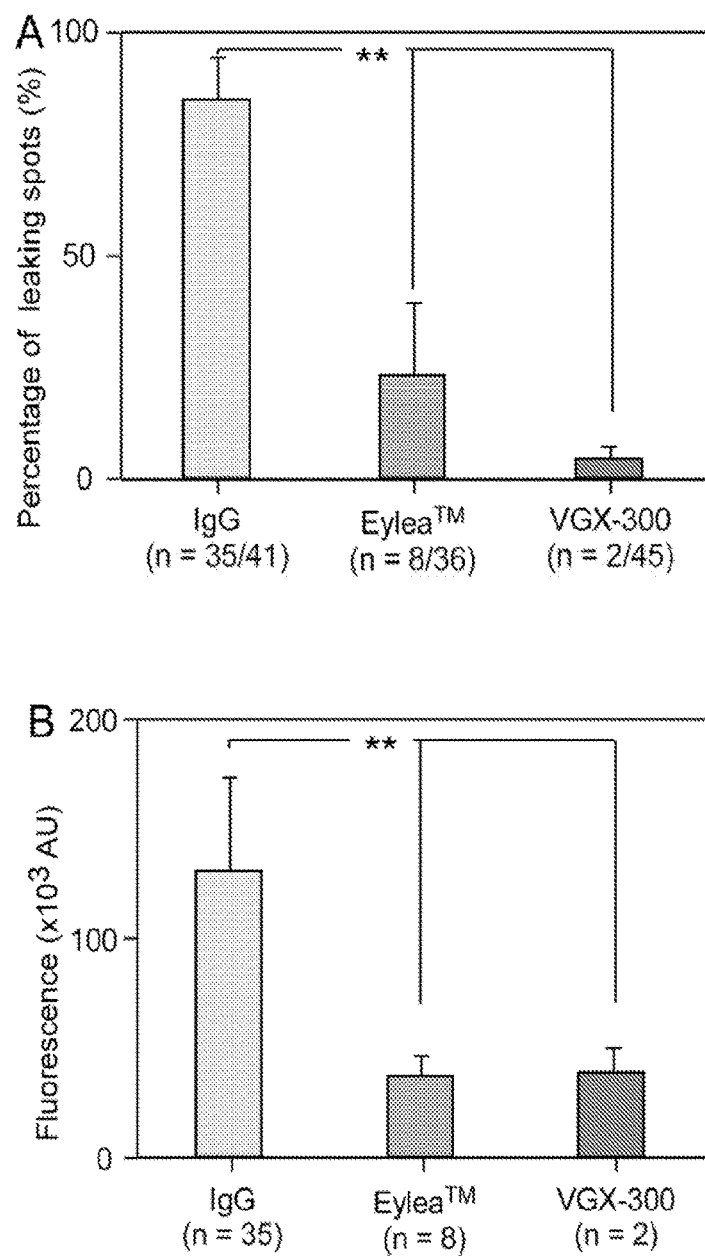
FIG. 5: Incidence of CNV and intensity of leakage. (A) Incidence of laser-induced leaking spots (leakage spots/photocoagulated spots×100%). (B) Comparison of leakage intensity after fluorescein angiography.
Figure 6:
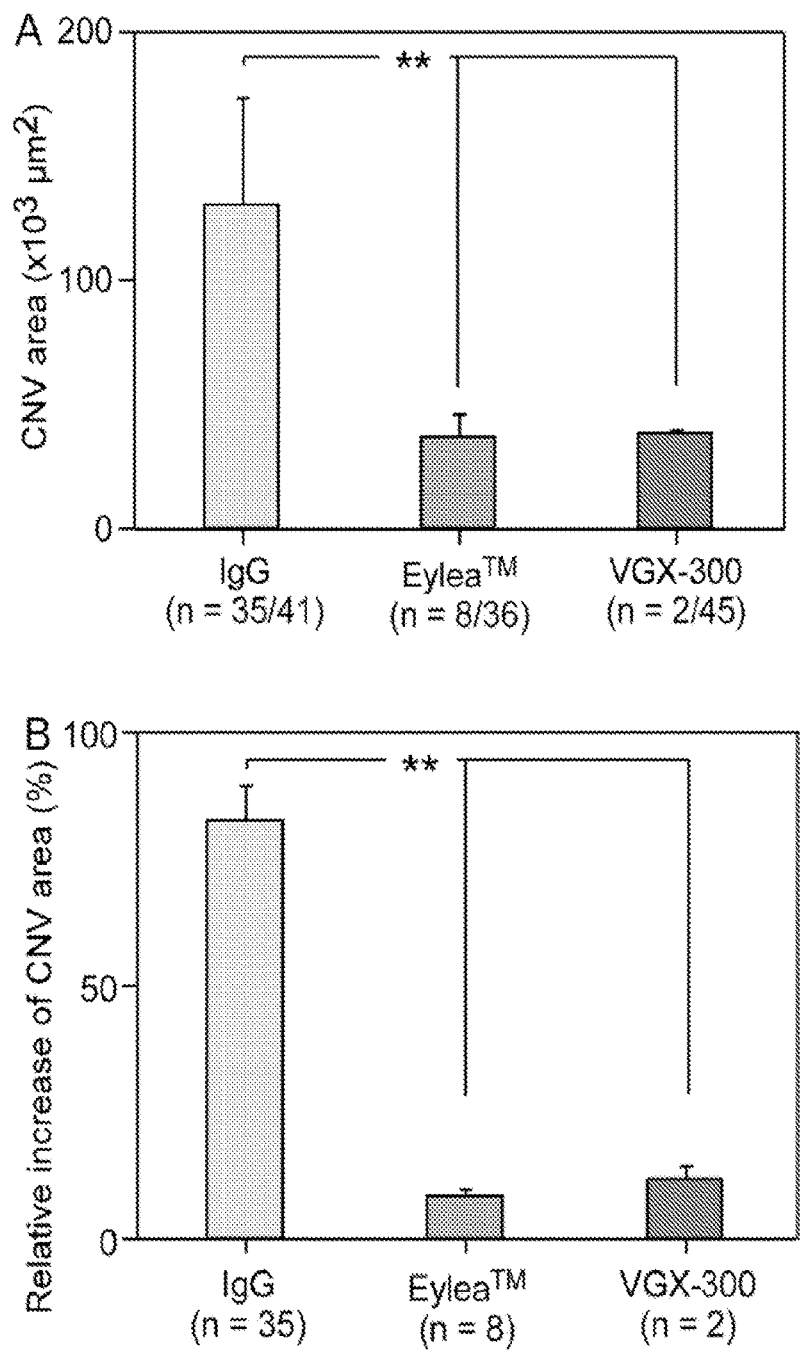
FIG. 6: Effects of treatment on CNV area. (A) Mean size of laser-induced CNV membranes (total area of leakage spots/total photocoagulated spots). (B) Percentage of relative increase in CNV area (refer to FIG. 1 for calculation method). The CNV area as shown in FIG. 5(A) was determined from fluorescein angiography as shown in FIGS. 4(b) and (c). Percentage of relative increase of CNV area, as shown in FIG. 5(B) was determined by calculating [(Area 2−Area 1)/Area 1]×100%.

Laser-induced CNV was created in C57BL/6 mice using a 532 nm laser under direct visualization using a Micron III® fundus camera (4-9 spots/eye; 50 μm size, 50 ms, 550 Mw). On day 0 post-laser injury, mice were administered a single intravitreal (IVT) injection of a negative isotype antibody control IgG, Eylea®, VGX-300 or the combination of VGX-300 and Eylea®. N=15 mice per treatment group. For each injection, a total of 80 mg protein was administered in a 2 ml injection (for single-agent groups, 40 mg of IgG was added to each 40 mg dose of Eylea® or VGX-300). FIG. 3 shows fundus images and fluorescein angiography of laser-induced CNV membranes 14 days after photocoagulation. FIG. 4 shows CNV lesion sizes in choroidal flatmounts. Anatomical areas of CNV lesions 14 days after photocoagulation in IgG-treated animals (FIG. 4A) was much larger than those of Eylea™-treated (FIG. 4B) and VGX-300-treated (FIG. 4C) eyes. FIG. 5 shows the incidence of CNV and intensity of leakage after 14 days in each of the treatment groups. FIG. 6 shows the mean size of laser-induced CNV membranes (total area of leakage spots/total photocoagulated spots) and the percentage of relative increase in CNV area after 14 days in each treatment group.

Both Eylea® and VGX-300 significantly reduced CNV area (FIG. 7) compared to the IgG control treated group. VGX-300 reduced lesion size to the approximate size of the laser-burn.

Examples 5

Figure 8:
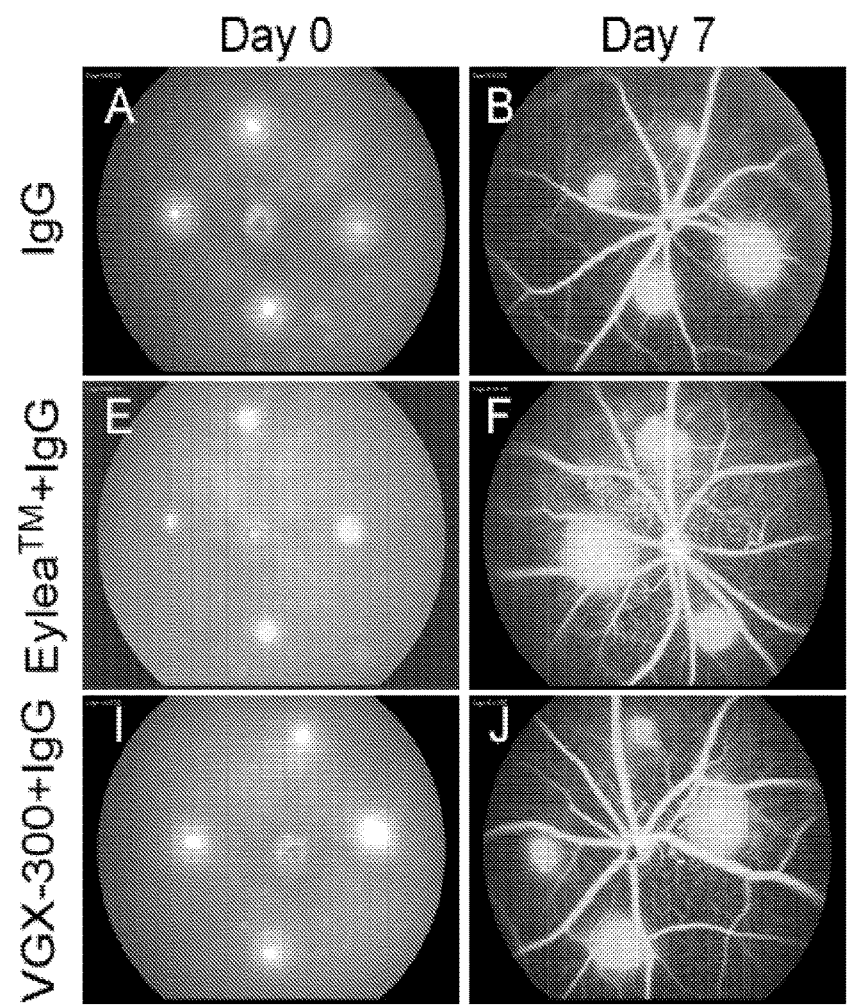
FIG. 8: Representative fundus images, angiography and choroidal flatmounts of laser-induced CNV membranes 7 and 14 days after laser-burn and administration, on day 7: (A-D) IgG (80 μg); (E-H) Eylea® (40 μg)+IgG (40 μg); (I-L) VGX-300 (40 μg)+IgG (40 μg). Circles indicate the optic heads and arrows point to the CNV lesions.
Figure 8:
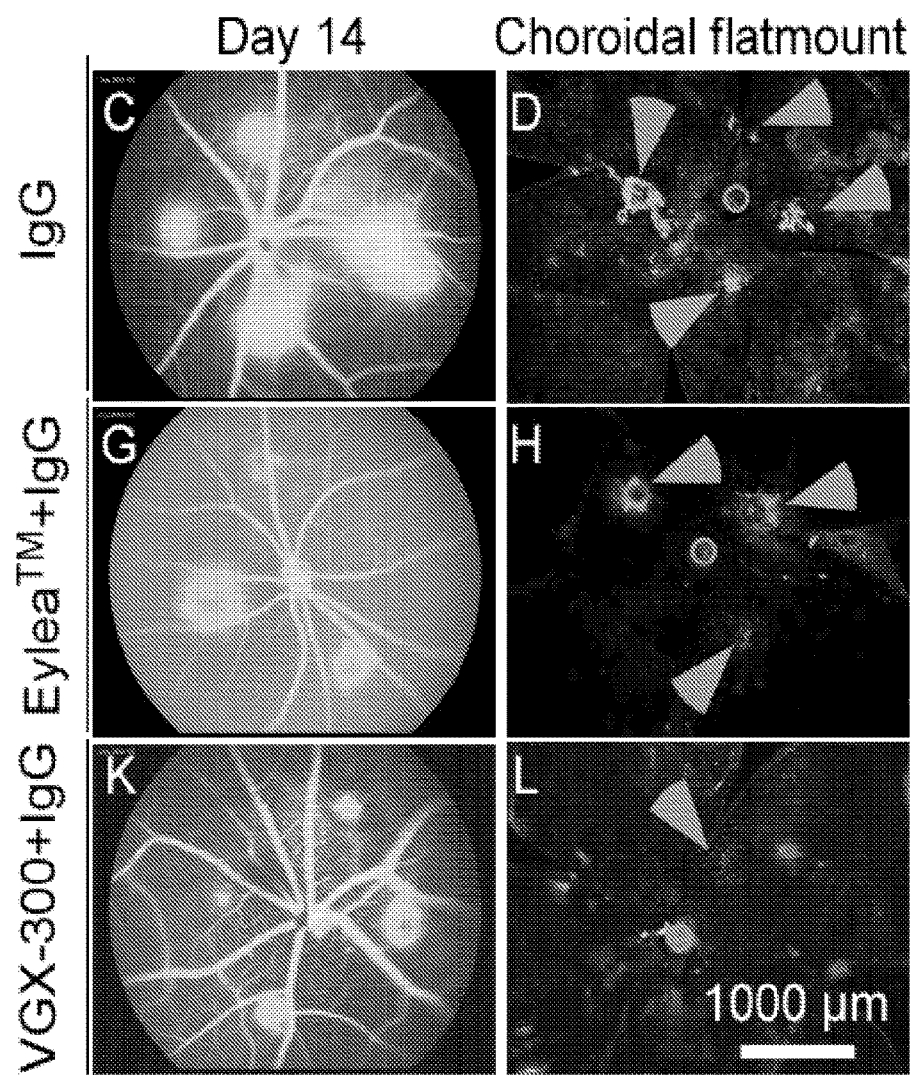
Figure 9A:
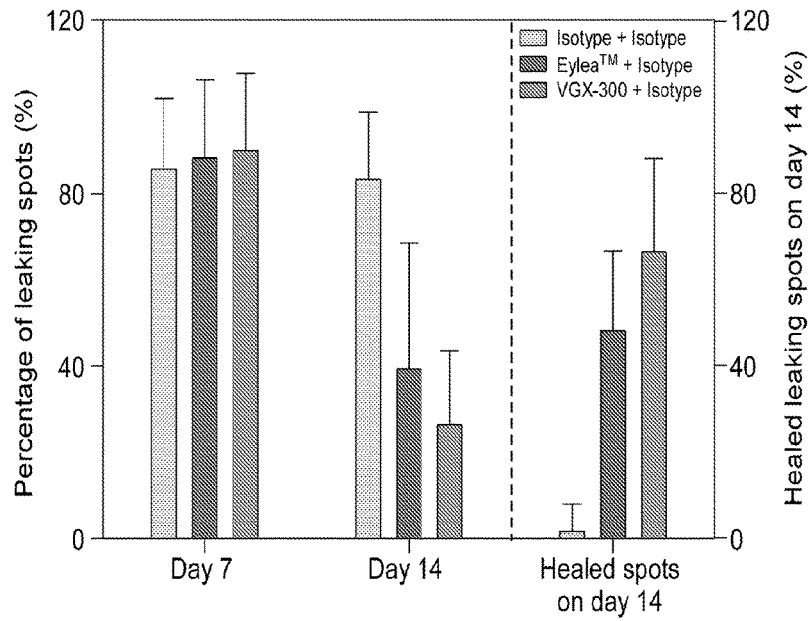
FIG. 9: Regression of CNV lesions following VGX-300 treatment: (A) Incidence of laser-induced leaking spots on day 7 and on day 14 post-laser injury (leaking spots/photocoagulated spots×100%); (B) Mean size of laser-induced CNV membranes at day 14 post-laser injury.
Figure 9B:
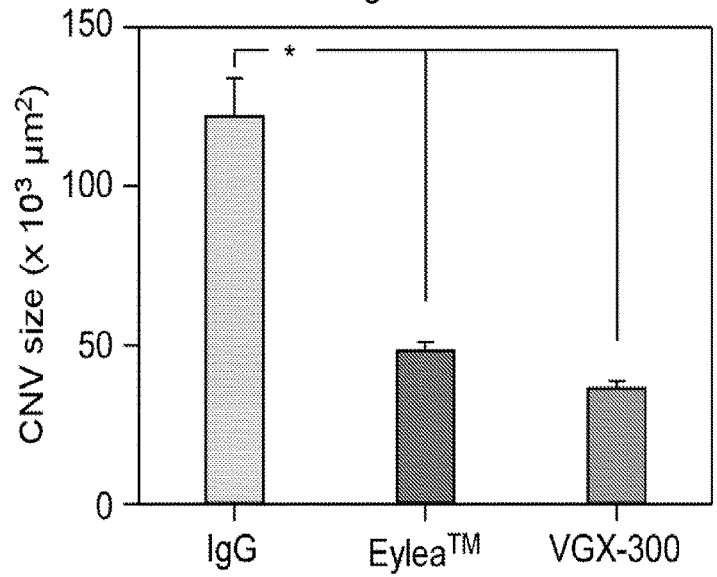

Laser-induced CNV was created in C57BL/6 mice using a 532 nm laser under direct visualization using a Micron III® fundus camera (4-9 spots/eye; 50 μm size, 50 ms, 550 Mw). On day 7 post-laser injury, mice were administered a single intravitreal (IVT) injection of a negative isotype antibody control IgG, Eylea®+IgG or VGX-300+IgG. For each injection, a total of 80 mg protein was administered in a 2 ml injection (for single-agent groups, 40 mg of IgG was added to each 40 mg dose of Eylea® or VGX-300). N=10 mince per treatment group. Extent of leakage and CNV areas were determined by fluorescein angiography followed by intracardiac perfusion of FITC-dextran in gelatin (10%) on days 7 and 14 post-laser burn. FIG. 8 shows representative fundus images, angiography and choroidal flatmounts of laser-induced CNV membranes 7 and 14 days after laser-burn and administration. FIG. 9(A) shows the incidence of laser-induced leaking spots on day 7 and on day 14 post-laser injury (leaking spots/photocoagulated spots×100%. FIG. 9(B) shows the mean size of laser-induced CNV membranes at day 14 post-laser injury.

Example 6

Figure 10:
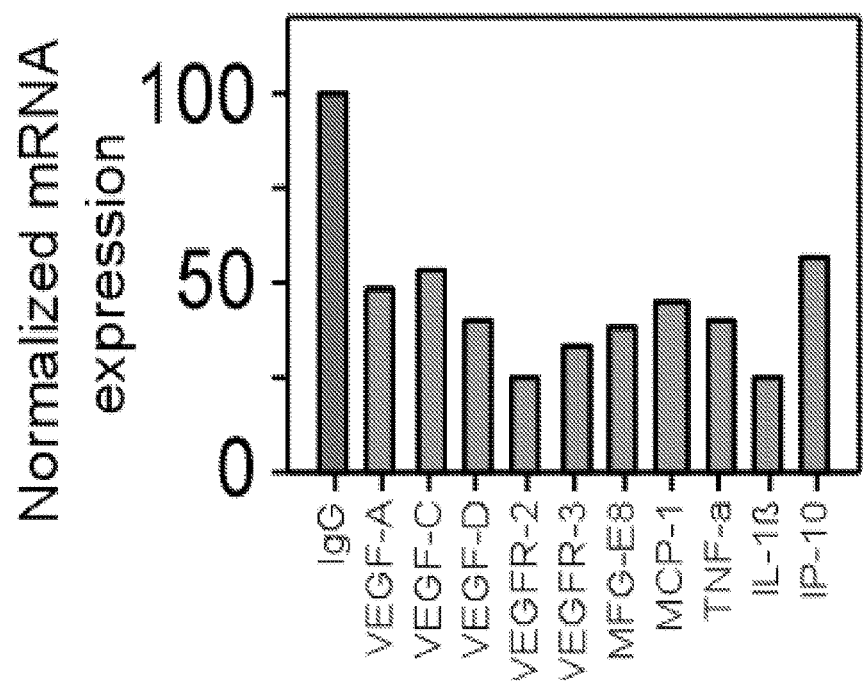
FIG. 10: The normalized accumulated mRNA expression levels of a panel of angiogenic and inflammatory genes on day 0, 1, 3, 7 and 14 post-laser injury in the ocular tissue of mice treated with VGX-300 compared to IgG group. (n=10 mice/group on each sampling day).

The modulation of expression of a panel of angiogenesis and inflammatory genes in mouse CNV following VGX-300 administration was evaluated by quantitative RT-PCR (qRT-PCR). FIG. 10 shows the normalized accumulated mRNA expression levels of a panel of angiogenic and inflammatory genes on day 0, 1, 3, 7 and 14 post-laser injury in the ocular tissue of mice treated with VGX-300 compared to IgG group. (n=10 mice/group on each sampling day).

The results demonstrate that VGX-300-mediated blockade of VEGF-C/-D significantly inhibits choroidal neovascularization and vascular leakage comparably to Eylea™ in the laser-induced mouse model of wet AMD. Persistent angiogenesis and vascular leakage in these sub-responsive subjects may be mediated by VEGF-C. Established CNV lesions in the mouse regress following treatment with VGX-300 on day 7 post-laser injury. VEGF-C expression is higher in wet AMD and lower in control and dry AMD clinical specimens. VGX-300 reduces the expression of genes associated with angiogenesis and inflammation following laser-induced injury. Administration of single-agent VGX-300 may be an effective therapy for wet AMD. Administered in combination with anti-VEGF-A therapies, VGX-300 may have the potential to improve clinical responses in wet AMD by more effective inhibition of the pathways involved in disease progression.

What is claimed is:

1. A method of prophylaxis or treatment of a disease or condition selected from macular degeneration and pathogenic ocular neovascularization, the method comprising:
    (a) measuring VEGF-C protein in a biological sample from a human subject to obtain a VEGF-C measurement,
    (b) determining from the VEGF-C protein measurement that VEGF-C protein is elevated in the subject, and
    (c) administering, to the eye of a subject identified as having elevated VEGF-C protein in the biological sample, a composition formulated for ophthalmic administration and comprising a VEGF-C inhibitor, said VEGF-C inhibitor comprising:
        (i) a polypeptide comprising a VEGFR-3 fragment, said fragment having an amino terminus selected from positions 1-47 of SEQ ID NO: 4, and a carboxy terminus selected from positions 211-247 of SEQ ID NO: 4, or
        (ii) a polypeptide comprising the sequence of amino acids defined by positions 47-314 of SEQ ID NO: 4, with the proviso that positions of the polypeptide corresponding to positions 104-106 of SEQ ID NO: 4 are not identical to N-X-S or N-X-T,
    wherein said inhibitor binds human VEGF-C.

2. A method of monitoring and adjusting the dose of a prophylactic or therapeutic administered to a human subject for macular degeneration or for pathogenic ocular neovascularization, the method comprising:
    (a) administering to a human subject diagnosed with, or identified as having elevated risk for, a macular degeneration or pathogenic ocular neovascularization, a composition formulated for ophthalmic administration and comprising a VEGF-C inhibitor, said VEGF-C inhibitor comprising a polypeptide comprising:
        (i) a VEGFR-3 fragment, said fragment having an amino terminus selected from positions 1-47 of SEQ ID NO: 4, and a carboxy terminus selected from positions 211-247 of SEQ ID NO: 4, or
        (ii) a polypeptide comprising the sequence of amino acids defined by positions 47-314 of SEQ ID NO: 4, with the proviso that positions of the polypeptide corresponding to positions 104-106 of SEQ ID NO: 4 are not identical to N-X-S or N-X-T,
    wherein said inhibitor binds human VEGF-C;
    (b) measuring VEGF-C protein in a biological sample from the subject, after the administering, to obtain a VEGF-C protein measurement;
    (c) re-administering the composition to the subject:
        (i) wherein the VEGF-C protein measurement from step (b) is elevated, and wherein the re-administering is performed with a greater dose and/or a more frequent dosing schedule to further reduce the VEGF-C in the subject; or (ii) wherein the VEGF-C protein measurement from step (b) is normal or below normal compared to apparently healthy subjects, and wherein the re-administering is performed with a smaller dose and/or a less frequent dosing schedule.

3. The method according to claim 1, wherein the disease or condition is macular degeneration.

4. The method according to claim 1, wherein the VEGF-C inhibitor is selected from the group consisting of:
(a) a polypeptide comprising the extracellular domain fragment of VEGFR-3; and
b) a fragment of (a) that retains VEGF-C binding activity.

5. The method according to claim 4, further comprising co-administering to the subject a composition that comprises an inhibitor selected from the group consisting of a VEGF-A inhibitor, a VEGFR-2 inhibitor, and an inhibitor of the VEGFR-2 signalling pathway.

6. The method according to claim 4, wherein the biological sample comprises blood, serum, plasma, ocular tissue, ocular fluid, blood vessel tissue, or lymphatic vessel tissue.

7. The method according to claim 4, wherein the determination of elevated VEGF-C protein is made compared to one or more of the following reference measurements:
(a) a VEGF-C protein or VEGF C mRNA measurement from the subject from a biological sample obtained at an earlier point in time; or
(b) a VEGF-C protein measurement from one or more apparently healthy control subjects.

8. The method according to claim 4, further comprising measuring at least one additional maculopathy biomarker.

9. The method according to claim 4, further comprising measuring at least one environmental or lifestyle factor selected from the group consisting of age, weight, and body mass index.

10. The method according to claim 1, wherein the VEGF-C inhibitor further comprises an immunoglobulin constant region fragment (Fc) fused polypeptide comprising the VEGFR-3 fragment.

11. The method according to claim 1, wherein the polypeptide comprises an amino acid sequence having a sequence of amino acids defined by positions 47-314 of SEQ ID NO: 4, with the proviso that positions of the polypeptide corresponding to positions 104-106 of SEQ ID NO: 4 are not identical to N-X-S or N-X-T, and wherein the polypeptide binds to human VEGF-C.

12. The method according to claim 1, further comprising co-administering, to the eye of the subject identified as having the elevated VEGF-C protein, a composition that comprises an inhibitor selected from the group consisting of a VEGF-A inhibitor, a VEGFR-2 inhibitor, and an inhibitor of the VEGFR-2 signalling pathway.

13. The method according to claim 1, wherein the biological sample comprises blood, serum, plasma, ocular tissue, ocular fluid, blood vessel tissue, or lymphatic vessel tissue.

14. The method according to claim 1, wherein the administering to the eye comprises administering by intravitreal injection.

15. The method according to claim 2, comprising repeating steps (b) and (c).

16. The method according to claim 2, wherein the VEGF-C inhibitor further comprises an immunoglobulin constant region fragment (Fc) fused polypeptide comprising the VEGFR-3 fragment.

17. The method according to claim 2, wherein the polypeptide comprises an amino acid sequence having a sequence of amino acids defined by positions 47-314 of SEQ ID NO: 4, with the proviso that positions of the polypeptide corresponding to positions 104-106 of SEQ ID NO: 4 are not identical to N-X-S or N-X-T, and wherein the polypeptide binds to human VEGF-C.

18. The method according to claim 2, for monitoring and adjusting the dose of a prophylactic or therapeutic administration to a human subject for macular degeneration.

19. The method according to claim 2, wherein the biological sample comprises blood, serum, plasma, ocular tissue, ocular fluid, blood vessel tissue, or lymphatic vessel tissue.

20. The method according to claim 2, wherein the administering comprises intravitreal injection.

21. A method comprising obtaining an ocular tissue or fluid from a human subject,
measuring VEGF-C protein in the ocular tissue or fluid;
detecting an elevated VEGF-C protein measurement in the ocular tissue or fluid from the subject, compared to VEGF-C measurements from corresponding ocular tissue or fluid from apparently healthy control subjects; and
administering to the eye of the subject a composition formulated for ophthalmic administration and comprising a VEGF-C inhibitor, said VEGF-C inhibitor comprising:
(i) polypeptide comprising a VEGFR-3 fragment, said fragment having an amino terminus selected from positions 1-47 of SEQ ID NO: 4, and a carboxy terminus selected from positions 211-247 of SEQ ID NO: 4, or
(ii) a polypeptide comprising the sequence of amino acids defined by positions 47-314 of SEQ ID NO: 4, with the proviso that positions of the polypeptide corresponding to positions 104-106 of SEQ ID NO: 4 are not identical to N-X-S or N-X-T,
wherein said inhibitor binds human VEGF-C.

22. The method according to claim 21, wherein the VEGF-C inhibitor further comprises an immunoglobulin constant region fragment (Fc) fused polypeptide comprising the VEGFR-3 fragment.

23. The method according to claim 21, wherein the polypeptide comprises an amino acid sequence having a sequence of amino acids defined by positions 47-314 of SEQ ID NO: 4, with the proviso that positions of the polypeptide corresponding to positions 104-106 of SEQ ID NO: 4 are not identical to N-X-S or N-X-T, and wherein the polypeptide binds to human VEGF-C.

24. The method according to claim 21, wherein the subject has macular degeneration.

25. The method according to claim 21, further comprising co-administering, to the eye of the subject with the elevated VEGF-C protein measurement, a composition that comprises an inhibitor selected from the group consisting of a VEGF-A inhibitor, a VEGFR-2 inhibitor, and an inhibitor of the VEGFR-2 signalling pathway.

26. The method according to claim 21, wherein the administering to the eye comprises administering by intravitreal injection.

27. A method comprising:
(a) measuring VEGF-C protein in a biological sample from a human subject to obtain a VEGF-C protein measurement;
(b) detecting elevated VEGF-C protein in the biological sample, (c) determining that the subject has an increased risk of developing macular degeneration or pathogenic ocular neovascularization from the elevated measurement of VEGF-C protein in the biological sample;

(d) administering, to the eye of the subject determined to have the increased risk, a composition formulated for ophthalmic administration and comprising a VEGF-C inhibitor, said VEGF-C inhibitor comprising:
   (i) a VEGFR-3 fragment, said fragment having an amino terminus selected from positions 1-47 of SEQ ID NO: 4, and a carboxy terminus selected from positions 211-247 of SEQ ID NO: 4, or
   (ii) a polypeptide comprising the sequence of amino acids defined by positions 47-314 of SEQ ID NO: 4, with the proviso that positions of the polypeptide corresponding to positions 104-106 of SEQ ID NO: 4 are not identical to N-X-S or N-X-T,
wherein said inhibitor binds human VEGF-C.

28. The method according to claim 27, wherein the VEGF-C inhibitor further comprises an immunoglobulin constant region fragment (Fc) fused polypeptide comprising the VEGFR-3 fragment.

29. The method according to claim 27, wherein the polypeptide comprises an amino acid sequence having a sequence of amino acids defined by positions 47-314 of SEQ ID NO: 4, with the proviso that positions of the polypeptide corresponding to positions 104-106 of SEQ ID NO: 4 are not identical to N-X-S or N-X-T, and wherein the polypeptide binds to human VEGF-C.

30. The method according to claim 27, further comprising co-administering, to the eye of the subject determined to have the increased risk, a composition that comprises an inhibitor selected from the group consisting of a VEGF-A inhibitor, a VEGFR-2 inhibitor, and an inhibitor of the VEGFR-2 signalling pathway.

31. The method according to claim 27, wherein the biological sample comprises blood, serum, plasma, ocular tissue, ocular fluid, blood vessel tissue, or lymphatic vessel tissue.

32. The method according to claim 27, wherein the detecting of elevated VEGF-C protein is made compared to one or more of the following reference measurements:
   (a) a VEGF-C protein measurement from the subject from a biological sample obtained at an earlier point in time; or
   (b) a VEGF-C protein measurement from one or more apparently healthy control subjects.

33. The method according to claim 27, wherein the administering to the eye comprises administering by intravitreal injection.

* * * * *

SEQUENCE LISTING

```
<160> NUMBER OF SEQ ID NOS: 5

<210> SEQ ID NO 1
<211> LENGTH: 1997
<212> TYPE: DNA
<213> ORGANISM: Homo sapiens

<400> SEQUENCE: 1 cccgcccgc ctctccaaaa agctacaccg acgcggaccg cggcggcgtc ctccctcgcc      60
ctcgcttcac ctcgcgggct ccgaatgcgg ggagctcgga tgtccggttt cctgtgaggc     120
ttttacctga caccegeege cttteceegg cactggetgg gagggegece tgcaaagttg     180 ggaacgcgga gccccggacc cgctcccgcc gcctccggct cgcccagggg gggtcgccgg     240
gaggagcccg ggggagaggg accaggaggg gcccgcggcc tcgcaggggc gcccgcgccc     300
ccacccctgc ccccgccagc ggaccggtcc cccaccccg gtccttccac catgcacttg      360
ctgggcttct tctctgtggc gtgttctctg ctcgccgctg cgctgctccc gggtcctcgc      420
gaggcgcccg ccgccgccgc cgccttcgag tccggactcg acctctcgga cgcggagccc      480
gacgcgggcg aggccacggc ttatgcaagc aaagatctgg aggagcagtt acggtctgtg     540
tccagtgtag atgaactcat gactgtactc tacccagaat attggaaaat gtacaagtgt     600
cagctaagga aaggaggctg gcaacataac agagaacagg ccaacctcaa ctcaaggaca     660
gaagagacta taaaatttgc tgcagcacat tataatacag atcttgaa aagtattgat       720 aatgagtgga gaaagactca atgcatgcca cgggaggtgt gtatagatgt ggggaaggag     780
tttggagtcg cgacaaacac cttctttaaa cctccatgtg tgtccgtcta cagatgtggg     840
ggttgctgca atagtgaggg gctgcagtgc atgaacacca gcacgagcta cctcagcaag     900
acgttatttg aaattacagt gcctctctct caaggcccca aaccagtaac aatcagtttt     960
gccaatcaca cttcctgccg atgcatgtct aaactggatg tttacagaca agttcattcc    1020
```

-continued

```
attattagac gttccctgcc agcaacacta ccacagtgtc aggcagcgaa caagacctgc    1080
cccaccaatt acatgtggaa taatcacatc tgcagatgcc tggctcagga agattttatg    1140
ttttcctcgg atgctggaga tgactcaaca gatggattcc atgacatctg tggaccaaac    1200
aaggagctgg atgaagagac ctgtcagtgt gtctgcagag cggggcttcg gcctgccagc    1260
tgtggacccc acaaagaact agacagaaac tcatgccagt gtgtctgtaa aacaaactc     1320 ttccccagcc aatgtggggc aaccgagaaa tttgatgaaa acacatgcca gtgtgtatgt    1380
aaaagaacct gccccagaaa tcaaccccta atcctggaaa atgtgcctg tgaatgtaca     1440 gaaagtccac agaaatgctt gttaaaagga aagaagttcc accaccaaac atgcagctgt    1500
tacagacggc catgtacgaa ccgccagaag gcttgtgagc aggatttc atatagtgaa      1560 gaagtgtgtc gttgtgtccc ttcatattgg aaaagaccac aaatgagcta agattgtact    1620
gttttccagt tcatcgattt tctattatgg aaaactgtgt tgccacagta aactgtctg    1680 tgaacagaga gacccttgtg ggtccatgct aacaaagaca aaagtctgtc tttcctgaac    1740
catgtggata actttacaga aatggactgg agctcatctg caaaaggcct cttgtaaaga    1800
ctggttttct gccaatgacc aaacagccaa gattttcctc ttgtgatttc tttaaaagaa    1860
tgactatata atttatttcc actaaaaata ttgtttctgc attcattttt atagcaacaa    1920
caattggtaa aactcactgt gatcaatatt tttatatcat gcaaaatatg tttaaaataa    1980
aatgaaaatt gtattat                                                   1997
```

<210> SEQ ID NO 2
<211> LENGTH: 419
<212> TYPE: PRT
<213> ORGANISM: Homo sapiens

<400> SEQUENCE: 2

```
Met His Leu Leu Gly Phe Phe Ser Val Ala Cys Ser Leu Leu Ala Ala
1               5                   10                  15

Ala Leu Leu Pro Gly Pro Arg Glu Ala Pro Ala Ala Ala Ala Ala Phe
            20                  25                  30

Glu Ser Gly Leu Asp Leu Ser Asp Ala Glu Pro Asp Ala Gly Glu Ala
        35                  40                  45

Thr Ala Tyr Ala Ser Lys Asp Leu Glu Glu Gln Leu Arg Ser Val Ser
    50                  55                  60

Ser Val Asp Glu Leu Met Thr Val Leu Tyr Pro Glu Tyr Trp Lys Met
65                  70                  75                  80

Tyr Lys Cys Gln Leu Arg Lys Gly Gly Trp Gln His Asn Arg Glu Gln
                85                  90                  95

Ala Asn Leu Asn Ser Arg Thr Glu Glu Thr Ile Lys Phe Ala Ala Ala
            100                 105                 110

His Tyr Asn Thr Glu Ile Leu Lys Ser Ile Asp Asn Glu Trp Arg Lys
        115                 120                 125

Thr Gln Cys Met Pro Arg Glu Val Cys Ile Asp Val Gly Lys Glu Phe
    130                 135                 140

Gly Val Ala Thr Asn Thr Phe Phe Lys Pro Pro Cys Val Ser Val Tyr
145                 150                 155                 160

Arg Cys Gly Gly Cys Cys Asn Ser Glu Gly Leu Gln Cys Met Asn Thr
                165                 170                 175

Ser Thr Ser Tyr Leu Ser Lys Thr Leu Phe Glu Ile Thr Val Pro Leu
            180                 185                 190

Ser Gln Gly Pro Lys Pro Val Thr Ile Ser Phe Ala Asn His Thr Ser
```

```
                195                 200                 205
Cys Arg Cys Met Ser Lys Leu Asp Val Tyr Arg Gln Val His Ser Ile
    210                 215                 220
Ile Arg Arg Ser Leu Pro Ala Thr Leu Pro Gln Cys Gln Ala Ala Asn
225                 230                 235                 240
Lys Thr Cys Pro Thr Asn Tyr Met Trp Asn Asn His Ile Cys Arg Cys
                245                 250                 255
Leu Ala Gln Glu Asp Phe Met Phe Ser Ser Asp Ala Gly Asp Asp Ser
            260                 265                 270
Thr Asp Gly Phe His Asp Ile Cys Gly Pro Asn Lys Glu Leu Asp Glu
        275                 280                 285
Glu Thr Cys Gln Cys Val Cys Arg Ala Gly Leu Arg Pro Ala Ser Cys
    290                 295                 300
Gly Pro His Lys Glu Leu Asp Arg Asn Ser Cys Gln Cys Val Cys Lys
305                 310                 315                 320
Asn Lys Leu Phe Pro Ser Gln Cys Gly Ala Asn Arg Glu Phe Asp Glu
                325                 330                 335
Asn Thr Cys Gln Cys Val Cys Lys Arg Thr Cys Pro Arg Asn Gln Pro
            340                 345                 350
Leu Asn Pro Gly Lys Cys Ala Cys Glu Cys Thr Glu Ser Pro Gln Lys
        355                 360                 365
Cys Leu Leu Lys Gly Lys Lys Phe His His Gln Thr Cys Ser Cys Tyr
    370                 375                 380
Arg Arg Pro Cys Thr Asn Arg Gln Lys Ala Cys Glu Pro Gly Phe Ser
385                 390                 395                 400
Tyr Ser Glu Glu Val Cys Arg Cys Val Pro Ser Tyr Trp Lys Arg Pro
                405                 410                 415
Gln Met Ser

<210> SEQ ID NO 3
<211> LENGTH: 4195
<212> TYPE: DNA
<213> ORGANISM: Homo sapiens
<220> FEATURE:
<221> NAME/KEY: CDS
<222> LOCATION: (20)..(3913)

<400> SEQUENCE: 3
ccacgcgcag cggccggag atg cag cgg ggc gcc gcg ctg tgc ctg cga ctg        52
                    Met Gln Arg Gly Ala Ala Leu Cys Leu Arg Leu
                     1               5                  10 tgg ctc tgc ctg gga ctc ctg gac ggc ctg gtg agt ggc tac tcc atg       100
Trp Leu Cys Leu Gly Leu Leu Asp Gly Leu Val Ser Gly Tyr Ser Met
            15                  20                  25 acc ccc ccg acc ttg aac atc acg gag gag tca cac gtc atc gac acc       148
Thr Pro Pro Thr Leu Asn Ile Thr Glu Glu Ser His Val Ile Asp Thr
        30                  35                  40 ggt gac agc ctg tcc atc tcc tgc agg gga cag cac ccc ctc gag tgg       196
Gly Asp Ser Leu Ser Ile Ser Cys Arg Gly Gln His Pro Leu Glu Trp
    45                  50                  55 gct tgg cca gga gct cag gag gcg cca gcc acc gga gac aag gac agc       244
Ala Trp Pro Gly Ala Gln Glu Ala Pro Ala Thr Gly Asp Lys Asp Ser
60                  65                  70                  75 gag gac acg ggg gtg gtg cga gac tgc gag ggc aca gac gcc agg ccc       292
Glu Asp Thr Gly Val Val Arg Asp Cys Glu Gly Thr Asp Ala Arg Pro
                80                  85                  90 tac tgc aag gtg ttg ctg ctg cac gag gta cat gcc aac gac aca ggc       340
```

|  |  |  |  |  |  |  |  |  |  |  |  |  |  |  |  |
|---|---|---|---|---|---|---|---|---|---|---|---|---|---|---|---|
| Tyr | Cys | Lys | Val<br>95 | Leu | Leu | Leu | His<br>100 | Glu | Val | His | Ala<br>105 | Asn | Asp | Thr | Gly |

```
agc tac gtc tgc tac tac aag tac atc aag gca cgc atc gag ggc acc         388
Ser Tyr Val Cys Tyr Tyr Lys Tyr Ile Lys Ala Arg Ile Glu Gly Thr
            110                 115                 120 acg gcc gcc agc tcc tac gtg ttc gtg aga gac ttt gag cag cca ttc         436
Thr Ala Ala Ser Ser Tyr Val Phe Val Arg Asp Phe Glu Gln Pro Phe
    125                 130                 135 atc aac aag cct gac acg ctc ttg gtc aac agg aag gac gcc atg tgg         484
Ile Asn Lys Pro Asp Thr Leu Leu Val Asn Arg Lys Asp Ala Met Trp
140                 145                 150                 155 gtg ccc tgt ctg gtg tcc atc ccc ggc ctc aat gtc acg ctg cgc tcg         532
Val Pro Cys Leu Val Ser Ile Pro Gly Leu Asn Val Thr Leu Arg Ser
                160                 165                 170 caa agc tcg gtg ctg tgg cca gac ggg cag gag gtg gtg tgg gat gac         580
Gln Ser Ser Val Leu Trp Pro Asp Gly Gln Glu Val Val Trp Asp Asp
            175                 180                 185 cgg cgg ggc atg ctc gtg tcc acg cca ctg ctg cac gat gcc ctg tac         628
Arg Arg Gly Met Leu Val Ser Thr Pro Leu Leu His Asp Ala Leu Tyr
        190                 195                 200 ctg cag tgc gag acc acc tgg gga gac cag gac ttc ctt tcc aac ccc         676
Leu Gln Cys Glu Thr Thr Trp Gly Asp Gln Asp Phe Leu Ser Asn Pro
    205                 210                 215 ttc ctg gtg cac atc aca ggc aac gag ctc tat gac atc cag ctg ttg         724
Phe Leu Val His Ile Thr Gly Asn Glu Leu Tyr Asp Ile Gln Leu Leu
220                 225                 230                 235 ccc agg aag tcg ctg gag ctg ctg gta ggg gag aag ctg gtc ctg aac         772
Pro Arg Lys Ser Leu Glu Leu Leu Val Gly Glu Lys Leu Val Leu Asn
                240                 245                 250 tgc acc gtg tgg gct gag ttt aac tca ggt gtc acc ttt gac tgg gac         820
Cys Thr Val Trp Ala Glu Phe Asn Ser Gly Val Thr Phe Asp Trp Asp
            255                 260                 265 tac cca ggg aag cag gca gag cgg ggt aag tgg gtg ccc gag cga cgc         868
Tyr Pro Gly Lys Gln Ala Glu Arg Gly Lys Trp Val Pro Glu Arg Arg
        270                 275                 280 tcc cag cag acc cac aca gaa ctc tcc agc atc ctg acc atc cac aac         916
Ser Gln Gln Thr His Thr Glu Leu Ser Ser Ile Leu Thr Ile His Asn
    285                 290                 295 gtc agc cag cac gac ctg ggc tcg tat gtg tgc aag gcc aac aac ggc         964
Val Ser Gln His Asp Leu Gly Ser Tyr Val Cys Lys Ala Asn Asn Gly
300                 305                 310                 315 atc cag cga ttt cgg gag agc acc gag gtc att gtg cat gaa aat ccc        1012
Ile Gln Arg Phe Arg Glu Ser Thr Glu Val Ile Val His Glu Asn Pro
                320                 325                 330 ttc atc agc gtc gag tgg ctc aaa gga ccc atc ctg gag gcc acg gca        1060
Phe Ile Ser Val Glu Trp Leu Lys Gly Pro Ile Leu Glu Ala Thr Ala
            335                 340                 345 gga gac gag ctg gtg aag ctg ccc gtg aag ctg gcg gcg tac ccc ccg        1108
Gly Asp Glu Leu Val Lys Leu Pro Val Lys Leu Ala Ala Tyr Pro Pro
        350                 355                 360 ccc gag ttc cag tgg tac aag gat gga aag gca ctg tcc ggg cgc cac        1156
Pro Glu Phe Gln Trp Tyr Lys Asp Gly Lys Ala Leu Ser Gly Arg His
    365                 370                 375 agt cca cat gcc ctg gtg ctc aag gag gtg aca gag gcc agc aca ggc        1204
Ser Pro His Ala Leu Val Leu Lys Glu Val Thr Glu Ala Ser Thr Gly
380                 385                 390                 395 acc tac acc ctc gcc ctg tgg aac tcc gct gct ggc ctg agg cgc aac        1252
Thr Tyr Thr Leu Ala Leu Trp Asn Ser Ala Ala Gly Leu Arg Arg Asn
                400                 405                 410
```

-continued

```
atc agc ctg gag ctg gtg gtg aat gtg ccc ccc cag ata cat gag aag      1300
Ile Ser Leu Glu Leu Val Val Asn Val Pro Pro Gln Ile His Glu Lys
        415                 420                 425 gag gcc tcc tcc ccc agc atc tac tcg cgt cac agc cgc cag gcc ctc      1348
Glu Ala Ser Ser Pro Ser Ile Tyr Ser Arg His Ser Arg Gln Ala Leu
            430                 435                 440 acc tgc acg gcc tac ggg gtg ccc ctg cct ctc agc atc cag tgg cac      1396
Thr Cys Thr Ala Tyr Gly Val Pro Leu Pro Leu Ser Ile Gln Trp His
        445                 450                 455 tgg cgg ccc tgg aca ccc tgc aag atg ttt gcc cag cgt agt ctc cgg      1444
Trp Arg Pro Trp Thr Pro Cys Lys Met Phe Ala Gln Arg Ser Leu Arg
460                 465                 470                 475 cgg cgg cag cag caa gac ctc atg cca cag tgc cgt gac tgg agg gcg      1492
Arg Arg Gln Gln Gln Asp Leu Met Pro Gln Cys Arg Asp Trp Arg Ala
            480                 485                 490 gtg acc acg cag gat gcc gtg aac ccc atc gag agc ctg gac acc tgg      1540
Val Thr Thr Gln Asp Ala Val Asn Pro Ile Glu Ser Leu Asp Thr Trp
        495                 500                 505 acc gag ttt gtg gag gga aag aat aag act gtg agc aag ctg gtg atc      1588
Thr Glu Phe Val Glu Gly Lys Asn Lys Thr Val Ser Lys Leu Val Ile
            510                 515                 520 cag aat gcc aac gtg tct gcc atg tac aag tgt gtg gtc tcc aac aag      1636
Gln Asn Ala Asn Val Ser Ala Met Tyr Lys Cys Val Val Ser Asn Lys
525                 530                 535 gtg ggc cag gat gag cgg ctc atc tac ttc tat gtg acc acc atc ccc      1684
Val Gly Gln Asp Glu Arg Leu Ile Tyr Phe Tyr Val Thr Thr Ile Pro
540                 545                 550                 555 gac ggc ttc acc atc gaa tcc aag cca tcc gag gag cta cta gag ggc      1732
Asp Gly Phe Thr Ile Glu Ser Lys Pro Ser Glu Glu Leu Leu Glu Gly
            560                 565                 570 cag ccg gtg ctc ctg agc tgc caa gcc gac agc tac aag tac gag cat      1780
Gln Pro Val Leu Leu Ser Cys Gln Ala Asp Ser Tyr Lys Tyr Glu His
        575                 580                 585 ctg cgc tgg tac cgc ctc aac ctg tcc acg ctg cac gat gcg cac ggg      1828
Leu Arg Trp Tyr Arg Leu Asn Leu Ser Thr Leu His Asp Ala His Gly
            590                 595                 600 aac ccg ctt ctg ctc gac tgc aag aac gtg cat ctg ttc gcc acc cct      1876
Asn Pro Leu Leu Leu Asp Cys Lys Asn Val His Leu Phe Ala Thr Pro
605                 610                 615 ctg gcc gcc agc ctg gag gag gtg gca cct ggg gcg cgc cac gcc acg      1924
Leu Ala Ala Ser Leu Glu Glu Val Ala Pro Gly Ala Arg His Ala Thr
620                 625                 630                 635 ctc agc ctg agt atc ccc cgc gtc gcg ccc gag cac gag ggc cac tat      1972
Leu Ser Leu Ser Ile Pro Arg Val Ala Pro Glu His Glu Gly His Tyr
            640                 645                 650 gtg tgc gaa gtg caa gac cgg cgc agc cat gac aag cac tgc cac aag      2020
Val Cys Glu Val Gln Asp Arg Arg Ser His Asp Lys His Cys His Lys
        655                 660                 665 aag tac ctg tcg gtg cag gcc ctg gaa gcc cct cgg ctc acg cag aac      2068
Lys Tyr Leu Ser Val Gln Ala Leu Glu Ala Pro Arg Leu Thr Gln Asn
            670                 675                 680 ttg acc gac ctc ctg gtg aac gtg agc gac tcg ctg gag atg cag tgc      2116
Leu Thr Asp Leu Leu Val Asn Val Ser Asp Ser Leu Glu Met Gln Cys
685                 690                 695 ttg gtg gcc gga gcg cac gcg ccc agc atc gtg tgg tac aaa gac gag      2164
Leu Val Ala Gly Ala His Ala Pro Ser Ile Val Trp Tyr Lys Asp Glu
700                 705                 710                 715 agg ctg ctg gag gaa aag tct gga gtc gac ttg gcg gac tcc aac cag      2212
Arg Leu Leu Glu Glu Lys Ser Gly Val Asp Leu Ala Asp Ser Asn Gln
            720                 725                 730
```

-continued

| | |
|---|---|
| aag ctg agc atc cag cgc gtg cgc gag gag gat gcg gga cgc tat ctg<br>Lys Leu Ser Ile Gln Arg Val Arg Glu Glu Asp Ala Gly Arg Tyr Leu<br>             735                    740                   745 | 2260 |
| tgc agc gtg tgc aac gcc aag ggc tgc gtc aac tcc tcc gcc agc gtg<br>Cys Ser Val Cys Asn Ala Lys Gly Cys Val Asn Ser Ser Ala Ser Val<br>750                    755                    760 | 2308 |
| gcc gtg gaa ggc tcc gag gat aag ggc agc atg gag atc gtg atc ctt<br>Ala Val Glu Gly Ser Glu Asp Lys Gly Ser Met Glu Ile Val Ile Leu<br>765                    770                    775 | 2356 |
| gtc ggt acc ggc gtc atc gct gtc ttc ttc tgg gtc ctc ctc ctc<br>Val Gly Thr Gly Val Ile Ala Val Phe Phe Trp Val Leu Leu Leu Leu<br>780                    785                    790               795 | 2404 |
| atc ttc tgt aac atg agg agg ccg gcc cac gca gac atc aag acg ggc<br>Ile Phe Cys Asn Met Arg Arg Pro Ala His Ala Asp Ile Lys Thr Gly<br>             800                    805                    810 | 2452 |
| tac ctg tcc atc atc atg gac ccc ggg gag gtg cct ctg gag gag caa<br>Tyr Leu Ser Ile Ile Met Asp Pro Gly Glu Val Pro Leu Glu Glu Gln<br>815                    820                    825 | 2500 |
| tgc gaa tac ctg tcc tac gat gcc agc cag tgg gaa ttc ccc cga gag<br>Cys Glu Tyr Leu Ser Tyr Asp Ala Ser Gln Trp Glu Phe Pro Arg Glu<br>             830                    835                  840 | 2548 |
| cgg ctg cac ctg ggg aga gtg ctc ggc tac ggc gcc ttc ggg aag gtg<br>Arg Leu His Leu Gly Arg Val Leu Gly Tyr Gly Ala Phe Gly Lys Val<br>845                    850                    855 | 2596 |
| gtg gaa gcc tcc gct ttc ggc atc cac aag ggc agc agc tgt gac acc<br>Val Glu Ala Ser Ala Phe Gly Ile His Lys Gly Ser Ser Cys Asp Thr<br>860                    865                    870               875 | 2644 |
| gtg gcc gtg aaa atg ctg aaa gag ggc gcc acg gcc agc gag cac cgc<br>Val Ala Val Lys Met Leu Lys Glu Gly Ala Thr Ala Ser Glu His Arg<br>             880                    885                    890 | 2692 |
| gcg ctg atg tcg gag ctc aag atc ctc att cac atc ggc aac cac ctc<br>Ala Leu Met Ser Glu Leu Lys Ile Leu Ile His Ile Gly Asn His Leu<br>895                    900                    905 | 2740 |
| aac gtg gtc aac ctc ctc ggg gcg tgc acc aag ccg cag ggc ccc ctc<br>Asn Val Val Asn Leu Leu Gly Ala Cys Thr Lys Pro Gln Gly Pro Leu<br>             910                    915                    920 | 2788 |
| atg gtg atc gtg gag ttc tgc aag tac ggc aac ctc tcc aac ttc ctg<br>Met Val Ile Val Glu Phe Cys Lys Tyr Gly Asn Leu Ser Asn Phe Leu<br>925                    930                    935 | 2836 |
| cgc gcc aag cgg gac gcc ttc agc ccc tgc gcg gag aag tct ccc gag<br>Arg Ala Lys Arg Asp Ala Phe Ser Pro Cys Ala Glu Lys Ser Pro Glu<br>940                    945                    950               955 | 2884 |
| cag cgc gga cgc ttc cgc gcc atg gtg gag ctc gcc agg ctg gat cgg<br>Gln Arg Gly Arg Phe Arg Ala Met Val Glu Leu Ala Arg Leu Asp Arg<br>             960                    965                    970 | 2932 |
| agg cgg ccg ggg agc agc gac agg gtc ctc ttc gcg cgg ttc tcg aag<br>Arg Arg Pro Gly Ser Ser Asp Arg Val Leu Phe Ala Arg Phe Ser Lys<br>975                    980                    985 | 2980 |
| acc gag ggc gga gcg agg cgg gct tct cca gac caa gaa gct gag gac<br>Thr Glu Gly Gly Ala Arg Arg Ala Ser Pro Asp Gln Glu Ala Glu Asp<br>             990                    995                  1000 | 3028 |
| ctg tgg ctg agc ccg ctg acc atg gaa gat ctt gtc tgc tac agc<br>Leu Trp Leu Ser Pro Leu Thr Met Glu Asp Leu Val Cys Tyr Ser<br>1005                  1010                 1015 | 3073 |
| ttc cag gtg gcc aga ggg atg gag ttc ctg gct tcc cga aag tgc<br>Phe Gln Val Ala Arg Gly Met Glu Phe Leu Ala Ser Arg Lys Cys<br>1020                 1025                 1030 | 3118 |
| atc cac aga gac ctg gct gct cgg aac att ctg ctg tcg gaa agc<br>Ile His Arg Asp Leu Ala Ala Arg Asn Ile Leu Leu Ser Glu Ser | 3163 |

|  |  |  |  |  |  |  |  |  |  |  |
|---|---|---|---|---|---|---|---|---|---|---|
| | | | 1035 | | | | 1040 | | | 1045 |

```
gac gtg gtg aag atc tgt gac ttt ggc ctt gcc cgg gac atc tac       3208
Asp Val Val Lys Ile Cys Asp Phe Gly Leu Ala Arg Asp Ile Tyr
    1050                1055                1060 aaa gac cct gac tac gtc cgc aag ggc agt gcc cgg ctg ccc ctg       3253
Lys Asp Pro Asp Tyr Val Arg Lys Gly Ser Ala Arg Leu Pro Leu
1065                1070                1075 aag tgg atg gcc cct gaa agc atc ttc gac aag gtg tac acc acg       3298
Lys Trp Met Ala Pro Glu Ser Ile Phe Asp Lys Val Tyr Thr Thr
        1080                1085                1090 cag agt gac gtg tgg tcc ttt ggg gtg ctt ctc tgg gag atc ttc       3343
Gln Ser Asp Val Trp Ser Phe Gly Val Leu Leu Trp Glu Ile Phe
            1095                1100                1105 tct ctg ggg gcc tcc ccg tac cct ggg gtg cag atc aat gag gag       3388
Ser Leu Gly Ala Ser Pro Tyr Pro Gly Val Gln Ile Asn Glu Glu
1110                1115                1120 ttc tgc cag cgg ctg aga gac ggc aca agg atg agg gcc ccg gag       3433
Phe Cys Gln Arg Leu Arg Asp Gly Thr Arg Met Arg Ala Pro Glu
        1125                1130                1135 ctg gcc act ccc gcc ata cgc cgc atc atg ctg aac tgc tgg tcc       3478
Leu Ala Thr Pro Ala Ile Arg Arg Ile Met Leu Asn Cys Trp Ser
    1140                1145                1150 gga gac ccc aag gcg aga cct gca ttc tcg gag ctg gtg gag atc       3523
Gly Asp Pro Lys Ala Arg Pro Ala Phe Ser Glu Leu Val Glu Ile
1155                1160                1165 ctg ggg gac ctg ctc cag ggc agg ggc ctg caa gag gaa gag gag       3568
Leu Gly Asp Leu Leu Gln Gly Arg Gly Leu Gln Glu Glu Glu Glu
        1170                1175                1180 gtc tgc atg gcc ccg cgc agc tct cag agc tca gaa gag ggc agc       3613
Val Cys Met Ala Pro Arg Ser Ser Gln Ser Ser Glu Glu Gly Ser
    1185                1190                1195 ttc tcg cag gtg tcc acc atg gcc cta cac atc gcc cag gct gac       3658
Phe Ser Gln Val Ser Thr Met Ala Leu His Ile Ala Gln Ala Asp
1200                1205                1210 gct gag gac agc ccg cca agc ctg cag cgc cac agc ctg gcc gcc       3703
Ala Glu Asp Ser Pro Pro Ser Leu Gln Arg His Ser Leu Ala Ala
        1215                1220                1225 agg tat tac aac tgg gtg tcc ttt ccc ggg tgc ctg gcc aga ggg       3748
Arg Tyr Tyr Asn Trp Val Ser Phe Pro Gly Cys Leu Ala Arg Gly
    1230                1235                1240 gct gag acc cgt ggt tcc tcc agg atg aag aca ttt gag gaa ttc       3793
Ala Glu Thr Arg Gly Ser Ser Arg Met Lys Thr Phe Glu Glu Phe
1245                1250                1255 ccc atg acc cca acg acc tac aaa ggc tct gtg gac aac cag aca       3838
Pro Met Thr Pro Thr Thr Tyr Lys Gly Ser Val Asp Asn Gln Thr
        1260                1265                1270 gac agt ggg atg gtg ctg gcc tcg gag gag ttt gag cag ata gag       3883
Asp Ser Gly Met Val Leu Ala Ser Glu Glu Phe Glu Gln Ile Glu
    1275                1280                1285 agc agg cat aga caa gaa agc ggc ttc agg tagctgaagc agagagagag    3933
Ser Arg His Arg Gln Glu Ser Gly Phe Arg
1290                1295 aaggcagcat acgtcagcat tttcttctct gcacttataa gaaagatcaa agactttaag  3993
actttcgcta tttcttctac tgctatctac tacaaacttc aaagaggaac caggaggaca  4053
agaggagcat gaaagtggac aaggagtgtg accactgaag caccacaggg aaggggttag  4113
gcctccggat gactcgggc aggcctggat aatatccagc ctcccacaag aagctggtgg   4173
agcagagtgt tccctgactc ct                                          4195
```

<210> SEQ ID NO 4
<211> LENGTH: 1298
<212> TYPE: PRT

<213> ORGANISM: Homo sapiens

<400> SEQUENCE: 4

```
Met Gln Arg Gly Ala Ala Leu Cys Leu Arg Leu Trp Leu Cys Leu Gly
1               5                   10                  15
Leu Leu Asp Gly Leu Val Ser Gly Tyr Ser Met Thr Pro Pro Thr Leu
            20                  25                  30
Asn Ile Thr Glu Glu Ser His Val Ile Asp Thr Gly Asp Ser Leu Ser
        35                  40                  45
Ile Ser Cys Arg Gly Gln His Pro Leu Glu Trp Ala Trp Pro Gly Ala
    50                  55                  60
Gln Glu Ala Pro Ala Thr Gly Asp Lys Asp Ser Glu Asp Thr Gly Val
65                  70                  75                  80
Val Arg Asp Cys Glu Gly Thr Asp Ala Arg Pro Tyr Cys Lys Val Leu
                85                  90                  95
Leu Leu His Glu Val His Ala Asn Asp Thr Gly Ser Tyr Val Cys Tyr
            100                 105                 110
Tyr Lys Tyr Ile Lys Ala Arg Ile Glu Gly Thr Thr Ala Ala Ser Ser
        115                 120                 125
Tyr Val Phe Val Arg Asp Phe Glu Gln Pro Phe Ile Asn Lys Pro Asp
    130                 135                 140
Thr Leu Leu Val Asn Arg Lys Asp Ala Met Trp Val Pro Cys Leu Val
145                 150                 155                 160
Ser Ile Pro Gly Leu Asn Val Thr Leu Arg Ser Gln Ser Ser Val Leu
                165                 170                 175
Trp Pro Asp Gly Gln Glu Val Val Trp Asp Asp Arg Arg Gly Met Leu
            180                 185                 190
Val Ser Thr Pro Leu Leu His Asp Ala Leu Tyr Leu Gln Cys Glu Thr
        195                 200                 205
Thr Trp Gly Asp Gln Asp Phe Leu Ser Asn Pro Phe Leu Val His Ile
    210                 215                 220
Thr Gly Asn Glu Leu Tyr Asp Ile Gln Leu Leu Pro Arg Lys Ser Leu
225                 230                 235                 240
Glu Leu Leu Val Gly Glu Lys Leu Val Leu Asn Cys Thr Val Trp Ala
                245                 250                 255
Glu Phe Asn Ser Gly Val Thr Phe Asp Trp Asp Tyr Pro Gly Lys Gln
            260                 265                 270
Ala Glu Arg Gly Lys Trp Val Pro Glu Arg Arg Ser Gln Gln Thr His
        275                 280                 285
Thr Glu Leu Ser Ser Ile Leu Thr Ile His Asn Val Ser Gln His Asp
    290                 295                 300
Leu Gly Ser Tyr Val Cys Lys Ala Asn Asn Gly Ile Gln Arg Phe Arg
305                 310                 315                 320
Glu Ser Thr Glu Val Ile Val His Glu Asn Pro Phe Ile Ser Val Glu
                325                 330                 335
Trp Leu Lys Gly Pro Ile Leu Glu Ala Thr Ala Gly Asp Glu Leu Val
            340                 345                 350
Lys Leu Pro Val Lys Leu Ala Ala Tyr Pro Pro Pro Glu Phe Gln Trp
        355                 360                 365
Tyr Lys Asp Gly Lys Ala Leu Ser Gly Arg His Ser Pro His Ala Leu
    370                 375                 380
Val Leu Lys Glu Val Thr Glu Ala Ser Thr Gly Thr Tyr Thr Leu Ala
385                 390                 395                 400
```

```
Leu Trp Asn Ser Ala Gly Leu Arg Arg Asn Ile Ser Leu Glu Leu
                405                 410                 415

Val Val Asn Val Pro Pro Gln Ile His Glu Lys Glu Ala Ser Ser Pro
            420                 425                 430

Ser Ile Tyr Ser Arg His Ser Arg Gln Ala Leu Thr Cys Thr Ala Tyr
            435                 440                 445

Gly Val Pro Leu Pro Leu Ser Ile Gln Trp His Trp Arg Pro Trp Thr
450                 455                 460

Pro Cys Lys Met Phe Ala Gln Arg Ser Leu Arg Arg Gln Gln Gln
465                 470                 475                 480

Asp Leu Met Pro Gln Cys Arg Asp Trp Arg Ala Val Thr Thr Gln Asp
            485                 490                 495

Ala Val Asn Pro Ile Glu Ser Leu Asp Thr Trp Thr Glu Phe Val Glu
            500                 505                 510

Gly Lys Asn Lys Thr Val Ser Lys Leu Val Ile Gln Asn Ala Asn Val
            515                 520                 525

Ser Ala Met Tyr Lys Cys Val Val Ser Asn Lys Val Gly Gln Asp Glu
            530                 535                 540

Arg Leu Ile Tyr Phe Tyr Val Thr Thr Ile Pro Asp Gly Phe Thr Ile
545                 550                 555                 560

Glu Ser Lys Pro Ser Glu Glu Leu Leu Glu Gly Gln Pro Val Leu Leu
            565                 570                 575

Ser Cys Gln Ala Asp Ser Tyr Lys Tyr Glu His Leu Arg Trp Tyr Arg
            580                 585                 590

Leu Asn Leu Ser Thr Leu His Asp Ala His Gly Asn Pro Leu Leu Leu
            595                 600                 605

Asp Cys Lys Asn Val His Leu Phe Ala Thr Pro Leu Ala Ala Ser Leu
            610                 615                 620

Glu Glu Val Ala Pro Gly Ala Arg His Ala Thr Leu Ser Leu Ser Ile
625                 630                 635                 640

Pro Arg Val Ala Pro Glu His Glu Gly His Tyr Val Cys Glu Val Gln
            645                 650                 655

Asp Arg Arg Ser His Asp Lys His Cys His Lys Lys Tyr Leu Ser Val
            660                 665                 670

Gln Ala Leu Glu Ala Pro Arg Leu Thr Gln Asn Leu Thr Asp Leu Leu
            675                 680                 685

Val Asn Val Ser Asp Ser Leu Glu Met Gln Cys Leu Val Ala Gly Ala
            690                 695                 700

His Ala Pro Ser Ile Val Trp Tyr Lys Asp Glu Arg Leu Leu Glu Glu
705                 710                 715                 720

Lys Ser Gly Val Asp Leu Ala Asp Ser Asn Gln Lys Leu Ser Ile Gln
            725                 730                 735

Arg Val Arg Glu Glu Asp Ala Gly Arg Tyr Leu Cys Ser Val Cys Asn
            740                 745                 750

Ala Lys Gly Cys Val Asn Ser Ser Ala Ser Val Ala Val Glu Gly Ser
            755                 760                 765

Glu Asp Lys Gly Ser Met Glu Ile Val Ile Leu Val Gly Thr Gly Val
            770                 775                 780

Ile Ala Val Phe Phe Trp Val Leu Leu Leu Leu Ile Phe Cys Asn Met
785                 790                 795                 800

Arg Arg Pro Ala His Ala Asp Ile Lys Thr Gly Tyr Leu Ser Ile Ile
            805                 810                 815

Met Asp Pro Gly Glu Val Pro Leu Glu Glu Gln Cys Glu Tyr Leu Ser
```

```
                820                 825                 830
Tyr Asp Ala Ser Gln Trp Glu Phe Pro Arg Glu Arg Leu His Leu Gly
            835                 840                 845

Arg Val Leu Gly Tyr Gly Ala Phe Gly Lys Val Val Glu Ala Ser Ala
850                 855                 860

Phe Gly Ile His Lys Gly Ser Ser Cys Asp Thr Val Ala Val Lys Met
865                 870                 875                 880

Leu Lys Glu Gly Ala Thr Ala Ser Glu His Arg Ala Leu Met Ser Glu
            885                 890                 895

Leu Lys Ile Leu Ile His Ile Gly Asn His Leu Asn Val Val Asn Leu
            900                 905                 910

Leu Gly Ala Cys Thr Lys Pro Gln Gly Pro Leu Met Val Ile Val Glu
            915                 920                 925

Phe Cys Lys Tyr Gly Asn Leu Ser Asn Phe Leu Arg Ala Lys Arg Asp
    930                 935                 940

Ala Phe Ser Pro Cys Ala Glu Lys Ser Pro Glu Gln Arg Gly Arg Phe
945                 950                 955                 960

Arg Ala Met Val Glu Leu Ala Arg Leu Asp Arg Arg Arg Pro Gly Ser
            965                 970                 975

Ser Asp Arg Val Leu Phe Ala Arg Phe Ser Lys Thr Glu Gly Gly Ala
            980                 985                 990

Arg Arg Ala Ser Pro Asp Gln Glu Ala Glu Asp Leu Trp Leu Ser Pro
            995                 1000                1005

Leu Thr Met Glu Asp Leu Val Cys Tyr Ser Phe Gln Val Ala Arg
        1010                1015                1020

Gly Met Glu Phe Leu Ala Ser Arg Lys Cys Ile His Arg Asp Leu
        1025                1030                1035

Ala Ala Arg Asn Ile Leu Leu Ser Glu Ser Asp Val Val Lys Ile
        1040                1045                1050

Cys Asp Phe Gly Leu Ala Arg Asp Ile Tyr Lys Asp Pro Asp Tyr
        1055                1060                1065

Val Arg Lys Gly Ser Ala Arg Leu Pro Leu Lys Trp Met Ala Pro
        1070                1075                1080

Glu Ser Ile Phe Asp Lys Val Tyr Thr Thr Gln Ser Asp Val Trp
        1085                1090                1095

Ser Phe Gly Val Leu Leu Trp Glu Ile Phe Ser Leu Gly Ala Ser
        1100                1105                1110

Pro Tyr Pro Gly Val Gln Ile Asn Glu Glu Phe Cys Gln Arg Leu
        1115                1120                1125

Arg Asp Gly Thr Arg Met Arg Ala Pro Glu Leu Ala Thr Pro Ala
        1130                1135                1140

Ile Arg Arg Ile Met Leu Asn Cys Trp Ser Gly Asp Pro Lys Ala
        1145                1150                1155

Arg Pro Ala Phe Ser Glu Leu Val Glu Ile Leu Gly Asp Leu Leu
        1160                1165                1170

Gln Gly Arg Gly Leu Gln Glu Glu Glu Glu Val Cys Met Ala Pro
        1175                1180                1185

Arg Ser Ser Gln Ser Ser Glu Glu Gly Ser Phe Ser Gln Val Ser
        1190                1195                1200

Thr Met Ala Leu His Ile Ala Gln Ala Asp Ala Glu Asp Ser Pro
        1205                1210                1215

Pro Ser Leu Gln Arg His Ser Leu Ala Ala Arg Tyr Tyr Asn Trp
        1220                1225                1230
```

```
Val  Ser  Phe  Pro  Gly  Cys  Leu  Ala  Arg  Gly  Ala  Glu  Thr  Arg  Gly
     1235                     1240                    1245

Ser  Ser  Arg  Met  Lys  Thr  Phe  Glu  Glu  Phe  Pro  Met  Thr  Pro  Thr
     1250                     1255                    1260

Thr  Tyr  Lys  Gly  Ser  Val  Asp  Asn  Gln  Thr  Asp  Ser  Gly  Met  Val
     1265                     1270                    1275

Leu  Ala  Ser  Glu  Glu  Phe  Glu  Gln  Ile  Glu  Ser  Arg  His  Arg  Gln
     1280                     1285                    1290

Glu  Ser  Gly  Phe  Arg
     1295

<210> SEQ ID NO 5
<211> LENGTH: 537
<212> TYPE: PRT
<213> ORGANISM: Homo sapiens

<400> SEQUENCE: 5

Tyr  Ser  Met  Thr  Pro  Pro  Thr  Leu  Asn  Ile  Thr  Glu  Glu  Ser  His  Val
1                   5                   10                  15

Ile  Asp  Thr  Gly  Asp  Ser  Leu  Ser  Ile  Ser  Cys  Arg  Gly  Gln  His  Pro
               20                  25                  30

Leu  Glu  Trp  Ala  Trp  Pro  Gly  Ala  Gln  Glu  Ala  Pro  Ala  Thr  Gly  Asp
          35                  40                  45

Lys  Asp  Ser  Glu  Asp  Thr  Gly  Val  Val  Arg  Asp  Cys  Glu  Gly  Thr  Asp
     50                  55                  60

Ala  Arg  Pro  Tyr  Cys  Lys  Val  Leu  Leu  Leu  His  Glu  Val  His  Ala  Gln
65                  70                  75                  80

Asp  Thr  Gly  Ser  Tyr  Val  Cys  Tyr  Tyr  Lys  Tyr  Ile  Lys  Ala  Arg  Ile
               85                  90                  95

Glu  Gly  Thr  Thr  Ala  Ala  Ser  Ser  Tyr  Val  Phe  Val  Arg  Asp  Phe  Glu
               100                 105                 110

Gln  Pro  Phe  Ile  Asn  Lys  Pro  Asp  Thr  Leu  Leu  Val  Asn  Arg  Lys  Asp
          115                 120                 125

Ala  Met  Trp  Val  Pro  Cys  Leu  Val  Ser  Ile  Pro  Gly  Leu  Asn  Val  Thr
     130                 135                 140

Leu  Arg  Ser  Gln  Ser  Ser  Val  Leu  Trp  Pro  Asp  Gly  Gln  Glu  Val  Val
145                 150                 155                 160

Trp  Asp  Asp  Arg  Arg  Gly  Met  Leu  Val  Ser  Thr  Pro  Leu  Leu  His  Asp
               165                 170                 175

Ala  Leu  Tyr  Leu  Gln  Cys  Glu  Thr  Thr  Trp  Gly  Asp  Gln  Asp  Phe  Leu
          180                 185                 190

Ser  Asn  Pro  Phe  Leu  Val  His  Ile  Thr  Gly  Asn  Glu  Leu  Tyr  Asp  Ile
          195                 200                 205

Gln  Leu  Leu  Pro  Arg  Lys  Ser  Leu  Glu  Leu  Leu  Val  Gly  Glu  Lys  Leu
     210                 215                 220

Val  Leu  Asn  Cys  Thr  Val  Trp  Ala  Glu  Phe  Asn  Ser  Gly  Val  Thr  Phe
225                 230                 235                 240

Asp  Trp  Asp  Tyr  Pro  Gly  Lys  Gln  Ala  Glu  Arg  Gly  Lys  Trp  Val  Pro
               245                 250                 255

Glu  Arg  Arg  Ser  Gln  Gln  Thr  His  Thr  Glu  Leu  Ser  Ser  Ile  Leu  Thr
               260                 265                 270

Ile  His  Asn  Val  Ser  Gln  His  Asp  Leu  Gly  Ser  Tyr  Val  Cys  Lys  Ala
          275                 280                 285

Asn  Asn  Gly  Ile  Gln  Arg  Phe  Arg  Glu  Ser  Thr  Glu  Val  Ile  Val  His
```

```
                    290                 295                 300
Glu Glu Pro Lys Ser Cys Asp Lys Thr His Thr Cys Pro Pro Cys Pro
305                 310                 315                 320

Ala Pro Glu Leu Leu Gly Gly Pro Ser Val Phe Leu Phe Pro Pro Lys
                325                 330                 335

Pro Lys Asp Thr Leu Met Ile Ser Arg Thr Pro Glu Val Thr Cys Val
                340                 345                 350

Val Val Asp Val Ser His Glu Asp Pro Glu Val Lys Phe Asn Trp Tyr
                355                 360                 365

Val Asp Gly Val Glu Val His Asn Ala Lys Thr Lys Pro Arg Glu Glu
                370                 375                 380

Gln Tyr Asn Ser Thr Tyr Arg Val Val Ser Val Leu Thr Val Leu His
385                 390                 395                 400

Gln Asp Trp Leu Asn Gly Lys Glu Tyr Lys Cys Lys Val Ser Asn Lys
                405                 410                 415

Ala Leu Pro Ala Pro Ile Glu Lys Thr Ile Ser Lys Ala Lys Gly Gln
                420                 425                 430

Pro Arg Glu Pro Gln Val Tyr Thr Leu Pro Pro Ser Arg Asp Glu Leu
                435                 440                 445

Thr Lys Asn Gln Val Ser Leu Thr Cys Leu Val Lys Gly Phe Tyr Pro
                450                 455                 460

Ser Asp Ile Ala Val Glu Trp Glu Ser Asn Gly Gln Pro Glu Asn Asn
465                 470                 475                 480

Tyr Lys Thr Thr Pro Pro Val Leu Asp Ser Asp Gly Ser Phe Phe Leu
                485                 490                 495

Tyr Ser Lys Leu Thr Val Asp Lys Ser Arg Trp Gln Gln Gly Asn Val
                500                 505                 510

Phe Ser Cys Ser Val Met His Glu Ala Leu His Asn His Tyr Thr Gln
                515                 520                 525

Lys Ser Leu Ser Leu Ser Pro Gly Lys
                530                 535
```

UNITED STATES PATENT AND TRADEMARK OFFICE
CERTIFICATE OF CORRECTION

PATENT NO. : 10,274,503 B2  
APPLICATION NO. : 14/888062  
DATED : April 30, 2019  
INVENTOR(S) : Baldwin et al.

Page 1 of 1

It is certified that error appears in the above-identified patent and that said Letters Patent is hereby corrected as shown below:

In the Claims

In Claim 7, Column 69, Line 27, after VEGF-C protein delete "or VEGF-C mRNA".

Signed and Sealed this  
Twentieth Day of April, 2021

Drew Hirshfeld  
*Performing the Functions and Duties of the*  
*Under Secretary of Commerce for Intellectual Property and*  
*Director of the United States Patent and Trademark Office*